US010633451B2

(12) United States Patent
Bourquin et al.

(10) Patent No.: US 10,633,451 B2
(45) Date of Patent: Apr. 28, 2020

(54) BISPECIFIC ANTIBODY MOLECULES WITH ANTIGEN-TRANSFECTED T-CELLS AND THEIR USE IN MEDICINE

(71) Applicants: Hoffmann-La Roche Inc., Nutley, NJ (US); LUDWIG-MAXIMILLIANS-UNIVERSITÄT MÜNCHEN, Munich (DE)

(72) Inventors: Carole Bourquin, Belfaux (CH); Raffaella Castoldi, Munich (DE); Stefan Endres, Munich (DE); Christian Klein, Bonstetten (CH); Sebastian Kobold, Munich (DE); Gerhard Niederfellner, Oberhausen (DE); Claudio Sustmann, Munich (DE)

(73) Assignees: Hoffmann-La Roche Inc., Nutley, NJ (US); Ludwig-Maximillians-Universität München, München (DE)

( * ) Notice: Subject to any disclaimer, the term of this patent is extended or adjusted under 35 U.S.C. 154(b) by 397 days.

(21) Appl. No.: 14/376,364

(22) PCT Filed: Jan. 24, 2013

(86) PCT No.: PCT/EP2013/051351
§ 371 (c)(1),
(2) Date: Aug. 1, 2014

(87) PCT Pub. No.: WO2013/113615
PCT Pub. Date: Aug. 8, 2013

(65) Prior Publication Data

US 2015/0010567 A1 Jan. 8, 2015

(30) Foreign Application Priority Data

Feb. 3, 2012 (EP) .................................... 12153786

(51) Int. Cl.

| | |
|---|---|
| ***C07K 16/30*** | (2006.01) |
| ***C07K 16/28*** | (2006.01) |
| ***A61K 39/00*** | (2006.01) |
| ***A61K 39/395*** | (2006.01) |
| ***C07K 16/32*** | (2006.01) |

(52) U.S. Cl.
CPC .......... *C07K 16/30* (2013.01); *A61K 39/0011* (2013.01); *A61K 39/39558* (2013.01); *C07K 16/2863* (2013.01); *C07K 16/32* (2013.01); *A61K 2039/505* (2013.01); *A61K 2039/5158* (2013.01); *C07K 2317/31* (2013.01); *Y02P 20/582* (2015.11)

(58) Field of Classification Search
CPC ................ C07K 16/30; C07K 16/2863; A61K 39/0011; A61K 39/39558
USPC ................................ 424/133.1, 136.1, 178.1
See application file for complete search history.

(56) References Cited

U.S. PATENT DOCUMENTS

2015/0166670 A1* 6/2015 Castoldi ........... A61K 39/39558 424/136.1

FOREIGN PATENT DOCUMENTS

| | | | |
|---|---|---|---|
| WO | 01/77342 | A1 | 10/2001 |
| WO | WO 2004/003019 | * | 6/2004 |
| WO | 2009/080251 | A1 | 7/2009 |
| WO | 2009/080252 | A1 | 7/2009 |
| WO | 2009/080253 | A1 | 7/2009 |
| WO | 2009/080254 | A1 | 7/2009 |
| WO | 2010/112193 | A1 | 10/2010 |
| WO | 2010/115589 | A1 | 10/2010 |
| WO | 2010/136172 | A1 | 12/2010 |
| WO | 2010/145792 | A1 | 12/2010 |
| WO | 2010/145793 | A1 | 12/2010 |
| WO | 2011/117330 | A1 | 9/2011 |

OTHER PUBLICATIONS

Ward et al. (Nature 341:544-546 (1989)).*
Smith-Gill et al. (J. Immunol. 139:4135-4144 (1987)).*
(Continued)

*Primary Examiner* — Lynn A Bristol
(74) *Attorney, Agent, or Firm* — Grimes & Yvon LLP

(57) ABSTRACT

The present invention relates to a bispecific (monoclonal) antibody molecule with a first binding domain binding an antigen on CD8+ T-cells that does not naturally occur in and/or on CD8+ T-cells and a second binding domain binding to a tumor specific antigen naturally occurring on the surface of a tumor cell. The bispecific (monoclonal) antibody molecules are particularly useful in combination with transduced CD8+ T-cells comprising an antigen which does not naturally occur in and/or on $CD8^+$ T-cells and/or a T-cell receptor. The invention provides the use of said (bispecific) antibody molecules as a medicament, the (bispecific) antibody molecules for use in a method for the treatment of particular diseases as well as a pharmaceutical composition/medicament comprising said (bispecific) antibody molecules, wherein said (bispecific) antibody molecules are to be administered in combination with transduced CD8+ T-cells comprising an antigen which does not naturally occur in and/or on CD8+ T-cells and/or a T-cell receptor in a specific treatment regimen. Further aspects of the invention are nucleic acid sequences encoding said bispecific (monoclonal) antibody molecules, vectors.host cells, methods for the production of the (bispecific) antibody molecule as well as a kit comprising the (bispecific) antibody molecule of the invention.

16 Claims, 22 Drawing Sheets

Figure 1:
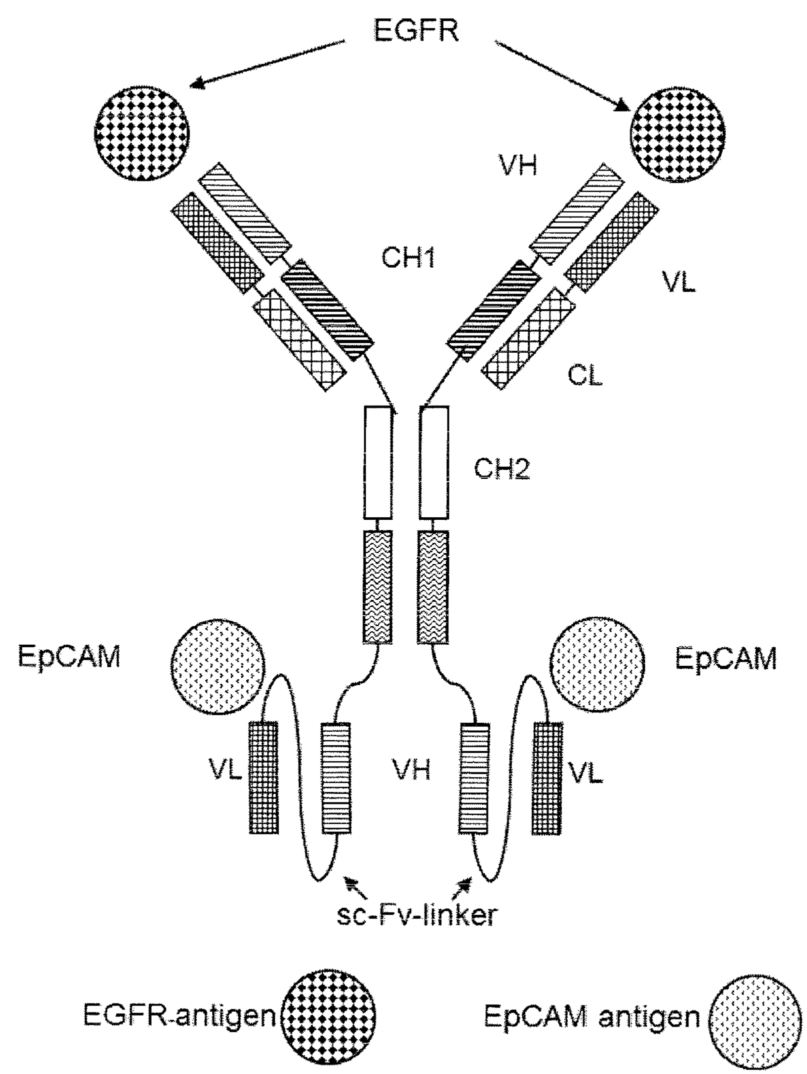

Specification includes a Sequence Listing.

(56) References Cited

OTHER PUBLICATIONS

Kumar et al. (J. Biol. Chem. 275:35129-35136 (2000)).*
Song et al. (Biochem Biophys Res Comm 268:390-394 (2000)).*
Kobold et al. ( J Natl Cancer Inst (2015) 107(1): dju364; First published online Nov. 24, 2014).*
Kobold et al. Dtsch Arztebl Int 2015; 112: 809-15.*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Kobald et al. (Oncology Research and Treatment, 37, Supp. 5, pp. 239. Abstct No. V741 (Oct. 2014)).*
James et al., "Antigen Sensitivity of CD22-Specific Chimeric TCR Is Modulated by Target Epitope Distance from the Cell Membrane" J Immunol 108:7028-7038 ( 2008).
Kochenderfer et al., "Construction and Pre-clincal Evaluation of an Anti-CD19 Chimeric Antigen Receptor" J Immunother 32(7):689-702 (Sep. 2009).
Molhoj et al., "CD19-/CD3-bispecific antibody of the BiTE class is far superior to tandem diabody with respect to redirected tumor cell lysis" Molecular Immunology 44:1935-1943 ( 2007).
Balzar et al., "The biology of the 17-1A antigen (Ep-CAM)" J Mol Med 77(10):699-712.
Bargou et al., "Tumor regression in cancer patients by very low doses of a T cell-engaging antibody" Science 321(5891):974-977 ( 2008).
Brandt et al., "'Bispecific antibody fragments with CD20×CD28 specificity allow effective autologous and allogeneic T-cell activation against malignant cells in peripheral blood and bone marrow cultures from patients with B-cell lineage leukemia and lymphoma'" Experimental Hematology [XP002975224, Elsevier Inc, US ISSN: 0301-472X, DOI: 10.1016/S0301-472X(99)00072-7] 35:1264-70 (Aug. 1, 1999).
Brischwein et al., "MT110: a novel bispecific single-chain antibody construct with high efficacy in eradicating established tumors" Mol Immunol. 43(8):1129-43 ( 2006).
Chaubal et al., "Ep-CAM—a marker for the detection of disseminated tumor cells in patients suffering from SCCHN" Anticancer Res. 19:2237-42 ( 1999).
Chen et al., "Monocyte-mediated lysis of acute myeloid leukemia cells in the presence of the bispecific antibody 251×22 (anti-CD33×anti-CD64)" Clin Cancer Res. 1(11):1319-25 (Nov. 1, 1995).
Coloma and Morrison, "Design and production of novel tetravalent bispecific antibodies" Nat Biotechnol 15(2):159-163 (Feb. 1997).
Database Biosis [Online] Biosciences Information Service, Philadelphia, PA, US; Nov. 2010 (Nov. 2010), Curran Kevin J et al: 'Virus Specific T-Lymphocytes Genetically Modified to Target the CD19 Antigen Eradicates Systemic Lymphoma in Mice', XP002679901, Database accession No. PREV201100424635.
Database Biosis [Online] Biosciences Information Service, Philadelphia, PA, US; Nov. 2011 (Nov. 2011), Miyazaki Yukihiro et al: 'Human Telomerase Reverse Transcriptase-Specific T-Cell Receptor Gene Transfer Redirects T-Lymphocytes to Exert Effective Antitumor Reactivity Against Adult T-Cell Leukemia', XP002679898, Database accession No. PREV201200221443.
Database Biosis [Online] Biosciences Information Service, Philadelphia, PA, US; Nov. 2011 (Nov. 2010), XP002679891, Database accession No. PREV2011200220986 abstract & Blood, vol. 118, No. 21, Nov. 2011 (Nov. 2010), p. 1585, 53rd Annual Meeting of the American-Society-of-Hematology (ASH); Orlando, FL, USA; Dec. 10 -13, 2011 ISSN: 0006-4971(print).
Database Biosis [Online] Biosciences Information Service, Philadelphia, PA, US; Nov. 2010 (Nov. 2010), Glorius Pia et al: 'The Novel Bispecific Antibody [(CD20)(2)×CD16] Efficiently Triggers Lysis of Neoplastic B Cells', XP002679890, Database accession No. PREV201100425389 & Blood, vol. 116, No. 21, Nov. 2010 (Nov. 2010), p. 1173, 52nd Annual Meeting of the American-Society-of-Hematology (ASH); Orlando, FL, USA; Dec. 4-7, 2010 ISSN: 0006-4971(print).
Fischer et al., "Bispecific Antibodies: Molecules that Enable Novel Therapeutic Strategies" Pathobiology 74:3-14 ( 2007).
Friedman et al., "Engineering and characterization of a bispecific HER2×EGFR-binding affibody molecule" Biotechnol Appl Biochem. 54(2):121-31 (2009).
Gastl et al., "Ep-CAM overexpression in breast cancer as a predictor of survival" Lancet 356:1981-2 (2000).
Gelderman et al., "Cross-linking tumor cells with effector cells via CD55 with a bispecific mAb induces beta-glucan-dependent CR3-dependent cellular cytotoxicity" Eur J Immunol. 36(4):977-84 (Apr. 2006).
Holliger et al., "Engineered antibody fragments and the rise of single domains" Nat Biotechnol 23(9):1126-36 (Sep. 2005).
James et al., "Antigen sensitivity of CD22-specific chimeric TCR is modulated by target epitope distance from the cell membrane" J Immunol 180(10):7028-38 (May 2008).
James et al., "Immunotherapy with the bispecific antibody MDX-H210 (anti-HER2×anti-CD64) combined with GM-CSF in HER2 positive hormone resistant prostatic cancer" European Journal of cancer 35:S343-S344 (Sep. 1999).
Kasuya et al., "Bispecific anti-HER2 and CD16 single-chain antibody production prolongs the use of stem cell-like cell transplantation against HER2-overexpressing cancer" Int J Mol Med. 25(2):209-15 (Feb. 2010).
Khor, "A phase 1 trial of humanized monoclonal antibody 3622W94 including pharmacokinetics (PK) and immunogenicity evaluation" Proceedings of the American Society of Clinicaloncology (1997), 847.
Leen et al., "Improving T cell therapy for cancer" Annu Rev Immunol. 25:243-65 ( 2007).
Litvinov et al., "Expression of Ep-CAM in cervical squamous epithelia correlates with an increased proliferation and the disappearance of markers for terminal differentiation" Am J Pathol. 148(3):865-75 ( 1996).
Lobuglio, "A phase I trial of the humanized anti-EGP40 monoclonal antibody" Abstract Proceedings of the American Society of Clinical Oncology (1997), 1562.
Lorimer et al., "Recombinant immunotoxins specific for a mutant epidermal growth factor receptor: targeting with a single chain antibody variable domain isolated by phage display" Proc Natl Acad Sci U S A. 93(25):14815-20 ( 1996).
Macora et al., "Development ofhumanbispecific antibodies against CD20/CD55" Molecular Immunology 47(13):2287.
Martin et al., "Expression of the 17-1A antigen in gastric and gastro-oesophageal junction adenocarcinomas: a potential immunotherapeutic target?" J Clin Pathol. 52(9):701-4 ( 1999).
Morgan et al., "Cancer regression in patients after transfer of genetically engineered lymphocytes" Science 314(5796):126-9 (Oct. 2006).
Morrison, "Two Heads are Better than One" Nat Biotechnol 25(11):1233-34 (Nov. 2007).
Offner et al., "Induction of regular cytolytic T cell synapses by bispecific single-chain antibody constructs on MHC class I-negative tumor cells" Mol Immunol. 43(6):763-71 (Feb. 2006).
Passlick et al., "The 17-1A antigen is expressed on primary, metastatic and disseminated non-small cell lung carcinoma cells" Int J Cancer. 87(4):548-52 ( 2000).
Piyathilake et al., "The expression of Ep-CAM (17-1A) in squamous cell cancers of the lung" Hum Pathol. 31(4):482-7 ( 2000).
Poczatek et al., "Ep-Cam levels in prostatic adenocarcinoma and prostatic intraepithelial neoplasia" J Urol. 162(4):1462-6 ( 1999).
Qu et al., "Bispecific anti-CD20/22 antibodies inhibit B-cell lymphoma proliferation by a unique mechanism of action" Blood 111(4):2211-9 ( 2008).
Quak et al., "Production of a monoclonal antibody (K 931) to a squamous cell carcinoma associated antigen identified as the 17-1A antigen" Hybridoma 94:377-87 ( 1990).

(56) References Cited

OTHER PUBLICATIONS

Rowley et al., "Expression of IL-15RA or an IL-15/IL-15RA fusion on CD8+ T cells modifies adoptively transferred T-cell function in cis" Eur J Immunol. 39(2):491-506 ( 2009).

Schaefer et al., "A two-in-one antibody against HER3 and EGFR has superior inhibitory activity compared with monospecific antibodies original research article" Cancer Cell 20:472-486 ( 2011).

Schweizer et al., "Efficient carcinoma cell killing by activated polymorphonuclear neutrophils targeted with an EP-CAM×CD64 (HEA125×197) bispecific antibody" Cancer Immunol Immunother. 151(11-12):621-9 (Dec. 2002).

Shen et al., "single Variable Domain Antibody as a Versatile Buildin Block for the Construction of IgG-like Bispecific Antibodies" Journal of Immunological Methods 318:65-74 ( 2007).

Singer et al., "Effective elimination of acute myeloid leukemic cells by recombinant bispecific antibody derivatives directed against CD33 and CD16" J Immunother. 33(6):599-608 ( 2010).

Suntharalingam et al., "Cytokine storm in a phase 1 trial of the anti-CD28 monoclonal antibody TGN1412" N Engl J Med. 355(10):1018-28 ( 2006).

Tanja Hermann et al., "Construction of Optimized Bispecific Antibodies for Selective Activation of the Death Receptor CD95" 68:1221-1227 ( 2008).

Topp et al., "Targeted therapy with the T-cell-engaging antibody blinatumomab of chemotherapy-refractory minimal residual disease in B-lineage acute lymphoblastic leukemia patients results in high response rate and prolonged leukemia-free survival" J Clin Oncol. 29(18):2493-8 ( 2011).

Topp et al., "Treatment with Anti-CD19 BiTE Antibody Blinatumomab (MT103 / MEDI-538) Is Able to Eliminate Minimal Residual Disease (MRD) in Patients with B-Precursor Acute Lymphoblastic Leukemia (ALL): First Results of an Ongoing Phase II Study" Abstract Blood (ASH Annual Meeting Abstracts) 2008 112: Abstract 1926.

Vallera et al., "Bioengineering a unique deimmunized bispecific targeted toxin that simultaneously recognizes human CD22 and CD19 receptors in a mouse model of B-cell metastases" Mol Cancer Ther. 9(6):1872-83 ( 2010).

Wu et al., "Simultaneous Targeting of Multiple Disease Mediators by a Dual-Variable-Domain Immunoglobulin" Nature Biotech. 25:1290-1297 ( 2007).

Ikezoe, T et al., The antitumor effects of sunitinib (formerly SU11248) against a variety of human hematologic malignancies . . . ; Mol. Cancer Ther. 5:2522-2530 (2006).

Lopes De Menezes, De et al., CHIR-258: A Potent Inhibitor of FLT3 Kinase in Experimental Tumor Xenograft Models . . . ; Clin. Cancer Res. 11:5281-5291 (2005).

Renhowe, P et al., Design, Structure-Activity Relationships and in Vivo Characterization of 4-Amino-3-benzimidazol-2-ylhydroquinolin-2-ones . . . ; J. Med. Chem. 52:278-292 (2009).

Simplicio, AL et al., Prodrugs for Amines; Molecules 13:519-547 (2008).

Stenesh, J et al., Dictionary of Biochemistry and Molecular Biology, 2nd Ed., pp. 307; John Wiley & Sons, USA (1989).

Yata, N, Concept of a Prodrug; Prog. Med. 5:2152-2158 (1985).

Translation of Office Action from related application JP 2018-029507 (dated May 14, 2019).

* cited by examiner

Figure 3
A
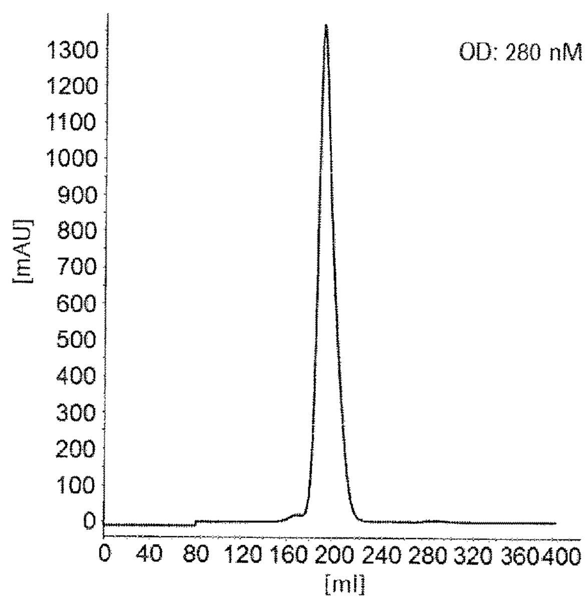
B
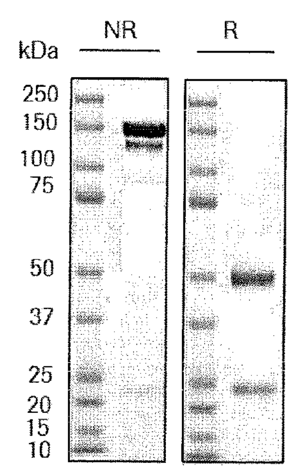

Significance:

<u>Gr. 1 vs. 4</u>: | | day 31, | | | day 35, $p<0.001$ from day 35

<u>Gr. 2 vs. 4:</u> | | day 40, | | | day 42, $p<0.001$ from day 42

<u>Gr. 3 vs. 4:</u> | | day 50, | | | day 53, $p<0.001$ from day 48

Gr. 1 vs. 4 p=0.0001

Gr. 2 vs. 4 p=0.0005

Gr. 3 vs. 4 p=0.0087

Significance:

Gr. 1 vs. 4: | | day 36, | | | day 47, $p<0.001$

Gr. 2 vs. 4: | | day 47, | | | day 50, $p<0.001$

Gr. 3 vs. 4: | | day 54, | | | day 57, $p<0.001$

Gr. 4 vs. 5: | | day 63, | | | day 65, $p<0.001$

Figure 14

Significance:

p < 0.0001 for PBS, aEpCAM; BiAb, and T-cell + Ab to T-cell + either low or high dose

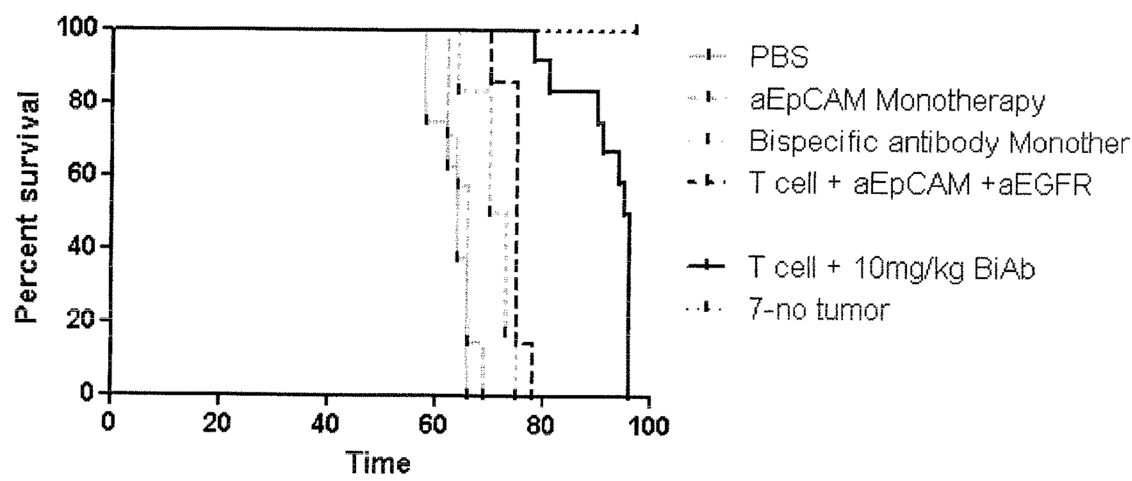

Figure 15

*murine EpCAM His-Avitag Protein Sequence* magpqalafglllavvtatlaaaqrdcvcdnyklatscslneygecqctsygtqntvicskla
skclamkaemthsksgrrikpegaiqnndglydpdcdeqglfkakqcngtatcwcvntagvrr
tdkdteitcservrtywiiielkhkerespydhqslqtalqeaftsryklnqkfiknimyenn
vitidlmqnssqktqddvdiadvayyfekdvkgeslfhssksmdlrvngepldldpgqtliyy
vdekapefsmqgltaaalevlfqgpgthhhhhhhhhhiglndifeaqkiewhe

*Bold Font = EpCAM CDS*

*Normal Font = His-Avitag*

Figure 16

*murine EpCAM CDS (encodes aa 1-267)* atggctggacctcaggccctggcctttggcctgctgctggccgtcgtgacagccacactggcc
gctgcccagagggactgcgtgtgcgacaactataagctggccaccagctgcagcctgaacgag
tacggcgagtgccagtgcaccagctacggcacccagaacaccgtgatctgcagcaagctggct
tccaagtgcctggccatgaaggccgagatgacccacagcaagagcggcagacggatcaagccc
gagggcgccatccagaacaacgacggcctgtacgaccccgactgcgacgagcagggcctgttc
aaggccaagcagtgcaacggcaccgccacctgttggtgtgtgaacacagctggcgtgcggcgg
acagacaaggacaccgagatcacctgtagcgagagagtgcggacctactggatcatcatcgag
ctgaagcacaaagagagagagagagcccctacgaccaccagagcctgcagaccgccctgcaagaa
gccttcaccagccggtacaagctgaaccagaagttcatcaagaacattatgtacgagaacaac
gtgatcaccatcgacctgatgcagaacagcagccagaaaacccaggacgacgtggacattgcc
gacgtggcctactacttcgagaaggacgtgaagggcgagagcctgttccacagcagcaagagc
atggacctgagagtgaacggcgagcccctggacctggaccctggccagaccctgatctactac
gtggacgagaaggcccccgagttcagcatgcagggcctgaccgcg

A

B

Figure 23

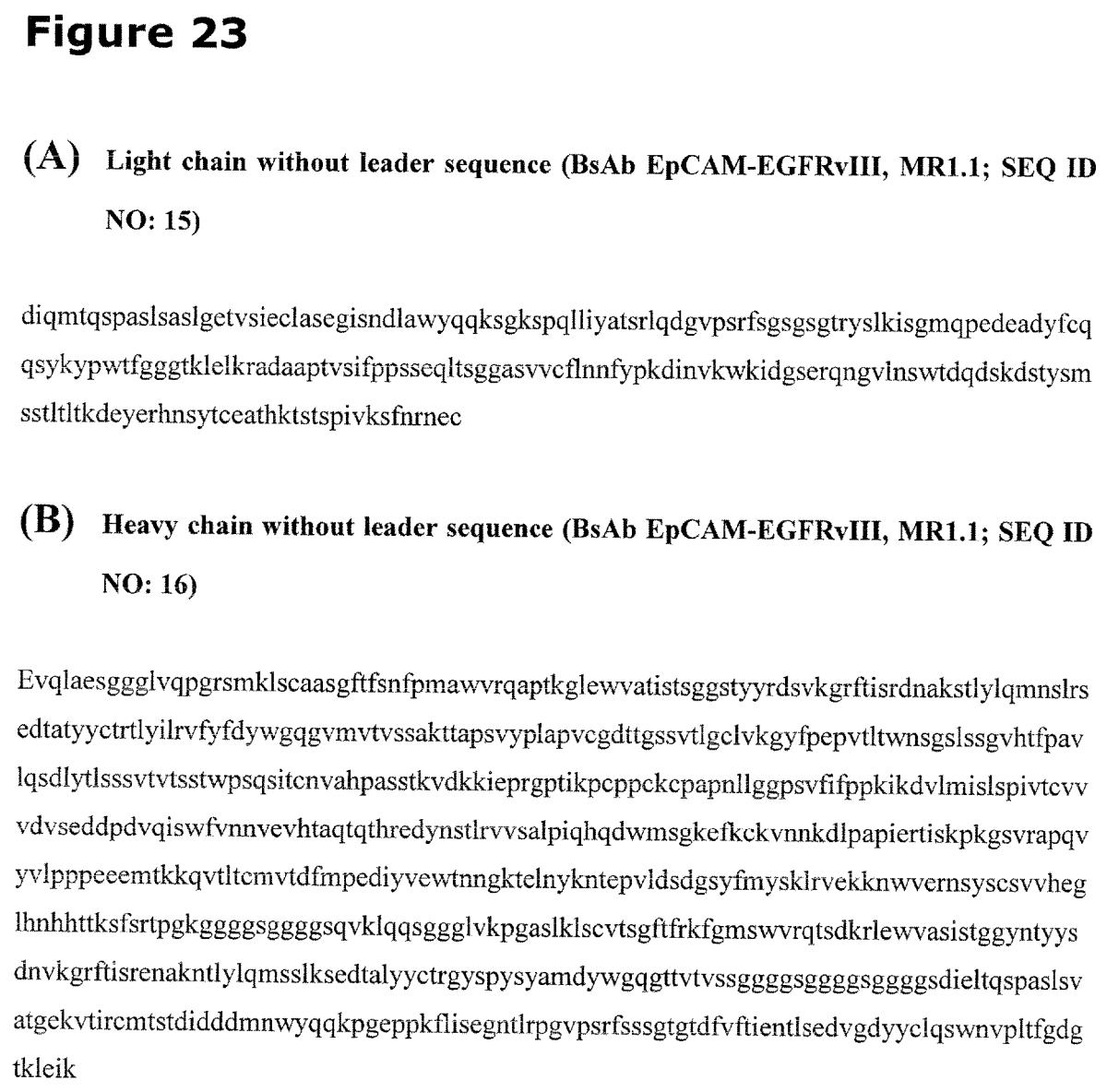

(A) Light chain without leader sequence (BsAb EpCAM-EGFRvIII, MR1.1; SEQ ID NO: 15)

diqmtqspaslsaslgetvsieclasegisndlawyqqksgkspqlliyatsrlqdgvpsrfsgsgsgtryslkisgmqpedeadyfcq qsykypwtfgggtklelkradaaptvsifppsseqltsggasvvcflnnfypkdinvkwkidgserqngvlnswtdqdskdstysm sstltltkdeyerhnsytceathktstspivksfnrnec

(B) Heavy chain without leader sequence (BsAb EpCAM-EGFRvIII, MR1.1; SEQ ID NO: 16)

Evqlaesggglvqpgrsmklscaasgftfsnfpmawvrqaptkglewvatistsggstyyrdsvkgrftisrdnakstlylqmnslrs edtatyyctrtlyilrvfyfdywgqgvmvtvssakttapsvyplapvcgdttgssvtlgclvkgyfpepvtltwnsgslssgvhtfpav lqsdlytlsssvtvtsstwpsqsitcnvahpasstkvdkkieprgptikpcppckcpapnllggpsvfifppkikdvlmislspivtcvv vdvseddpdvqiswfvnnvevhtaqtqthredynstlrvvsalpiqhqdwmsgkefkckvnnkdlpapiertiskpkgsvrapqv yvlpppeeemtkkqvtltcmvtdfmpediyvewtnngktelnykntepvldsdgsyfmysklrvekknwvernsyscsvvheg lhnhhttksfsrtpgkggggsggggsqvklqqsggglvkpgaslklscvtsgftfrkfgmswvrqtsdkrlewvasistggyntyys dnvkgrftisrenakntlylqmsslksedtalyyctrgyspysyamdywgqgttvtvssggggsggggsggggsdieltqspaslsv atgekvtircmtstdidddmnwyqqkpgeppkflisegntlrpgvpsrfsssgtgtdfvftientlsedvgdyyclqswnvpltfgdg tkleik

Figure 24

(A) DNA sequence of del-hEGFRvIII (SEQ ID NO: 17)

gcggccgcgccaccatgcgaccctccgggacggccggggcagcgctcctggcgctgctggctgcgctctgcccggcgagtcgggct
ctggaggaaaagaaaggtaattatgtggtgacagatcacggctcgtgcgtccgagcctgtggggccgacagctatgagatggaggaag
acggcgtccgcaagtgtaagaagtgcgaagggccttgccgcaaagtgtgtaacggaataggtattggtgaatttaaagactcactctcca
taaatgctacgaatattaaacacttcaaaaactgcacctccatcagtggcgatctccacatcctgccggtggcatttaggggtgactccttca
cacatactcctcctctggatccacaggaactggatattctgaaaaccgtaaaggaaatcacagggtttttgctgattcaggcttggcctgaa
aacaggacggacctccatgcctttgagaacctagaaatcatacgcggcaggaccaagcaacatggtcagttttctcttgcagtcgtcagc
ctgaacataacatccttgggattacgctccctcaaggagataagtgatggagatgtgataatttcaggaaacaaaaatttgtgctatgcaaat
acaataaactggaaaaaactgtttgggacctccggtcagaaaaccaaaattataagcaacagaggtgaaaacagctgcaaggccacag
gccaggtctgccatgccttgtgctcccccgagggctgctggggcccggagcccagggactgcgtctcttgccggaatgtcagccgagg
cagggaatgcgtggacaagtgcaaccttctggagggtgagccaagggagtttgtggagaactctgagtgcatacagtgccacccagag
tgcctgcctcaggccatgaacatcacctgcacaggacggggaccagacaactgtatccagtgtgcccactacattgacggcccccactg
cgtcaagacctgcccggcaggagtcatgggagaaaacaacaccctggtctggaagtacgcagacgccggccatgtgtgccacctgtg
ccatccaaactgcacctacggatgcactgggccaggtcttgaaggctgtccaacgaatgggcctaagatcccgtccatcgccactggga
tggtgggggccctcctcttgctgctggtggtggccctggggatcggcctcttcatgcgaaggcgccacatcgttcggaagcgctgagaa
ttc

(B) Protein sequence of del-hEGFRvIII (SEQ ID NO: 18)

Met R P S G T A G A A L L A L L A A L C P A S R A L E E K K G N Y V V T D H G S C
V R A C G A D S Y E Met E E D G V R K C K K C E G P C R K V C N G I G I G E F K D S
L S I N A T N I K H F K N C T S I S G D L H I L P V A F R G D S F T H T P P L D P Q E L
D I L K T V K E I T G F L L I Q A W P E N R T D L H A F E N L E I I R G R T K Q H G Q
F S L A V V S L N I T S L G L R S L K E I S D G D V I I S G N K N L C Y A N T I N W K
K L F G T S G Q K T K I I S N R G E N S C K A T G Q V C H A L C S P E G C W G P E P
R D C V S C R N V S R G R E C V D K C N L L E G E P R E F V E N S E C I Q C H P E C
L P Q A Met N I T C T G R G P D N C I Q C A H Y I D G P H C V K T C P A G V Met G E
N N T L V W K Y A D A G H V C H L C H P N C T Y G C T G P G L E G C P T N G P K I
P S I A T G Met V G A L L L L L V V A L G I G L F Met R R R H I V R K R Stop

BISPECIFIC ANTIBODY MOLECULES WITH ANTIGEN-TRANSFECTED T-CELLS AND THEIR USE IN MEDICINE

The present invention relates to a bispecific (monoclonal) antibody molecule with a first binding domain binding an antigen on CD8+ T-cells that does not naturally occur in and/or on CD8+ T-cells and a second binding domain binding to a tumor specific antigen naturally occurring on the surface of a tumor cell. Furthermore, a nucleic acid sequence encoding a (monoclonal) bispecific antibody molecule of the invention is provided. Further aspects of the invention are vectors and host cells comprising said nucleic acid sequence, a process for the production of the (bispecific) antibody molecule of the invention and a medicament/composition comprising said (bispecific) antibody molecule. Moreover, the invention relates to transduced CD8+ T-cells comprising an antigen which does not naturally occur in and/or on $CD8^+$ T-cells and/or a T-cell receptor. The invention also provides the use of said (bispecific) antibody molecules in a method for the treatment of particular diseases as well as a pharmaceutical composition/medicament comprising said (bispecific) antibody molecules, wherein said (bispecific) antibody molecule(s) is (are) to be administered in combination with transduced CD8+ T-cells comprising an antigen which does not naturally occur in and/or on CD8+ T-cells and/or a T-cell receptor in a specific treatment regimen. The invention also provides a method for the treatment of particular diseases and a kit comprising the (bispecific) antibody molecule of the invention.

BACKGROUND OF THE INVENTION

The transfusion of T-cells (i.e. T lymphocytes), referred to as adoptive T-cell therapy, has been tested for the treatment of cancer and chronic infections. Adoptive T-cell therapy has the potential to enhance antitumor immunity, augment vaccine efficacy and limit graft-versus-host disease. Adoptive T-cell therapy uses as a cell source, inter alia, cytotoxic T-cells (CTLs), or tumor-infiltrating lymphocytes (TILs). Bispecific antibodies can be used to "arm" (activated) T-cells in order to form a bridge between them and a surface antigen on tumor cells. Bispecific antibodies that target on one side a surface marker/antigen on tumor cells and on the other side to another marker/antigen that is naturally/endogenously expressed in or on cells are described, for example, in Glorius et al., Blood 116 (2010), 1173; Rothe et al., Blood 118 (2011), 1585; Zhengxing et al., Blood 111 (2007), 2211-2219, Herrmann et al., Cancer Research 68 (2008), 1221-1227; Singer et al., Journal of Immunotherapy 33 (2010), 599-608; Brandi et al., Experimental Hematology 27 (1999), 1264-1270; James et al., European Journal of Cancer 35 (1999), S343-S344; Chen et al., Clinical Cancer Research 1 (1995), 1319-1325; Valera et al., Molecular Cancer Therapeutics 9 (2010), 1872-1883; Gelderman et al., European Journal of Immunology 36 (2006), 977-984; Schweizer et al., Cancer Immunology Immunotherapy 51 (2002), 621-629; Friedman et al., Biotechnology and Applied Biochemistry 54 (2009), 121-131; Schaefer et al., Cancer Cell 20 (2011), 472-486 and Kazuhiko et al., International Journal of Molecular Medicine 25 (2010), 209-215.

Antigen-specific cytotoxic T-cells (CTLs) are known to have the capacity to kill human cancer cells, as shown by tumor regression after adoptive transfer of ex-vivo expanded tumor infiltrating lymphocytes (TILs) or of T-cell receptor gene-transfected T-cells to patients with melanoma (Leen et al., Annu. Rev. Immunol. 115 (2007), 98-104). An alternative known approach is the use of bispecific antibodies in order to redirect large numbers of endogenous T-cells. These bispecific antibodies, some formats of which are called BiTE (for "bispecific T-cell engager") were constructed in such a way that they target on one side the surface marker CD3 (that naturally occurs/endogenously expressed on T-cells) and on the other side a surface antigen on tumor cells (that is naturally/endogenously expressed on the surface of tumor cells). Moreover, it has been shown in previous work that anti-CD3 anti-target antigen bispecific antibodies of this particular design had an exceptionally high potency and could engage CD8+ T-cells and CD4+ T-cells for lysis of cancer cells at very low effector to target (E:T) ratios. Two BiTE antibodies are currently in clinical trials: Blinatumomab (also known as MT103) is bispecific for CD3 and CD19. It is currently being tested in a phase I trial in patients with late stage, relapsed non-Hodgkin's lymphoma (NHL) (Bargou et al., Science 321 (2008), 974-977) and in a phase II trial in patients with B-precursor acute lymphoblastic leukemia (B-ALL) (Topp et al., Blood 112 (2008), 1926). The second BiTE antibody in phase I trial is MT-110 (Micromet Inc), which targets the pan-carcinoma-associated antigen, epithelial cell adhesion molecule (EpCAM or CD326) and CD3 (Brischwein et al., Mol. Immunol. 43 (2006), 1129-1143). One bispecific antibody (catumaxumab [Removab®]; bispecific against CD3 and human EpCAM) has been approved for marketing in Europe in 2009.

In vitro and in mouse model systems bispecific antibodies are capable of connecting a T-cell and a cancer cell by simultaneously binding CD3 and a target antigen, which triggers T-cell activation involving cytotoxic granule fusion and transient cytokine and granzyme release. However, the activation of a large number of T-cells (independent of T-cell antigen specificity) and/or the bystander effect of tumor cell lysis leads to serious problems when using such bispecific antibodies, e.g., as part of a therapeutic regimen in humans.

One such problem is the so called "cytokine release syndrome (CRS)", which in the mouse model system normally causes no effects but can have catastrophic effects in humans (Suntharalingam et al., The New England Journal of Medicine 355 (2006), 1018-1028). CRS includes headache, myalgias, nausea, diarrhea, erythema, vasodilatation, and hypotension. The most severe form leads to pulmonary infiltrates, lung injury, renal failure, and disseminated intravascular coagulation (Suntharalingam et al., The New England Journal of Medicine 355 (2006), 1018-1028). Even if CRS is not associated with bispecific antibody application, a significant number of other side effects (over 80% of toxicities of grade three or higher) has been seen after bispecific antibody administration (Topp et al., Journal of Clinical Oncology 29 (2011), 2093-2098). Such side effects are ascribed to the T-cell engagement as well and include lymphopenia, blood chemistry changes and eurologic symptoms.

Due to the high side effect profile of the bispecific antibodies it is not possible to use antibody formats with a long half-life, since in case of a CRS event the long half-life is undesirable.

Therefore, the technical problem of the present invention was the provision of means and methods for the treatment of a malignant disease such as cancer of epithelial, endothelial or mesothelial origin and cancer of the blood by the induction of T-cell mediated immune response.

SUMMARY OF THE INVENTION

These above-mentioned means and methods for the treatment of a malignant disease such as cancer of epithelial, endothelial or mesothelial origin and cancer of the blood by the induction of T-cell mediated immune response should overcome the above mentioned disadvantages of the known bispecific antibody based therapies.

The solution to said technical problem is achieved by providing the embodiments characterized in the claims.

Figure 7:
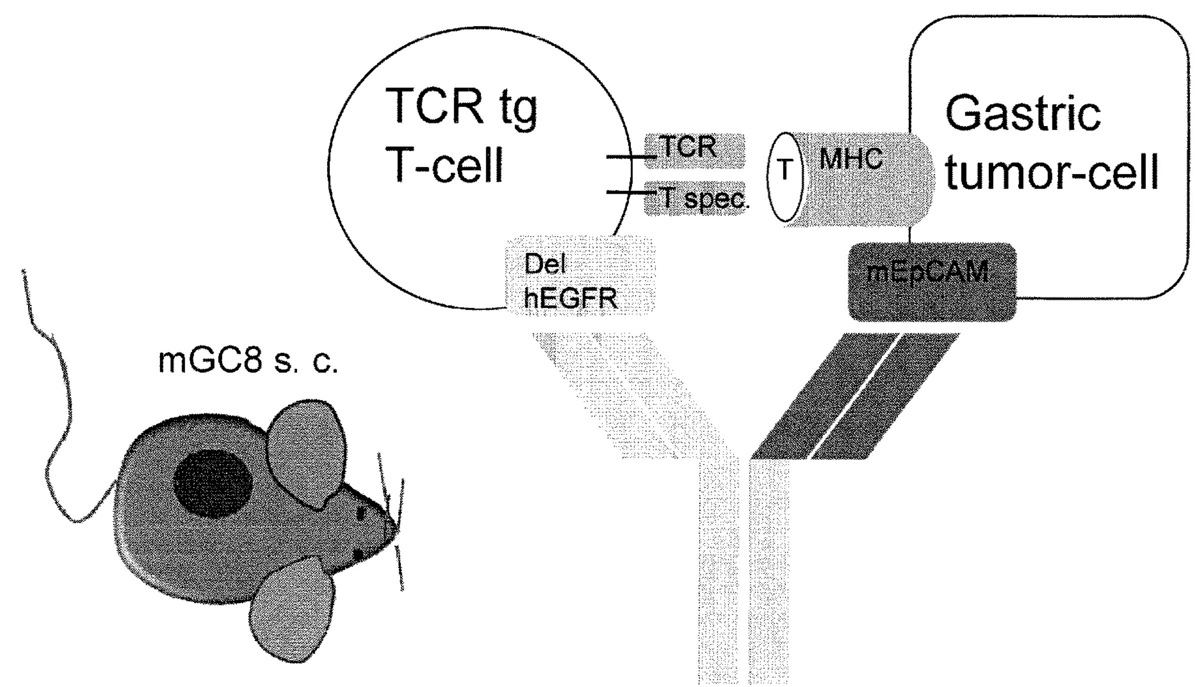
Figure 21:
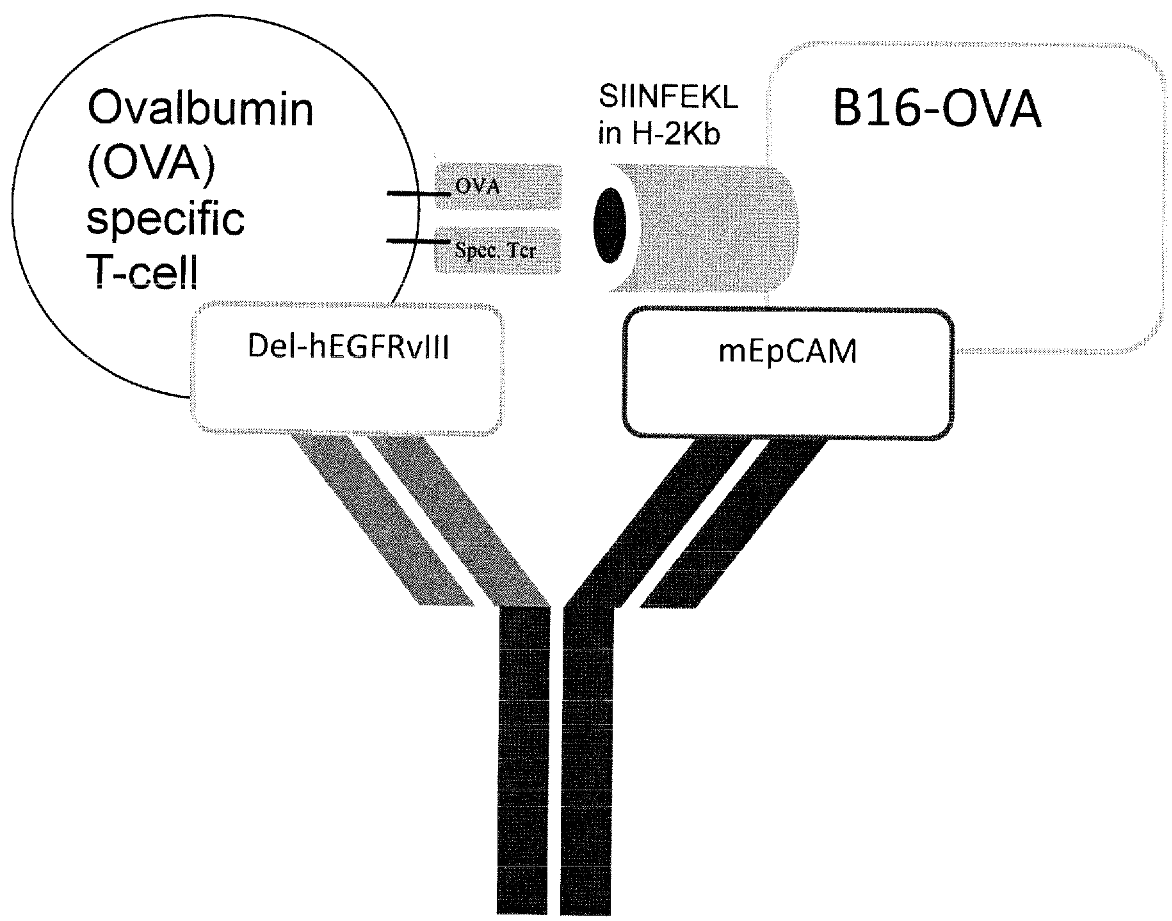

Accordingly, the present invention relates to the transduction of CD8+ T-cells with a marker protein that does not naturally occur in and/or on the surface of CD8+ T-cells and their targeted recruitment by a bispecific antibody molecule to the tumor (see FIGS. 7 and 21). In the context of the present invention the transduction of CD8+ T-cells can be performed by a retroviral system as described herein below. The present invention relates to a bispecific antibody molecule comprising a first binding domain specifically binding to an antigen on CD8+ T-cells that does not naturally occur in and/or on CD8+ T-cells and a second binding domain, binding to a tumor-specific antigen naturally occurring on the surface of a tumor cell, wherein said CD8+ T-cells have been transduced with an antigen that does not naturally occur in and/or on CD8+ T-cells. In the context of the present invention, the bispecific antibody molecule comprising a first binding domain specifically binding to an antigen on CD8+ T-cells that does not naturally occur in and/or on CD8+ T-cells and a second binding domain, binding to a tumor-specific antigen naturally occurring on the surface of a tumor cell, wherein said bispecific antibody molecule is a (monoclonal) antibody molecule. As shown in the appended examples, as a proof of the inventive concept, a bispecific antibody, wherein the first binding domain interacts with/binds to (human) EGFR (representing the antigen that does not naturally occur in or on T-cells (CD8+ T-cells) and the second binding domain interacts with/binds to EpCAM (representing a tumor specific antigen that naturally occurs on the surface of a tumor cell) was constructed. The treatment of tumors by the combination of this bispecific antibody and transduced tumor specific T-cells (CD8+ T-cells) expressing the del-(human) hEGFR protein significantly prolongs survival of the mice compared to control experiments (see FIGS. 12 and 14). Accordingly, it was surprisingly found that T-cells (CD8+ T-cells) that were transduced with an antigen (as in the appended Examples (as a proof of concept) by the del-(human) hEGFR protein sequence as shown in SEQ ID NO: 12 (as encoded by the cDNA sequence shown in SEQ ID NO: 11)) that does not naturally occur in and/or on the surface of these cells, can be specifically recruited by the use of a bispecific antibody molecule that binds via a first binding domain ((human) hEGFR) to an antigen that does not naturally occur in and/or on T-cells (CD8+ T-cells) which has been introduced into said T-cells (CD8 T-cells) and via a second binding domain to a tumor-specific antigen (EpCAM) naturally occurring on the surface of a tumor cell.

In this context, the term "bispecific binding construct" as used herein relates specifically to a bispecific antibody molecule capable of binding to an antigen that is not naturally/endogenously expressed in or on CD8+ T-cells and capable of inducing elimination/lysis of target cells (via a second binding domain binding to a tumor-specific antigen naturally occurring (that is endogenously expressed) on the surface of a tumor cell). Binding of the antigen that does not naturally occur in and/or on CD8+ T-cells (e.g., antibody, antibody derivates or antibody fragments) through the bispecific binding construct (bispecific antibody molecule) brings tumor specific T-cells (CD8+ T-cells) into physical contact with the tumor cell (see FIGS. 7 and 21). Non-transduced or endogenous T-cells (CD8+ T-cells) remain unaffected by the bispecific binding construct (bispecific antibody molecule). Accordingly, the inventive bispecific antibody molecule has the ability to lyse target cells in vivo and/or in vitro. Corresponding target cells comprise cells expressing a surface molecule, which is recognized by the second (Ig-derived) binding domain of the inventive bispecific antibody molecules. Such surface molecules are characterized herein below.

Lysis of the target cell can be detected by methods known in the art. Accordingly, such methods comprise, inter alia, physiological in vitro assays. Such physiological assays may monitor cell death, for example by loss of cell membrane integrity (e.g. FACS based propidium Iodide assay, trypan Blue influx assay, photometric enzyme release assays (LDH), radiometric $^{51}$Cr release assay, fluorometric Europium release and CalceinAM release assays). Further assays comprise monitoring of cell viability, for example by photometric MTT, XTT, WST-1 and alamarBlue assays, radiometric $^{3}$H-Thd incorporation assay, clonogenic assay measuring cell division activity, and fluorometric Rhodamine$^{123}$ assay measuring mitochondrial transmembrane gradient. In addition, apoptosis may be monitored for example by FACS-based phosphatidylserin exposure assay, ELISA-based TUNEL test, caspase activity assay (photometric, fluorometric or ELISA-based) or analysing changed cell morphology (shrinking, membrane blebbing).

The term "binding to" as used in the context of the present invention defines a binding (interaction) of at least two "antigen-interaction-sites" with each other. The term "antigen-interaction-site" defines, in accordance with the present invention, a motif of a polypeptide which shows the capacity of specific interaction with a specific antigen or a specific group of antigens. Said binding/interaction is also understood to define a "specific recognition". The term "specifically recognizing" means in accordance with this invention that the antibody construct is capable of specifically interacting with and/or binding to at least two amino acids of each of the human target molecule as defined herein. Antibodies can recognize, interact and/or bind to different epitopes on the same target molecule. This term relates to the specificity of the antibody molecule, i.e., to its ability to discriminate between the specific regions of the human target molecule as defined herein. The specific interaction of the antigen-interaction-site with its specific antigen may result in an initiation of a signal, e.g. due to the induction of a change of the conformation of the antigen, an oligomerization of the antigen, etc. Thus, a specific motif in the amino acid sequence of the antigen-interaction-site and the antigen bind to each other as a result of their primary, secondary or tertiary structure as well as the result of secondary modifications of said structure.

The term "specific interaction" as used in accordance with the present invention means that the bispecific binding construct (bispecific antibody molecule) of the invention does not or does not essentially cross-react with (poly) peptides of similar structures. Accordingly, the bispecific construct of the invention specifically binds to/interacts with tumor markers, cell surface markers, antigens which do not naturally occur in and/or on CD8+ T-cells and is capable, due to its second, (Ig-derived) domain to interact with specific, selected other compounds, antigens, cell-surface markers, tumor markers, etc that do naturally occur on the surface of tumor cells. Specific examples of such molecules against which said first and second, Ig-derived domain is directed are given herein below.

Cross-reactivity of a panel of constructs under investigation may be tested, for example, by assessing binding of said panel of bispecific antibody constructs under conventional conditions (see, e.g., Harlow and Lane, Antibodies: A Laboratory Manual, Cold Spring Harbor Laboratory Press, (1988) and Using Antibodies: A Laboratory Manual, Cold Spring Harbor Laboratory Press, (1999)) to the (poly)peptide of interest as well as to a number of more or less (structurally and/or functionally) closely related (poly)peptides. Only those constructs (i.e. antibodies, (bispecific) scFvs and the like) that bind to the (poly) peptide/protein of interest but do not or do not essentially bind to any of the other (poly) peptides which are expressed by the same tissue as the (poly) peptide of interest, e.g. by the cells of the tumor tissue, are considered specific for the (poly) peptide/protein of interest and selected for further studies in accordance with the method provided herein. These methods may comprise, inter alia, binding studies, blocking and competition studies with structurally and/or functionally closely related molecules. These binding studies also comprise FACS analysis, surface plasmon resonance (SPR, e.g. with BIAcore®), analytical ultracentrifugation, isothermal titration calorimetry, fluorescence anisotropy, fluorescence spectroscopy or by radiolabeled ligand binding assays. Furthermore, physiological assays, like cytotoxic assays and assays mentioned above may be performed. Accordingly, examples for the specific interaction of an antigen-interaction-site with a specific antigen may comprise the specificity of a ligand for its receptor. Said definition particularly comprises the interaction of ligands which induce a signal upon binding to its specific receptor. Examples for corresponding ligands comprise cytokines which interact/bind with/to its specific cytokine-receptors. Also particularly comprised by said definition is the binding of an antigen-interaction-site to antigens such as antigens of the selectin family, integrins and of the family of growth factors like EGF. Another example for said interaction, which is also particularly comprised by said definition, is the interaction of an antigenic determinant (epitope) with the antigenic binding site of an antibody.

The term “binding to” does not only relate to a linear epitope but may also relate to a conformational epitope, a structural epitope or a discontinuous epitope consisting of two regions of the human target molecules or parts thereof. In the context of this invention, a conformational epitope is defined by two or more discrete amino acid sequences separated in the primary sequence which comes together on the surface of the molecule when the polypeptide folds to the native protein (Sela, *Science* 166 (1969), 1365 and Laver, *Cell* 61 (1990), 553-536). Moreover, the term “binding to” is interchangeably used in the context of the present invention with the term “interacting with”.

Accordingly, specificity can be determined experimentally by methods known in the art and methods as described herein. Such methods comprise, but are not limited to Western Blots, ELISA-, RIA-, ECL-, IRMA-tests and peptide scans.

The term (Ig-derived) “first binding domain” relates to an “immunoglobulin-derived domain”, specifically to an antibody or fragments thereof, to single chain antibodies, to synthetic antibodies, to antibody fragments, such as Fab, a F(ab$_2$)', Fv or scFv fragments etc, or a chemically modified derivative of any of these. These antibody molecules may be derived from different species or may be of chimeric origin. In the context of the present invention (as illustrated in the appended examples), said (Ig-derived) first domain comprised in the bispecific antibody molecule of the invention can be a (monoclonal) antibody to which a second (Ig-derived) “binding domain” is fused.

The term (Ig-derived) “second binding domain” relates to an immunoglobulin-derived domain, specifically to an antibody or fragments thereof, to single chain antibodies, to synthetic antibodies, to antibody fragments, such as Fab, a F(ab$_2$)', Fv or scFv fragments etc, or a chemically modified derivative of any of these. These antibody molecules may be derived from different species or may be of chimeric origin. In the context of the present invention (as illustrated in the appended examples), said (Ig-derived) second domain comprised in the bispecific antibody molecule of the invention can be a scFv.

The bispecific antibody molecules according to the invention are (monoclonal) bispecific antibodies that have binding specificities for at least two different sites and can be of any format. A wide variety of recombinant antibody formats have been developed in the recent past, e.g. bivalent, trivalent or tetravalent bispecific antibodies. Examples include the fusion of an IgG antibody format and single chain domains (for different formats see e.g. Coloma, M. J., et al., Nature Biotech 15 (1997), 159-163; WO 2001/077342; Morrison, S. L., Nature Biotech 25 (2007), 1233-1234; Holliger, P., et. al, Nature Biotech. 23 (2005), 1126-1136; Fischer, N., and Léger, O., Pathobiology 74 (2007), 3-14; Shen, J., et. al., J. Immunol. Methods 318 (2007), 65-74; Wu, C., et al., Nature Biotech. 25 (2007), 1290-1297). The bispecific antibody or fragment herein also includes bivalent, trivalent or tetravalent bispecific antibodies described in WO 2009/080251; WO 2009/080252; WO 2009/080253; WO 2009/080254; WO 2010/112193; WO 2010/115589; WO 2010/136172; WO 2010/145792; WO 2010/145793 and WO 2011/117330.

“Antibodies” of the present invention have two or more binding domains and are bispecific. That is, the antibodies may be bispecific even in cases where there are more than two binding domains (i.e. that the antibody is trivalent or multivalent). Bispecific antibodies of the invention include, for example, multivalent single chain antibodies, diabodies and triabodies, as well as antibodies having the constant domain structure of full length antibodies to which further antigen-binding domains (e.g., single chain Fv, a VH domain and/or a VL domain, Fab, or (Fab)2,) are linked via one or more peptide-linkers. The antibodies can be full length from a single species, or be chimerized or humanized. For an antibody with more than two antigen binding domains, some binding domains may be identical, as long as the protein has binding domains for two different antigens.

The term “valent” as used within the current application denotes the presence of a specified number of binding domains in an antibody molecule. As such, the terms “bivalent”, “tetravalent”, and “hexavalent” denote the presence of two binding domains, four binding domains, and six binding domains, respectively, in an antibody molecule. The bispecific antibodies according to the invention are at least “bivalent” and may be “trivalent” or “multivalent” (e.g. “tetravalent” or “hexavalent”). Preferably the bispecific antibody according to the invention is bivalent, trivalent or tetravalent. Accordingly, in the context of the present invention said bispecific antibody is bivalent. In the context of the present invention said bispecific antibody is trivalent. In the context of the present invention said bispecific antibody is tetravalent.

As mentioned above (and illustrated in FIG. 1), the bispecific antibody molecule of the invention, most preferably, comprises an (Ig-derived) second domain which can be a scFv. Accordingly, in an illustrative embodiment of the present invention, for the proof of concept, a bispecific antibody molecule is provided with one specificity for (human) EGFR (via the first binding domain) and a further specificity which is mediated by a second scFv, directed against/capable of interacting with a further molecule/compound. These further molecules/compounds may comprise cell surface molecules, tumor markers, tumor antigens and the like. Such further compounds/molecules are exemplified herein below.

Accordingly, bispecific binding molecules in the context of the present invention may relate to an antibody molecule comprising two antibody derived binding domains, wherein one binding domain can be a scFv. One of said binding domains consists of variable regions (or parts thereof) of an antibody, antibody fragment or derivate thereof, capable of specifically binding to/interacting with a (human) target molecule 1 that does not naturally occur in and/or on CD8+ T-cells (as defined herein below). The second binding domain consists of variable regions (or parts thereof) of an antibody, antibody fragment or derivative thereof, capable of specifically binding to/interacting with another (human) antigen (target molecule 2) as defined herein below. Accordingly, said second binding domain is, in accordance with this invention, the (Ig-derived) second domain recited above which comprises an antigen-interaction-site with specificity for a cell surface molecule naturally occurring on the surface of a tumor cell or a tumor specific marker (antigen) naturally occurring on the surface of a tumor cell. Said two domains/regions in the bispecific antibody molecule are preferably covalently connected to one another. This connection can be effected either directly (domain 1 [specific for a (human) target molecule 1 that does not naturally occur in or on CD8+ T-cells, comprising CDR-regions or CDR-regions and framework regions as defined above]-domain 2 [specific for a cell surface molecule and/or a tumor specific marker] or domain 1 [specific for a cell surface molecule and/or a tumor specific marker]-domain 2 [specific for a (human) target molecule 1 that does not naturally occur in and/or on CD8+ T-cells, comprising CDR-regions or CDR-regions and framework regions as defined above]) or through an additional polypeptide linker sequence (domain1-linker sequence-domain2). In the event that a linker is used, this linker is in the context of the present invention of a length and sequence sufficient to ensure that each of the first and second domains can, independently from each other, retain their differential binding specificities. In the context of the present invention the additional polypeptide linker sequence can also be a fragment of an antibody itself which may be for example the Fc part or one or more constant domains of an antibody.

In the context of the present invention, binding domain 1 can also be part of an antibody arm 1 and binding domain 2 can also be part of an antibody arm 2, or vice versa, wherein the two antibody arms are connected via an interface. The antibody arm 1 consists of variable regions (or parts thereof) of an antibody, antibody fragment or derivate thereof, capable of specifically binding to/interacting with a (human) target molecule 1 that does not naturally occur in or on CD8+ T-cells as defined herein below. The antibody arm 2 consists of variabale regions (or parts thereof) of an antibody, antibody fragment or derivative thereof capable of specifically binding to/interacting with a cell surface molecule naturally occurring on the surface of a tumor cell or a tumor specific antigen naturally occurring on the surface of a tumor cell. The "interface" comprises those contact amino acid residues (or other non-amino acid groups such as, e.g., carbohydrate groups) in the first antibody arm which interact with one or more "contact" amino acid residues (or other non-amino acid groups) in the interface of the second antibody arm. The preferred interface is a domain of an immunoglobulin such as a constant domain (or regions thereof) of the antibody's heavy chains, wherein the binding/interaction via the interface provides for the heterodimerization of the two antibody arms (see e.g. Ridgway, J. B., et al., Protein Eng. 9 (1996), 617-621; WO 96/027011; Merchant, A. M., et al., Nature Biotech. 16 (1998), 677-681; Atwell, S., et al., J. Mol. Biol. 270 (1997), 26-35; EP 1 870 459 A1; WO 2007/147901; WO 2009/089004(A1) and WO 2010/129304).

Antibodies, antibody constructs, bispecific antibody molecules, antibody fragments, antibody derivatives (all being Ig-derived) to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook (1989), loc. cit. The term "Ig-derived domain" particularly relates to (poly) peptide constructs comprising at least one CDR. Fragments or derivatives of the recited Ig-derived domains define (poly) peptides which are parts of the above antibody molecules and/or which are modified by chemical/biochemical or molecular biological methods. Corresponding methods are known in the art and described inter alia in laboratory manuals (see Sambrook et al., Molecular Cloning: A Laboratory Manual; Cold Spring Harbor Laboratory Press, 2nd edition (1989) and 3rd edition (2001); Gerhardt et al., Methods for General and Molecular Bacteriology ASM Press (1994); Lefkovits, Immunology Methods Manual: The Comprehensive Sourcebook of Techniques; Academic Press (1997); Golemis, Protein-Protein Interactions: A Molecular Cloning Manual Cold Spring Harbor Laboratory Press (2002)).

The term "CDR" as employed herein relates to "complementary determining region", which is well known in the art. The CDRs are parts of immunoglobulins that determine the specificity of said molecules and make contact with a specific ligand. The CDRs are the most variable part of the molecule and contribute to the diversity of these molecules. There are three CDR regions CDR1, CDR2 and CDR3 in each V domain. CDR-H depicts a CDR region of a variable heavy chain and CDR-L relates to a CDR region of a variable light chain. VH means the variable heavy chain and VL means the variable light chain. The CDR regions of an Ig-derived region may be determined as described in Kabat "Sequences of Proteins of Immunological Interest", 5th edit. NIH Publication no. 91-3242 U.S. Department of Health and Human Services (1991); Chothia J. Mol. Biol. 196 (1987), 901-917 or Chothia Nature 342 (1989), 877-883.

Accordingly, in the context of the present invention, the antibody molecule like the bispecific antibody described herein above is selected from the group consisting of a full antibody (immunoglobulin, like an IgG1, an IgG2, an IgG2b, an IgG3, an IgG4, an IgA, an IgM, an IgD or an IgE), F(ab)-, Fab'-SH-, Fv-, Fab'-, $F(ab')_2$-fragment, a chimeric antibody, a CDR-grafted antibody, a fully human antibody, a bivalent antibody-construct, an antibody-fusion protein, a synthetic antibody, bivalent single chain antibody, a trivalent single chain antibody and a multivalent single chain antibody.

The term "fully-human antibody" as used herein refers to an antibody which comprises human immunoglobulin protein sequences only. A fully human antibody may contain murine carbohydrate chains if produced in a mouse, in a mouse cell or in a hybridoma derived from a mouse cell. Similarly, "mouse antibody" or "murine antibody" refers to an antibody which comprises mouse (murine) immunoglobulin protein sequences only. Alternatively, a "fully-human antibody" may contain rat carbohydrate chains if produced in a rat, in a rat cell, in a hybridoma derived from a rat cell. Similarly, the term "rat antibody" refers to an antibody that comprises rat immunoglobulin sequences only. Fully-human antibodies may be produced, for example, by phage display which is a widely used screening technology which enables production and screening of fully human antibodies. Also phage antibodies can be used in context of this invention. Phage display methods are described, for example, in U.S. Pat. Nos. 5,403,484, 5,969,108 and 5,885,793. Another technology which enables development of fully-human antibodies involves a modification of mouse hybridoma technology. Mice are made transgenic to contain the human immunoglobulin locus in exchange for their own mouse genes (see, for example, U.S. Pat. No. 5,877,397).

The term antibody as used herein, also comprises chimeric antibodies. The term "chimeric antibodies" refers to an antibody which comprises a variable region of a human or non-human species fused or chimerized with an antibody region (e.g., constant region) from another, human or non-human species (e.g., mouse, horse, rabbit, dog, cow, chicken).

The term antibody also relates to recombinant human antibodies, heterologous antibodies and heterohybrid antibodies. The term "recombinant human antibody" includes all human sequence antibodies that are prepared, expressed, created or isolated by recombinant means, such as antibodies isolated from an animal (e.g., a mouse) that is transgenic for human immunoglobulin genes; antibodies expressed using a recombinant expression vector transfected into a host cell, antibodies isolated from a recombinant, combinatorial human antibody library, or antibodies prepared, expressed, created or isolated by any other means that involves splicing of human immunoglobulin gene sequences to other DNA sequences. Such recombinant human antibodies have variable and constant regions (if present) derived from human germline immunoglobulin sequences. Such antibodies can, however, be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

A "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

The term "heterohybrid antibody" refers to an antibody having light and heavy chains of different organismal origins. For example, an antibody having a human heavy chain associated with a murine light chain is a heterohybrid antibody. Examples of heterohybrid antibodies include chimeric and humanized antibodies.

The term antibody also relates to humanized antibodies. "Humanized" forms of non-human (e.g. murine or rabbit) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Often, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Furthermore, humanized antibody may comprise residues, which are found neither in the recipient antibody nor in the imported CDR or framework sequences. These modifications are made to further refine and optimize antibody performance. In general, the humanized antibody will comprise substantially all of at least one, and typically two variable domains, in which all or substantially all of the CDR regions correspond to those of a non-human immunoglobulin and all or substantially all of the FR regions are those of a human immunoglobulin consensus sequence. The humanized antibody may also comprise at least a portion of an immunoglobulin constant region (Fc), typically that of a human immunoglobulin. For further details, see: JonesNature 321 (1986), 522-525; Reichmann Nature 332 (1998), 323-327 and Presta Curr Op Struct Biol 2 (1992), 593-596.

A popular method for humanization of antibodies involves CDR grafting, where a functional antigen-binding site from a non-human 'donor' antibody is grafted onto a human 'acceptor' antibody. CDR grafting methods are known in the art and described, for example, in U.S. Pat. Nos. 5,225,539, 5,693,761 and 6,407,213. Another related method is the production of humanized antibodies from transgenic animals that are genetically engineered to contain one or more humanized immunoglobulin loci which are capable of undergoing gene rearrangement and gene conversion (see, for example, U.S. Pat. No. 7,129,084).

Accordingly, in context of the present invention, the term "antibody" relates to full immunoglobulin molecules as well as to parts of such immunoglobulin molecules. Furthermore, the term relates, as discussed above, to modified and/or altered antibody molecules. The term also relates to recombinantly or synthetically generated/synthesized antibodies. The term also relates to intact antibodies as well as to antibody fragments thereof, like, separated light and heavy chains, Fab, Fab/c, Fv, Fab', F(ab')2. The term "antibody" also comprises bifunctional antibodies, trifunctional antibodies, fully-human antibodies, chimeric antibodies, humanized antibodies and antibody constructs, like single chain Fvs (scFv) or antibody-fusion proteins.

"Single-chain Fvs" or "scFv" antibody fragments have, in the context of the present invention, the $V_H$ and $V_L$ domains of an antibody, wherein these domains are present in a single polypeptide chain. Generally, the scFv polypeptide further comprises a polypeptide linker between the $V_H$ and $V_L$ domains which enables the scFv to form the desired structure for antigen binding. Techniques described for the production of single chain antibodies are described, e.g., in Plückthun in The Pharmacology of Monoclonal Antibodies, Rosenburg and Moore eds. Springer-Verlag, N.Y. 113 (1994), 269-315.

A "Fab fragment" as used herein is comprised of one light chain and the $C_H1$ and variable regions of one heavy chain. The heavy chain of a Fab molecule cannot form a disulfide bond with another heavy chain molecule.

An "Fc" region contains two heavy chain fragments comprising the $C_H2$ and $C_H3$ domains of an antibody. The two heavy chain fragments are held together by two or more disulfide bonds and by hydrophobic interactions of the $C_H3$ domains.

A "Fab' fragment" contains one light chain and a portion of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a $F(ab')_2$ molecule.

A "$F(ab')_2$ fragment" contains two light chains and two heavy chains containing a portion of the constant region between the $C_H1$ and $C_H2$ domains, such that an interchain disulfide bond is formed between the two heavy chains. A $F(ab')_2$ fragment thus is composed of two Fab' fragments that are held together by a disulfide bond between the two heavy chains.

The "Fv region" comprises the variable regions from both the heavy and light chains, but lacks the constant regions.

It is of note that the bispecific antibody molecule of the invention may comprise, in addition to the herein defined first (Ig-derived) domain and the (Ig-derived) second domain (an) additional domain(s), e.g. for the isolation and/or preparation of recombinantly produced constructs.

It is of note that, in accordance with this invention, not only the above described first domain which specifically interacts with/binds to a (human) antigen on CD8+ T-cells that does not naturally occur in and/or on CD8+ T-cells of the inventive molecule or construct (i.e., the bispecific antibody molecule described herein) may be modified. It is also envisaged that the (Ig-derived) first domain, (Ig-derived) second domain and/or (a) connecting linker-region(s) is (are) modified, for example a humanized antibody, a CDR grafted antibody or a fully human antibody.

"Humanization approaches" are well known in the art and in particular described for antibody molecules, e.g. Ig-derived molecules. The term "humanized" refers to humanized forms of non-human (e.g., murine) antibodies or fragments thereof (such as Fv, Fab, Fab', F(ab'), scFvs, or other antigen-binding partial sequences of antibodies) which contain some portion of the sequence derived from non-human antibody. Humanized antibodies include human immunoglobulins in which residues from a complementary determining region (CDR) of the human immunoglobulin are replaced by residues from a CDR of a non-human species such as mouse, rat or rabbit having the desired binding specificity, affinity and capacity. In general, the humanized antibody will comprise substantially all of at least one, and generally two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin; see, inter alia, Jones et al., Nature 321 (1986), 522-525, Presta, Curr. Op. Struct. Biol. 2 (1992), 593-596. Methods for humanizing non-human antibodies are well known in the art. Generally, a humanized antibody has one or more amino acids introduced into it from a source which is non-human still retain the original binding activity of the antibody. Methods for humanization of antibodies/antibody molecules are further detailed in Jones et al., Nature 321 (1986), 522-525; Reichmann et al., Nature 332 (1988), 323-327; and Verhoeyen et al., Science 239 (1988), 1534-1536. Specific examples of humanized antibodies, e.g. antibodies directed against EpCAM, are known in the art, see e.g. (LoBuglio, Proceedings of the American Society of Clinical Oncology Abstract (1997), 1562 and Khor, Proceedings of the American Society of Clinical Oncology Abstract (1997), 847).

Accordingly, in the context of this invention, in particular bispecific antibody molecules are provided, which are humanized and can successfully be employed in pharmaceutical compositions. In the context of the invention, the herein described (humanized) bispecific antibody molecules can be employed in a kit as defined herein below.

In the context of the present invention, the (Ig-derived) first domain of the herein described bispecific antibody molecule comprise an antigen-interaction-site with specificity for an antigen that does not naturally occur in and/or on CD8+ T-cells.

The term "antigen that dries not naturally occur in and/or on CD8+ T-cells" as used herein, relates to molecules which are incorporated into the CD8+ T-cells, which are naturally not presented in and/or on the surface of CD8+ T-cells and which are not (endogenously) expressed in or on normal (non-transduced) CD8+ T-cells. Thus, the antigen/marker that does not naturally occur in and/or on CD8+ T cells is artificially introduced into CD8+ T cells. In the context of the present invention said CD8+ T-cells are isolated/obtained from a subject to be treated as defined herein. In the context of the present invention, the antigen peptides that naturally occurs/that is endogenously expressed on a T-cell receptor of a CD8+ T-cells is excluded from the above mentioned term "antigen that does not naturally occur on CD8+ T-cells". Accordingly, these molecules which are artificially introduced and subsequently presented in and/or on the surface of said CD8+ T-cells comprise domains or epitopes accessible (in vitro or in vivo) to (Ig-derived) binding domains, preferably antibodies, antibody fragments or derivatives that do not naturally occur in and/or on CD8+ T-cells. In the context of the present invention, these artificially introduced molecules are presented in and/or on the surface of said CD8+ T-cells after (retroviral) transduction as described herein below.

In the context of the present invention, the term "antigen that does not naturally occur in and/or on CD8+ T-cells" refers to an antigen/marker which does not naturally occur/which is not endogenously expressed in and/or on CD8+ T-cells with more than 500, 550, 600, 650, 700, 750, 800, 850, 900, 950 or 1000 antigen molecules/per CD8+ T-cell. Thus, the antigen/marker does not occur/is not endogenously expressed in and/or on CD8+ T-cells in more than 1.0, 1.1, 1.2, 1.3, 1.4, 1.5, 1.6, 1.7, 1.8, 1.9 or 2.0‰ (promille) of a population of normal (non-transduced) CD8+ T-cells. The presence and amount of an antigen/marker that naturally occurs in and/or on CD8+ T-cells can be monitored by methods known in the art, such as FACS analysis, ELISA, confocal microscopy, analytical HPLC and the like.

Examples for these molecules comprise non-immunogenic proteins, preferably of human origin. Alternatively, said molecules may be either per se a functionally inert protein molecule or will be made functionally inert by gene recombination techniques known in the art (examples would be protein molecules wherein a deletion of the intracellular signalling domain (as exemplified in the appended Examples by the (human) EGFR without intracellular signalling domain, referring to the herein described del-hEGFR construct (SEQ ID NOs: 11 and 12)) or inactivating point mutations of the extracellular domain render the molecule functionally inert). Another example of a mutated (human) EGFR version is the del-hGFRvIII construct (SEQ ID NO: 17 as the DNA and SEQ ID NO: 18 as the (encoded) amino acid sequence) as used in the appended examples. hEG- FRvIII is a mutant of human epidermal growth factor receptor found in glioblastoma, and in carcinoma of the breast, ovary and lung. The mutant receptor has a deletion in its extracellular domain (Lorimer et al., Proc. Natl. Acad. Sci USA 93:14815-14820 (1996)).

Examples of markers which fulfill these above mentioned criteria are given herein below and comprise, but are not limited to cripto (cryptic family protein), members of the CD (cluster of differentiation)-family (non T-cell), EGFR or TSH-R.

In the context of the present invention, (a) bispecific antibody molecule(s) described herein binds to an antigen that does not naturally occur in and/or on CD8+ T-cells selected from the group consisting of cripto (cryptic family protein), members of the CD (cluster of differentiation)-family (non T-cell), EGFR and TSH-R. Accordingly, the bispecific antibody molecule(s) described herein interacts with/binds to members of the CD-family that (exclusively) do not naturally occur in and/or on T-cells (CD8+ T-cells) (as it is addressed by the term "non T-cell"), cripto, EGFR or TSH-R. In the context of the present invention the bispecific antibody molecule(s) described herein interacts with/binds to members of the CD-family that are not endogenously expressed in and/or on the surface of T-cells (CD8+ T-cells) (as it is addressed by the term "non T-cell"), cripto, EGFR or TSH-R.

The sequence(s) of the (human) members of the cripto (cryptic family protein), members of the CD (cluster of differentiation)-family (non T-cell), EGFR or TSH-R are available in the UniProtKB/Swiss-Prot database and can be retrieved from uniprotorg/uniprot/?query=reviewed %3Ayes. These (protein) sequences also relate to annotated modified sequences. The present invention also provides techniques and methods wherein homologous sequences, and also genetic allelic variants and the like of the concise sequences provided herein are used. Preferably such "variants" and the like of the concise sequences herein are used. Preferably, such "variants" are genetic variants. The skilled person may easily deduce the relevant coding region of these (protein) sequences in these databank entries, which may also comprise the entry of genomic DNA as well as mRNA/cDNA.

The term "CD (cluster of differentation)-family (non T-cell)" as used herein in connection with the "antigen that does not naturally occur/that is not endogenously expressed in and/or on CD8+ T-cells" refers to any one of the CD sequences selected from the group consisting of CD9, CD10, CD11, CD12, CD13, CD14, CD15, CD16, CD17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD43, CD46, CD48, CD49, CD50, CD51, CD54, CD55, CD56, CD57, CD59, CD61, CD63, CD64, CD66, CD67, CD68, CD70, CD72, CD74, CD75, CD76, CD77, CD79, CD81, CD82, CD83, CD84, CD87, CD88, CD89, CD90, CD91, CD92, CD93, CD94, CD95, CD97, CD98, CD99, CD100, CD101, CD102, CD103, CD104, CD105, CD106, CD107, CD108, CD109, CD110, CD111, CD112, CD113, CD114, CD115, CD116, CD117, CD118, CD119, CD121, CD123, CD124, CD125, CD126, CD130, CD131, CD133, CD134, CD135, CD136, CD137, CD138, CD140, CD141, CD142, CD143, CD144, CD146, CD147, CD148, CD151, CD153, CD155, CD156, CD157, CD158, CD159, CD160, CD161, CD162, CD163, CD164, CD166, CD167, CD168, CD169, CD170, CD171, CD172, CD177, CD178, CD179, CD180, CD181, CD182, CD183, CD184, CD185, CD186, CD191, CD192, CD193, CD200, CD201, CD204, CD206, CD207, CD208, CD209, CD217, CD218, CD220, CD221, CD222, CD223, CD224, CD225, CD226, CD227, CD228, CD230, CD231, CD232, CD233, CD234, CD236, CD238, CD239, CD241, CD242, CD243, CD244, CD246, CD248, CD249, CD252, CD253, CD254, CD256, CD257, CD258, CD261, CD262, CD263, CD264, CD265, CD266, CD267, CD268, CD269, CD270, CD271, CD276, CD277, CD280, CD281, CD282, CD283, CD284, CD286, CD288, CD289, CD290, CD292, CD294, CD295, CD296, CD297, CD298, CD299, CD300, CD301, CD302, CD303, CD304, CD305, CD306, CD309, CD312, CD314, CD315, CD316, CD317, CD318, CD319, CD320, CD321, CD322, CD324, CD325, CD326, CD327, CD328, CD329, CD331, CD332, CD333, CD334, CD335, CD336, CD337, CD338, CD339, CD340, CD344, CD349, CD350, CD351, CD352, CD353, CD354, CD355, CD357, CD358, CD360, CD361, CD362 and CD363.

The sequence(s) of the (human) CD9 (CD9 antigen) can be obtained from the Swiss-Prot database entry P21926 (entry version 123, sequence version 4); the sequence(s) of the (human) CD10 (Neprilysin) can be obtained from the Swiss-Prot database entry P08473 (entry version 151, sequence version 2); the sequence(s) of the (human) CD11 (Integrin alpha-D) can be obtained from the Swiss-Prot database entry Q13349 (entry version 110, sequence version 2); the sequence(s) of the (human) CD13 (Aminopeptidase N) can be obtained from the Swiss-Prot database entry P15144 (entry version 145, sequence version 4); the sequence(s) of the (human) CD14 (Monocyte differentiation antigen CD14) can be obtained from the Swiss-Prot database entry P08571 (entry version 131, sequence version 2); the sequence(s) of the (human) CD16 (Fc-gamma receptor Mb) can be obtained from the Swiss-Prot database entry Q9ULV2 (entry version 51, sequence version 1); the sequence(s) of the (human) CD18 (Integrin beta-2) can be obtained from the Swiss-Prot database entry P05107 (entry version 162, sequence version 2); the sequence(s) of the (human) CD19 (B-lymphocyte antigen CD19) can be obtained from the Swiss-Prot database entry P15391 (entry version 128, sequence version 6); the sequence(s) of the (human) CD20 (B-lymphocyte antigen CD20) can be obtained from the Swiss-Prot database entry P11836 (entry version 118, sequence version 1); the sequence(s) of the (human) CD21 (Complement receptor type 2) can be obtained from the Swiss-Prot database entry P20023 (entry version 128, sequence version 2); the sequence(s) of the (human) CD22 (B-cell receptor CD22) can be obtained from the Swiss-Prot database entry P20273 (entry version 136, sequence version 2); the sequence(s) of the (human) CD23 (Low affinity immunoglobulin epsilon Fc receptor) can be obtained from the Swiss-Prot database entry P06734 (entry version 133, sequence version 1); the sequence(s) of the (human) CD24 (Signal transducer CD24) can be obtained from the Swiss-Prot database entry P25063 (entry version 106, sequence version 2); the sequence(s) of the (human) CD26 (Dipeptidyl peptidase 4) can be obtained from the Swiss-Prot database entry P27487 (entry version 140, sequence version 2); the sequence(s) of the (human) CD27 (CD27 antigen) can be obtained from the Swiss-Prot database entry P26842 (entry version 119, sequence version 2); the sequence(s) of the (human) CD29 (Integrin beta-1) can be obtained from the Swiss-Prot database entry P05556 (entry version 154, sequence version 2); the sequence(s) of the (human) CD30 (Tumor necrosis factor receptor superfamily member 8) can be obtained from the Swiss-Prot database entry P28908 (entry version 129; sequence version 1); the sequence(s) of the (human) CD31 (Platelet endothelial cell adhesion molecule) can be obtained from the Swiss-Prot database entry P16284 (entry version 146, sequence version 1); the sequence(s) of the (human) CD32 (Low affinity immunoglobulin gamma Fc region receptor II-b) can be obtained from the Swiss-Prot database entry P31994 (entry version 138, sequence version 2); the sequence(s) of the (human) CD33 (Myeloid cell surface antigen CD33) can be obtained from the Swiss-Prot database entry P20138 (entry version 130, sequence version 2); the sequence(s) of the (human) CD34 (Hematopoietic progenitor cell antigen CD34) can be obtained from the Swiss-Prot database entry P28906 (entry version 108, sequence version 2); the sequence(s) of the (human) CD35 (Complement receptor type 1) can be obtained from the Swiss-Prot database entry P17927 (entry version 131, sequence version 3); the sequence(s) of the (human) CD36 (Platelet glycoprotein 4) can be obtained from the Swiss-Prot database entry P16671 (entry version 133, sequence version 2); the sequence(s) of the (human) CD38 (ADP-ribosyl cyclase 1) can be obtained from the Swiss-Prot database entry P28907 (entry version 126, sequence version 2); the sequence(s) of the (human) CD39 (Ectonucleoside triphosphate diphosphohydrolase 1) can be obtained from the Swiss-Prot database entry P49961 (entry version 114, sequence version 1); the sequence(s) of the (human) CD40 (Tumor necrosis factor receptor superfamily member 5) can be obtained from the Swiss-Prot database entry P25942 (entry version 147, sequence version 1); the sequence(s) of the (human) CD41 (Integrin alpha-Hb) can be obtained from the Swiss-Prot database entry P08514 (entry version 158, sequence version 3); the sequence(s) of the (human) CD43 (Leukosialin) can be obtained from the Swiss-Prot database entry P16150 (entry version 110, sequence version 1); the sequence(s) of the (human) CD46 (Membrane cofactor protein) can be obtained from the Swiss-Prot database entry P15529 (entry version 145, sequence version 3); the sequence(s) of the (human) CD48 (CD48 antigen) can be obtained from the Swiss-Prot database entry P09326 (entry version 137, sequence version 2); the sequence(s) of the (human) CD49 (Integrin alpha-4) can be obtained from the Swiss-Prot database entry P13612 (entry version 128, sequence version 3); the sequence(s) of the (human) CD50 (Intercellular adhesion molecule 3) can be obtained from the Swiss-Prot database entry P32942 (entry version 128, sequence version 2); the sequence(s) of the (human) CD51 (Integrin alpha-V) can be obtained from the Swiss-Prot database entry P06756 (entry version 149, sequence version 2); the sequence(s) of the (human) CD54 (Intercellular adhesion molecule 1) can be obtained from the Swiss-Prot database entry P05362 (entry version 160, sequence version 2); the sequence(s) of the (human) CD55 (Complement decay-accelerating factor) can be obtained from the Swiss-Prot database entry P08174 (entry version 143, sequence version 4); the sequence(s) of the (human) CD56 (Neural cell adhesion molecule 1) can be obtained from the Swiss-Prot database entry P13591 (entry version 132, sequence version 3); the sequence(s) of the (human) CD57 (Kilter cell lectin-like receptor subfamily G member 1) can be obtained from the Swiss-Prot database entry Q96E93 (entry version 72, sequence version 1); the sequence(s) of the (human) CD59 (CD59 glycoprotein) can be obtained from the Swiss-Prot database entry P13987 (entry version 139, sequence information 1); the sequence(s) of the (human) CD61 (Integrin beta-3) can be obtained from the Swiss-Prot database entry P05106 (entry version 175, sequence version 2); the sequence(s) of the (human) CD63 (CD63 antigen) can be obtained from the Swiss-Prot database entry P08962 (entry version 122, sequence version 2); the sequence(s) of the (human) CD64 (High affinity immunoglobulin gamma Fc receptor I) can be obtained from the Swiss-Prot database entry P12314 (entry version 128, sequence version 2); the sequence(s) of the (human) CD66 (Carcinoembryonic antigen-related cell adhesion molecule 1) can be obtained from the Swiss-prot database entry P13688 (entry version 133, sequence version 2); the sequence(s) of the (human) CD67 (Carcinoembryonic antigen-related cell adhesion molecule 8) can be obtained from the Swiss-type prot database entry P31997 (entry version 115, sequence version 2); the sequence(s) of the (human) CD68 (Macrosialin) can be obtained from the Swiss-Prot database entry P34810 (entry version 106, sequence version 2); the sequence(s) of the (human) CD70 (CD70 antigen) can be obtained from the Swiss-Prot database entry P32970 (entry version 101, sequence version 2); the sequence(s) of the (human) CD72 (B-cell differentiation antigen CD72) can be obtained from the Swiss-Prot database entry P21854 (version entry 113, sequence version 1); the sequence(s) of the (human) CD74 (HLA class II histocompatibility antigen gamma chain) can be obtained from the Swiss-Prot database entry P04233 (entry version 141, sequence version 3); the sequence(s) of the (human) CD75 (Beta-galactoside alpha-2,6-sialyltransferase 1) can be obtained from the Swiss-Prot database entry P15907 (entry version 130, sequence version 1); the sequence(s) of the (human) CD77 (Lactosylceramide 4-alpha-galactosyltransferase) can be obtained from Swiss-Prot database entry Q9NPC4 (entry version 100, sequence version 1); the sequence(s) of the (human) CD79 (B-cell antigen receptor complex-associated protein alpha chain) can be obtained from Swiss-Prot database entry P11912 (entry version 120, sequence version 2); the sequence(s) of the (human) CD81 (CD81 antigen) can be obtained from Swiss-Prot database entry P60033 (entry version 82, sequence version 1); the sequence(s) of the (human) CD82 (CD82 antigen) can be obtained from Swiss-Prot database entry P27701 (entry version 98, sequence version 1); the sequence(s) of the (human) CD83 (CD83 antigen) can be obtained from Swiss-Prot database entry Q01151 (entry version 113, sequence version 1); the sequence(s) of the (human) CD84 (SLAM family member 5) can be obtained from Swiss-Prot database entry Q9UIB8 (entry version 87, sequence version 1); the sequence(s) of the (human) CD87 (Urokinase plasminogen activator surface receptor) can be obtained from Swiss-Prot database entry Q03405 (entry version 129, sequence version 1); the sequence(s) of the (human) CD88 (C5a anaphylatoxin chemotactic receptor) can be obtained from Swiss-Prot database entry P21730 (entry version 116, sequence version 2); the sequence(s) of the (human) CD89 (Immunoglobulin alpha Fc receptor) can be obtained from Swiss-Prot database entry P24071 (entry version 121, sequence version 1); the sequence(s) of the (human) CD90 (Thy-1 membrane glycoprotein) can be obtained from Swiss-Prot database entry P04216 (entry version 128, sequence version 2); the sequence(s) of the (human) CD91 (Prolow-density lipoprotein receptor-related protein 1) can be obtained from Swiss-Prot database entry Q07954 (entry version 133, sequence version 2); the sequence(s) of the (human) CD92 (Choline transporter-like protein 1) can be obtained from Swiss-Prot database entry Q8WWI5 (entry version 79, sequence version 1); the sequence(s) of the (human) CD93 (Complement component C1 q receptor) can be obtained from Swiss-Prot database entry Q9NPY3 (entry version 115, sequence version 3); the sequence(s) of the (human) CD94 (Natural killer cells antigen CD94) can be obtained from Swiss-Prot database entry Q13241 (entry version 107, sequence version 2); the sequence(s) of the (human) CD95 (Tumor necrosis factor ligand superfamily member 6) can be obtained from Swiss-Prot database entry P48023 (entry version 134, sequence version 1); the sequence(s) of the (human) CD97 (CD97 antigen) can be obtained from Swiss-Prot database entry P48960 (entry version 125, sequence version 4); the sequence(s) of the (human) CD98 (4F2 cell-surface antigen heavy chain) can be obtained from Swiss-Prot database entry P08195 (entry version 140, sequence version 3); the sequence(s) of the (human) CD99 (CD99 antigen) can be obtained from Swiss-Prot database entry P14209 (entry version 117, sequence version 1); the sequence(s) of the (human) CD100 (Semaphorin-4D) can be obtained from Swiss-Prot database entry Q92854 (entry version 125, sequence version 1); the sequence(s) of the (human) CD101 (Immunoglobulin superfamily member 2) can be obtained from Swiss-Prot database entry Q93033 (entry version 89, sequence version 2); the sequence(s) of the (human) CD102 (Intercellular adhesion molecule 2) can be obtained from Swiss-Prot database entry P13598 (entry version 131, sequence version 2); the sequence(s) of the (human) CD103 (Integrin alpha-E) can be obtained from Swiss-Prot database entry P38570 (entry version 118, sequence version 3); the sequence(s) of the (human) CD104 (integrin beta-4) can be obtained from Swiss-Prot database entry P16144 (entry version 160, sequence version 5); the sequence(s) of the (human) CD105 (Endoglin) can be obtained from Swiss-Prot database entry P17813 (entry version 133, sequence version 2); the sequence(s) of the (human) CD106 (Vascular cell adhesion protein 1) can be obtained from Swiss-Prot database entry P19320 (entry version 158, sequence version 1); the sequence(s) of the (human) CD107 (Lysosome-associated membrane glycoprotein 1) can be obtained from Swiss-Prot database entry P11279 (entry version 117, sequence version 3); the sequence(s) of the (human) CD108 (Semaphorin-7A) can be obtained from Swiss-Prot database entry O75326 (entry version 107, sequence version 1); the sequence(s) of the (human) CD109 (CD109 antigen) can be obtained from Swiss-Prot database entry Q6YHK3 (entry version 64, sequence version 2); the sequence(s) of the (human) CD110 (Thrombopoietin receptor) can be obtained from Swiss-Prot database entry P40238 (entry version 122, sequence version 1); the sequence(s) of the (human) CD111 (Poliovirus receptor-related protein 1) can be obtained from Swiss-Prot database entry Q15223 (entry version 114, sequence version 3); the sequence(s) of the (human) CD112 (Poliovirus receptor-related protein 2) can be obtained from Swiss-Prot database entry Q92692 (entry version 123, sequence version 1); the sequence(s) of the (human) CD113 (Poliovirus receptor-related protein 3) can be obtained from Swiss-Prot database entry Q9NQS3 (entry version 78, sequence version 1); the sequence(s) of the (human) CD114 (Granulocyte colony-stimulating factor receptor) can be obtained from Swiss-Prot database entry Q99062 (entry version 129, sequence version 1); the sequence(s) of the (human) CD115 (Macrophage colony-stimulating factor 1 receptor) can be obtained from Swiss-Prot database entry P07333 (entry version 145, sequence version 2); the sequence(s) of the (human) CD116 (Granulocyte-macrophage colony-stimulating factor receptor subunit alpha) can be obtained from Swiss-Prot database entry P15509 (entry version 128, sequence version 1); the sequence(s) of the (human) CD117 (Mast/stem cell growth factor receptor Kit) can be obtained from Swiss-Prot database entry P10721 (entry version 150, sequence version 1); the sequence(s) of the (human) CD118 (Leukemia inhibitory factor receptor) can be obtained from Swiss-Prot database entry P42702 (entry version 115, sequence version 1); the sequence(s) of the (human) CD119 (Interferon gamma receptor 1) can be obtained from Swiss-Prot database entry P15260 (entry version 140, sequence version 1); the sequence(s) of the (human) CD121 (Interleukin-1 receptor type 1) can be obtained from Swiss-Prot database entry P14778 (entry version 151, sequence version 1); the sequence(s) of the (human) CD123 (Interleukin-3 receptor subunit alpha) can be obtained from Swiss-Prot database entry P26951 (entry version 110, sequence version 1); the sequence(s) of the (human) CD124 (Interleukin-4 receptor subunit alpha) can be obtained from Swiss-Prot database entry P24394 (entry version 144, sequence version 1); the sequence(s) of the (human) CD125 (Interleukin-5 receptor subunit alpha) can be obtained from Swiss-Prot database entry Q01344 (entry version 120, sequence version 2 the sequence(s) of the (human) CD126 (Interleukin-6 receptor subunit alpha) can be obtained from Swiss-Prot database entry P08887 (entry version 143, sequence version 1); the sequence(s) of the (human) CD130 (Interleukin-6 receptor subunit beta) can be obtained from Swiss-Prot database entry P40189 (entry version 142, sequence version 2); the sequence(s) of the (human) CD131 (Cytokine receptor common subunit beta) can be obtained from Swiss-Prot database entry P32927 (entry version 128, sequence version 2); the sequence(s) of the (human) CD133 (Prominin-1) can be obtained from Swiss-Prot database entry O43490 (entry version 110, sequence version 1); the sequence(s) of the (human) CD134 (Tumor necrosis factor receptor superfamily member 4) can be obtained from Swiss-Prot database entry P43489 (entry version 106, sequence version 1); the sequence(s) of the (human) CD135 (Receptor-type tyrosine-protein kinase FLT3) can be obtained from Swiss-Prot database entry P36888 (entry version 119, sequence version 2); the sequence(s) of the (human) CD136 (Macrophage-stimulating protein receptor) can be obtained from Swiss-Prot database entry Q04912 (entry version 129, sequence version 2); the sequence(s) of the (human) CD137 (Tumor necrosis factor receptor superfamily member 9) can be obtained from Swiss-Prot database entry Q07011 (entry version 109, sequence version 1); the sequence(s) of the (human) CD138 (Syndecan-1) can be obtained from Swiss-Prot database entry P18827 (entry version 114, sequence version 3); the sequence(s) of the (human) CD140 (Platelet-derived growth factor receptor beta) can be obtained from Swiss-Prot database entry P09619 (entry version 154, sequence version 1); the sequence(s) of the (human) CD141 (Thrombomodulin) can be obtained from Swiss-Prot database entry P07204 (entry version 162, sequence version 2); the sequence(s) of the (human) CD142 (Tissue factor) can be obtained from Swiss-Prot database entry P13726 (entry version 137, sequence version 1); the sequence(s) of the (human) CD143 (Angiotensin-converting enzyme) can be obtained from Swiss-Prot database entry P12821 (entry version 157, sequence version 1); the sequence(s) of the (human) CD144 (Cadherin-5) can be obtained from Swiss-Prot database entry P33151 (entry version 108, sequence version 5); the sequence(s) of the (human) CD146 (Cell surface glycoprotein MUC18) can be obtained from Swiss-Prot database entry P43121 (entry version 109, sequence version 2); the sequence(s) of the (human) CD147 (Basigin) can be obtained from Swiss-Prot database entry P35613 (entry version 134, sequence version 2); the sequence(s) of the (human) CD148 (Receptor-type tyrosine-protein phosphatase eta) can be obtained from Swiss-Prot database entry Q12913 (entry version 124, sequence version 3); the sequence(s) of the (human) CD151 (CD151 antigen) can be obtained from Swiss-Prot database entry P48509 (entry version 108, sequence version 3); the sequence(s) of the (human) CD153 (Tumor necrosis factor ligand superfamily member 8) can be obtained from Swiss-Prot database entry P32971 (entry version 90, sequence version 1); the sequence(s) of the (human) CD155 (Poliovirus receptor) can be obtained from Swiss-Prot database entry P15151 (entry version 132, sequence version 2); the sequence(s) of the (human) CD156 (Disintegrin and metalloproteinase domain-containing protein 8) can be obtained from Swiss-Prot database entry P78325 (entry version 115, sequence version 1); the sequence(s) of the (human) CD157 (ADP-ribosyl cyclase 2) can be obtained from Swiss-Prot database entry Q10588 (entry version 116, sequence version 2); the sequence(s) of the (human) CD158 (Killer cell immunoglobulin-like receptor 3DL3) can be obtained from Swiss-Prot database entry Q8N743 (entry version 91, sequence version 2); the sequence(s) of the (human) CD159 (NKG2-A/NKG2-B type II integral membrane protein) can be obtained from Swiss-Prot database entry P26715 (entry version 116, sequence version 2); the sequence(s) of the (human) CD160 (CD160 antigen) can be obtained from Swiss-Prot database entry O95971 (entry version 98, sequence version 1); the sequence(s) of the (human) CD161 (Killer cell lectin-like receptor subfamily B member 1) can be obtained from Swiss-Prot database entry Q12918 (entry version 81, sequence version 1); the sequence(s) of the (human) CD162 (P-selectin glycoprotein ligand 1) can be obtained from Swiss-Prot database entry Q14242 (entry version 103, sequence version 1); the sequence(s) of the (human) CD163 (Scavenger receptor cysteine-rich type 1 protein M130) can be obtained from Swiss-Prot database entry Q86VB7 (entry version 77, sequence version 2); the sequence(s) of the (human) CD164 (Sialomucin core protein 24) can be obtained from Swiss-Prot database entry Q04900 (entry version 89), sequence version 2); the sequence(s) of the (human) CD166 (CD166 antigen) can be obtained from Swiss-Prot database entry Q13740 (entry version 111, sequence version 2); the sequence(s) of the (human) CD167 (Discoidin domain-containing receptor 2) can be obtained from Swiss-Prot database entry Q16832 (entry version 120, sequence version 2); the sequence(s) of the (human) CD168 (Hyaluronan mediated motility receptor) can be obtained from Swiss-Prot database entry O75330 (entry version 99, sequence version 2); the sequence(s) of the (human) CD169 (Sialoadhesin) can be obtained from Swiss-Prot database entry Q9BZZ2 (entry version 103, sequence version 2); the sequence(s) of the (human) CD170 (Sialic acid-binding Ig-like lectin 5) can be obtained from Swiss-Prot database entry O15389 (entry version 106, sequence version 1); the sequence(s) of the (human) CD171 (Neural cell adhesion molecule L1) can be obtained from Swiss-Prot database entry P32004 (entry version 139, sequence version 2); the sequence(s) of the (human) CD172 (Signal-regulatory protein beta-1) can be obtained from Swiss-Prot database entry O00241 (entry version 112, sequence version 5); the sequence(s) of the (human) CD177 (CD177 antigen) can be obtained from Swiss-Prot database entry Q8N6Q3 (entry version 65, sequence version 2); the sequence(s) of the (human) CD178 (Tumor necrosis factor ligand superfamily member 6) can be obtained from Swiss-Prot database entry P48023 (entry version 134, sequence version 1); the sequence(s) of the (human) CD179 (Immunoglobulin iota chain) can be obtained from Swiss-Prot database entry P12018 (entry version 115, sequence version 2); the sequence(s) of the (human) CD180 (CD180 antigen) can be obtained from Swiss-Prot database entry Q99467 (entry version 101, sequence version 2); the sequence(s) of the (human) CD181 (C-X-C chemokine receptor type 1) can be obtained from Swiss-Prot database entry P25024 (entry version 125, sequence version 2); the sequence(s) of the (human) CD182 (C-X-C chemokine receptor type 2) can be obtained from Swiss-Prot database entry P25025 (entry version 123, sequence version 2); the sequence(s) of the (human) CD183 (C-X-C chemokine receptor type 3) can be obtained from Swiss-Prot database entry P49682 (entry version 118, sequence version 2); the sequence(s) of the (human) CD184 (C-X-C chemokine receptor type 4) can be obtained from Swiss-Prot database entry P61073 (entry version 95, sequence version 1); the sequence(s) of the (human) CD185 (C-X-C chemokine receptor type 5) can be obtained from Swiss-Prot database entry P32302 (entry version 109, sequence version 1); the sequence(s) of the (human) CD186 (C-X-C chemokine receptor type 6) can be obtained from Swiss-Prot database entry O00574 (entry version 104, sequence version 1); the sequence(s) of the (human) CD191 (C-C chemokine receptor type 1) can be obtained from Swiss-Prot database entry P32246 (entry version 106, sequence version 1); the sequence(s) of the (human) CD192 (C-C chemokine receptor type 2) can be obtained from Swiss-Prot database entry P41597 (entry version 128, sequence version 1); the sequence(s) of the (human) CD193 (C-C chemokine receptor type 3) can be obtained from Swiss-Prot database entry P51677 (entry version 112, sequence version 1); the sequence(s) of the (human) CD200 (OX-2 membrane glycoprotein) can be obtained from Swiss-Prot database entry P41217 (entry version 110, sequence version 4); the sequence(s) of the (human) CD201 (Endothelial protein C receptor) can be obtained from Swiss-Prot database entry Q9UNN8 (entry version 110, sequence version 1); the sequence(s) of the (human) CD204 (Macrophage scavenger receptor types I and II) can be obtained from Swiss-Prot database entry P21757 (entry version 122, sequence version 1); the sequence(s) of the (human) CD206 (Macrophage mannose receptor 1) can be obtained from Swiss-Prot database entry P22897 (entry version 138, sequence version 1); the sequence(s) of the (human) CD207 (C-type lectin domain family 4 member K) can be obtained from Swiss-Prot database entry Q9UJ71 (entry version 85, sequence version 2); the sequence(s) of the (human) CD208 (Lysosome-associated membrane glycoprotein 3) can be obtained from Swiss-Prot database entry Q9UQV4 (entry version 69, sequence version 3); the sequence(s) of the (human) CD209 (CD209 antigen) can be obtained from Swiss-Prot database entry Q9NNX6 (entry version 103, sequence version 1); the sequence(s) of the (human) CD217 (Interleukin-17 receptor A) can be obtained from Swiss-Prot database entry Q96F46 (entry version 94, sequence version 2); the sequence(s) of the (human) CD218 (Interleukin-18 receptor 1) can be obtained from Swiss-Prot database entry Q13478 (entry version 104, sequence version 1); the sequence(s) of the (human) CD220 (Insulin receptor) can be obtained from Swiss-Prot database entry P06213 (entry version 175, sequence version 4); the sequence(s) of the (human) CD221 (Insulin-like growth factor 1 receptor) can be obtained from Swiss-Prot database entry P08069 (entry version 145, sequence version 1); the sequence(s) of the (human) CD222 (Cation-independent mannose-6-phosphate receptor) can be obtained from Swiss-Prot database entry P11717 (entry version 137, sequence version 3); the sequence(s) of the (human) CD223 (Lymphocyte activation gene 3 protein) can be obtained from Swiss-Prot database entry P18627 (entry version 108, sequence version 5); the sequence(s) of the (human) CD224 (Gamma-glutamyltranspeptidase 1) can be obtained from Swiss-Prot database entry P19440 (entry version 137, sequence version 2); the sequence(s) of the (human) CD225 (Interferon-induced transmembrane protein 1) can be obtained from Swiss-Prot database entry P13164 (entry version 101, sequence version 3); the sequence(s) of the (human) CD226 (CD226 antigen) can be obtained from Swiss-Prot database entry Q15762 (entry version 89, sequence version 2); the sequence(s) of the (human) CD227 (Mucin-1) can be obtained from Swiss-Prot database entry P15941 (entry version 136, sequence version 3); the sequence(s) of the (human) CD228 (Melanotransferrin) can be obtained from Swiss-Prot database entry P08582 (entry version 124, sequence version 2); the sequence(s) of the (human) CD230 (Major prion protein) can be obtained from Swiss-Prot database entry P04156 (entry version 161, sequence version 1); the sequence(s) of the (human) CD231 (Tetraspanin-7) can be obtained from Swiss-Prot database entry P41732 (entry version 115, sequence version 2); the sequence(s) of the (human) CD232 (Plexin-C1) can be obtained from Swiss-Prot database entry O60486 (entry version 80, sequence version 1); the sequence(s) of the (human) CD233 (Band 3 anion transport protein) can be obtained from Swiss-Prot database entry P02730 (entry version 167, sequence version 3); the sequence(s) of the (human) CD234 (Duffy antigen/chemokine receptor) can be obtained from Swiss-Prot database entry Q16570 (entry version 114, sequence version 3); the sequence(s) of the (human) CD236 (Glycophorin-C) can be obtained from Swiss-Prot database entry P04921 (entry version 116, sequence version 1); the sequence(s) of the (human) CD238 (Kell blood group glycoprotein) can be obtained from Swiss-Prot database entry P23276 (entry version 124, sequence version 2); the sequence(s) of the (human) CD239 (Basal cell adhesion molecule) can be obtained from Swiss-Prot database entry P50895 (entry version 117, sequence version 2); the sequence(s) of the (human) CD241 (Ammonium transporter Rh type A) can be obtained from Swiss-Prot database entry Q02094 (entry version 98, sequence version 2); the sequence(s) of the (human) CD242 (Intercellular adhesion molecule 4) can be obtained from Swiss-Prot database entry Q14773 (entry version 106, sequence version 1); the sequence(s) of the (human) CD243 (Multi-drug resistance protein 1) can be obtained from Swiss-Prot database entry P08183 (entry version 146, sequence version 3; the sequence(s) of the (human) CD244 (Natural killer cell receptor 2B4) can be obtained from Swiss-Prot database entry Q9BZW8 (entry version 94, sequence version 2); the sequence(s) of the (human) CD246 (ALK tyrosine kinase receptor) can be obtained from Swiss-Prot database entry Q9UM73 (entry version 120, sequence version 3); the sequence(s) of the (human) CD248 (Endosialin) can be obtained from Swiss-Prot database entry Q9HCUO (entry version 87, sequence version 1); the sequence(s) of the (human) CD249 (Glutamyl aminopeptidase) can be obtained from Swiss-Prot database entry Q07075 (entry version 121, sequence version 3); the sequence(s) of the (human) CD252 (Tumor necrosis factor ligand superfamily member 4) can be obtained from Swiss-Prot database entry P23510 (entry version 101, sequence version 1); the sequence(s) of the (human) CD253 (Tumor necrosis factor ligand superfamily member 10) can be obtained from Swiss-Prot database entry P50591 (entry version 118, sequence version 1); the sequence(s) of the (human) CD254 (Tumor necrosis factor ligand superfamily member 11) can be obtained from Swiss-Prot database entry O14788 (entry version 110, sequence version 1); the sequence(s) of the (human) CD256 (Tumor necrosis factor ligand superfamily member 13) can be obtained from Swiss-Prot database entry O75888 (entry version 111, sequence version 1); the sequence(s) of the (human) CD257 (Tumor necrosis factor ligand superfamily member 13B) can be obtained from Swiss-Prot database entry Q9Y275 (entry version 127, sequence version 1); the sequence(s) of the (human) CD258 (Tumor necrosis factor ligand superfamily member 14) can be obtained from Swiss-Prot database entry O43557 (entry version 117, sequence version 2); the sequence(s) of the (human) CD261 (Tumor necrosis factor receptor superfamily member 10A) can be obtained from Swiss-Prot database entry O00220 (entry version 112, sequence version 3); the sequence(s) of the (human) CD262 (Tumor necrosis factor receptor superfamily member 10B) can be obtained from Swiss-Prot database entry O14763 (entry version 133, sequence version 2); the sequence(s) of the (human) CD263 (Tumor necrosis factor receptor superfamily member 10C) can be obtained from Swiss-Prot database entry O14798 (entry version 99, sequence version 3); the sequence(s) of the (human) CD264 (Tumor necrosis factor receptor superfamily member 10D) can be obtained from Swiss-Prot database entry Q9UBN6 (entry version 109, sequence version 1); the sequence(s) of the (human) CD265 (Tumor necrosis factor receptor superfamily member 11A) can be obtained from Swiss-Prot database entry Q9Y6Q6 (entry version 100, sequence version 1); the sequence(s) of the (human) CD266 (Tumor necrosis factor receptor superfamily member 12A) can be obtained from Swiss-Prot database entry Q9NP84 (entry version 89, sequence version 1); the sequence(s) of the (human) CD267 (Tumor necrosis factor receptor superfamily member 13B) can be obtained from Swiss-Prot database entry O14836 (entry version 102, sequence version 1); the sequence(s) of the (human) CD268 (Tumor necrosis factor receptor superfamily member 13C) can be obtained from Swiss-Prot database entry Q96RJ3 (entry version 91, sequence version 1); the sequence(s) of the (human) CD269 (Tumor necrosis factor receptor superfamily member 17) can be obtained from Swiss-Prot database entry Q02223 (entry version 125, sequence version 2); the sequence(s) of the (human) CD270 (Tumor necrosis factor receptor superfamily member 14) can be obtained from Swiss-Prot database entry Q92956 (entry version 134, sequence version 3); the sequence(s) of the (human) CD271 (Tumor necrosis factor receptor superfamily member 16) can be obtained from Swiss-Prot database entry P08138 (entry version 135, sequence version 1); the sequence(s) of the (human) CD276 (CD276 antigen) can be obtained from Swiss-Prot database entry Q5ZPR3 (entry version 71, sequence version 1); the sequence(s) of the (human) CD277 (Butyrophilin subfamily 3 member A1) can be obtained from Swiss-Prot database entry O00481 (entry version 102, sequence version 3); the sequence(s) of the (human) CD280 (C-type mannose receptor 2) can be obtained from Swiss-Prot database entry Q9UBG0 (entry version 79, sequence version 2); the sequence(s) of the (human) CD281 (Toll-like receptor 1) can be obtained from swiss-Prot database entry Q15399 (entry version 125 sequence version 3); the sequence(s) of the (human) CD282 (Toll-like receptor 2) can be obtained from Swiss-Prot database entry O60603 (entry version 129, sequence version 1); the sequence(s) of the (human) CD283 (Toll-like receptor 3) can be obtained from Swiss-Prot database entry O15455 (entry version 120, sequence version 1); the sequence(s) of the (human) CD284 (Toll-like receptor 4) can be obtained from Swiss-Prot database entry O00206 (entry version 125, sequence version 2); the sequence(s) of the (human) CD286 (Toll-like receptor 6) can be obtained from Swiss-Prot database entry Q9Y2C9 (entry version 108, sequence version 2); the sequence(s) of the (human) CD288 (Toll-like receptor 8) can be obtained from Swiss-Prot database entry Q9NR97 (entry version 103, sequence version 1); the sequence(s) of the (human) CD289 (Toll-like receptor 9) can be obtained from Swiss-Prot database entry Q9NR96 (entry version 107, sequence version 2); the sequence(s) of the (human) CD290 (Toll-like receptor 10) can be obtained from Swiss-Prot database entry Q9BXR5 (entry version 105, sequence version 2); the sequence(s) of the (human) CD292 (Bone morphogenetic protein receptor type-1A) can be obtained from Swiss-Prot database entry P36894 (entry version 146, sequence version 2); the sequence(s) of the (human) CD294 (Putative G-protein coupled receptor 44) can be obtained from Swiss-Prot database entry Q9Y5Y4 (entry version 91, sequence version 3); the sequence(s) of the (human) CD295 (Leptin receptor) can be obtained from Swiss-Prot database entry P48357 (entry version 132, sequence version 2); the sequence(s) of the (human) CD296 (GPI-linked NAD(P)(+)-arginine ADP-ribosyltransferase 1) can be obtained from Swiss-Prot database entry P52961 (entry version 96, sequence version 2); the sequence(s) of the (human) CD297 (Ecto-ADP-ribosyltransferase 4) can be obtained from Swiss-Prot database entry Q93070 (entry version 106, sequence version 2); the sequence(s) of the (human) CD298 (Sodium/potassium-transporting ATPase subunit beta-3) can be obtained from Swiss-Prot database entry P54709 (entry version 102, sequence version 1); the sequence(s) of the (human) CD299 (C-type lectin domain family 4 member M) can be obtained from Swiss-Prot database entry Q9H2X3 (entry version Q9H2X3 (entry version 108, sequence version 1); the sequence(s) of the (human) CD300 (CMRF35-like molecule 9) can be obtained from Swiss-Prot database entry Q6UXG3 (entry version 67, sequence version 2); the sequence(s) of the (human) CD301 (C-type lectin domain family 10 member A) can be obtained from Swiss-Prot database entry Q81IUN9 (entry version 80, sequence version 1); the sequence(s) of the (human) CD302 (CD302 antigen) can be obtained from Swiss-Prot database entry Q81X05 (entry version 64, sequence version 1); the sequence(s) of the (human) CD303 (C-type lectin domain family 4 member C) can be obtained from Swiss-Prot database entry Q8WTTO (entry version 82, sequence version 1); the sequence(s) of the (human) CD304 (Neuropilin-1) can be obtained from Swiss-Prot database entry O14786 (entry version 129, sequence version 3); the sequence(s) of the (human) CD305 (Leukocyte-associated immunoglobulin-like receptor 1) can be obtained from Swiss-Prot database entry Q6GTX8 (entry version 70, sequence version 1); the sequence(s) of the (human) CD306 (Leukocyte-associated immunoglobulin-like receptor 2) can be obtained from Swiss-Prot database entry Q6ISS4 (entry version 63, sequence version 1); the sequence(s) of the (human) CD309 (Vascular endothelial growth factor receptor 2) can be obtained from Swiss-Prot database entry P35968 (entry version 138, sequence version 2); the sequence(s) of the (human) CD312 (EGF-like module-containing mucin-like hormone receptor-like 2) can be obtained from Swiss-Prot database entry Q9UHX3 (entry version 113, sequence version 2); the sequence(s) of the (human) CD314 (NKG2-D type II integral membrane protein) can be obtained from Swiss-Prot database entry P26718 (entry version 117, sequence version 1); the sequence(s) of the (human) CD315 (Prostaglandin F2 receptor negative regulator) can be obtained from Swiss-Prot database entry Q9P2B2 (entry version 98, sequence version 2); the sequence(s) of the (human) CD316 (Immunoglobulin superfamily member 8) can be obtained from Swiss-Prot database entry Q969P0 (entry version 81, sequence version 1); the sequence(s) of the (human) CD317 (Bone marrow stromal antigen 2) can be obtained from Swiss-Prot database entry Q10589 (entry version 95, sequence version 1); the sequence(s) of the (human) CD318 (CUB domain-containing protein 1) can be obtained from Swiss-Prot database entry Q9H5V8 (entry version 78, sequence version 3; the sequence(s) of the (human) CD319 (SLAM family member 7) can be obtained from Swiss-Prot database entry Q9NQ25 (entry version 92, sequence version 1); the sequence(s) of the (human) CD320 (CD320 antigen) can be obtained from Swiss-Prot database entry Q9NPF0 (entry version 86, sequence version 1); the sequence(s) of the (human) CD321 (Junctional adhesion molecule A) can be obtained from Swiss-Prot database entry Q9Y624 (entry version 124, sequence version 1); the sequence(s) of the (human) CD322 (Junctional adhesion molecule B) can be obtained from Swiss-Prot database entry P57087 (entry version 107, sequence version 1); the sequence(s) of the (human) CD324 (Cadherin-1) can be obtained from Swiss-Prot database entry P12830 (entry version 157, sequence version 3); the sequence(s) of the (human) CD325 (Cadherin-2) can be obtained from Swiss-Prot database entry P19022 (entry version 118, sequence version 4), the sequence(s) of the (human) CD326 (Epithelial cell adhesion molecule) can be obtained from Swiss-Prot database entry P16422 (entry version 118, sequence version 2); the sequence(s) of the (human) CD327 (Sialic acid-binding Ig-like lectin 6) can be obtained from Swiss-Prot database entry O43699 (entry version 107, sequence version 2); the sequence(s) of the (human) CD328 (Sialic acid-binding Ig-like lectin 7) can be obtained from Swiss-Prot database entry Q9Y286 (entry version 111, sequence version 1); the sequence(s) of the (human) CD329 (Sialic acid-binding Ig-like lectin 8) can be obtained from Swiss-Prot database entry Q9NYZ4 (entry version 100, sequence version 2); the sequence(s) of the (human) CD331 (Fibroblast growth factor receptor 1) can be obtained from Swiss-Prot database entry P11362 (entry version 169, sequence version 3); the sequence(s) of the (human) CD332 (Fibroblast growth factor receptor 2) can be obtained from Swiss-Prot database entry P21802 (entry version 165, sequence version 1); the sequence(s) of the (human) CD333 (Fibroblast growth factor receptor 3) can be obtained from Swiss-Prot database entry P22607 (entry version 161, sequence version 1); the sequence(s) of the (human) CD334 (Fibroblast growth factor receptor 4) can be obtained from Swiss-Prot database entry P22455 (entry version 136, sequence version 2); the sequence(s) of the (human) CD335 (Natural cytotoxicity triggering receptor 1) can be obtained from Swiss-Prot database entry O76036 (entry version 98, sequence version 1); the sequence(s) of the (human) CD336 (Natural cytotoxicity triggering receptor 2) can be obtained from Swiss-Prot database entry O95944 (entry version 86, sequence version 2); the sequence(s) of the (human) CD337 (Natural cytotoxicity triggering receptor 3) can be obtained from Swiss-Prot database entry O14931 (entry version 103, sequence version 1); the sequence(s) of the (human) CD338 (ATP-binding cassette sub-family G member 2) can be obtained from Swiss-Prot database entry Q9UNQ0 (entry version 120, sequence version 3); the sequence(s) of the (human) CD339 (Protein jagged-1) can be obtained from Swiss-Prot database entry P78504 (entry version (entry version 129; sequence version 3); the sequence(s) of the (human) CD340 (Receptor tyrosine-protein kinase erbB-2) can be obtained from Swiss-Prot database entry P04626 (entry version 162, sequence version 1); the sequence(s) of the (human) CD344 (Frizzled-4) can be obtained from Swiss-Prot database entry Q9ULV1 (entry version 107, sequence version 2); the sequence(s) of the (human) CD349 (Frizzled-9) can be obtained from Swiss-Prot database entry O00144 (entry version 103, sequence version 1); the sequence(s) of the (human) CD350 (Frizzled-10) can be obtained from Swiss-Prot database entry Q9ULW2 (entry version 100, sequence version 1); the sequence(s) of the (human) CD351 (High affinity immunoglobulin alpha and immunoglobulin mu Fc receptor) can be obtained from Swiss-Prot database entry Q8WWV6 (entry version 65, sequence version 1); the sequence(s) of the (human) CD352 (SLAM family member 6) can be obtained from Swiss-Prot database entry Q96DU3 (entry version 93, sequence version 3); the sequence(s) of the (human) CD353 (SLAM family member 8) can be obtained from Swiss-Prot database entry Q9P0V8 (entry version 80, sequence version 1); the sequence(s) of the (human) CD354 (Triggering receptor expressed on myeloid cells 1) can be obtained from Swiss-Prot database entry Q9NP99 (entry version 93, sequence version 1); the sequence(s) of the (human) CD355 (Cytotoxic and regulatory T-cell molecule) can be obtained from Swiss-Prot database entry O95727 (entry version 81, sequence version 2); the sequence(s) of the (human) CD357 (Tumor necrosis factor receptor superfamily member 18) can be obtained from Swiss-Prot database entry Q9Y5U5 (entry version 103, sequence version 1); the sequence(s) of the (human) CD358 (Tumor necrosis factor receptor superfamily member 21) can be obtained from Swiss-Prot database entry O75509 (entry version 110, sequence version 1); the sequence(s) of the (human) CD360 (Interleukin-21 receptor) can be obtained from Swiss-Prot database entry Q9HBE5 (entry version 104, sequence version 1); the sequence(s) of the (human) CD361 (Protein EVI2B) can be obtained from Swiss-Prot database entry P34910 (entry version 87, sequence version 2); the sequence(s) of the (human) CD362 (Syndecan-2) can be obtained from Swiss-Prot database entry P34741 (entry version 105, sequence version 2); the sequence(s) of the (human) CD363 (Sphingosine 1-phosphate receptor 1) can be obtained from Swiss-Prot database entry P21453 (entry version 116, sequence version 2); the sequence(s) of the (human) Criptic family protein (Criptic family protein 1-B) can be obtained from Swiss-Prot database entry P0CG36 (entry version 12, sequence version 1); the sequence(s) of the (human) Thyrotropin receptor (TSHR) can be obtained from Swiss-Prot database entry P16473 (entry version 152, sequence version 2); or the sequence(s) of the (human) Epidermal growth factor receptor (EGFR) can be obtained from Swiss-Prot database entry P00533 (entry version 178, sequence version 2).

As mentioned above, the (Ig-derived) second domain of the above-described bispecific antibody molecule may comprise an antigen-interaction-site with specificity for a cell surface molecule that naturally occurs on tumor cells.

The term "cell surface molecule that naturally occurs on tumor cells", as used herein, also denotes molecules which are presented on the surface of tumor cells. The term "naturally occurs" relates to molecules which are endogenously expressed on the surface of tumor cells. The term "cell surface molecule", relates to molecules, which are (naturally/endogenously) expressed/presented on the surface of cells and comprise domains or epitopes accessible (in vitro or in vivo) to (Ig-derived) binding domains, preferably antibodies, antibody fragments or derivatives. As illustrated above, said Ig-derived second binding domain can be a scFv. Examples for said cell surface molecules are membrane and transmembrane proteins, molecules adapted to said proteins or the cell surface etc. Accordingly, in the context of the invention said cell surface molecule is a tumor specific marker. In the context of the invention said tumor specific marker relates to a marker which usually is endogenously expressed on the surface of the tumor cells.

In context of this invention, the term "tumor specific marker" relate to molecules, which are naturally/endogenously presented and/or located on the surface of tumor cells or which are ubiquitously expressed but are only accessible for binding of antibodies, antibody fragments or antibody derivatives on the surface of tumor cells. A "tumor specific marker" as referred herein describes a protein preferentially or exclusively expressed on a tumor cell.

Preferentially means a relatively higher expression on a tumor than on a normal somatic cell while exclusively means an expression of a protein on a tumor cell which is not found on somatic cells by standard means of protein detection known to the expert. Proteins fulfilling these criteria can for instance be identified by subtractive or differential expression screens which are well known in the art. The degree to which tumor cell specific expression is required to be exploited by the method of therapy of the present invention can be assessed by a cellular assay in which cells expressing the antigen of interest and T-cells specific for this antigen are incubated together and specificity of induced killing is determined.

"Preferential expression" refers to proteins which are in comparison to normal cells highly expressed on tumor cells due to protein overexpression mediated by gene amplification, transcriptional upregulation or mRNA stabilization or mutations affecting the turnover of such proteins. Preferential also defines proteins which are expressed on tumor cells and also on normal cells, but in which normal cells are usually not accessible to T-cells or antibodies such as immune-privileged regions of the human body. Additionally, proteins which are expressed on tumor cells but are not expressed on normal cells within the scope of the treatment fall under this definition such as proteins which are exclusively expressed during embryonic development.

"Exclusive expression" refers to proteins which are solely found on tumor cells during the course of treatment. Preferably such proteins are displayed on the cell surface and carry point mutations or deletions in their extracellular part not found on normal cells. Similarly, neo-epitopes arising from tumor-specific activity of sheddases belong to this category. Exclusive expression also includes abnormal glycostructures exclusively found on tumor but not on normal cells.

In the context of the present invention, the first binding domain as described herein and the the second binding domain as described herein of the herein described bispecific antibody molecule bind to different antigens.

Examples of tumor markers that naturally occur on the surface of tumor cells are given herein below and comprise, but are not limited to EpCAM, HER-1, HER-2, HER-3, CD20, CD22, CD33, CD52, CA-12-5, HLA-DR, MUC-1 (mucin), A33-antigen, PSMA (prostate specific membrane antigen), Transferrin-receptor, Tenascin or CA-IX.

Accordingly, in the context of the present invention, the bispecific antibody molecule(s) described herein comprises an antigen/marker that naturally occurs on the surface of tumor cells selected from the group consisting of EpCAM, HER-1, HER-2, HER-3, CD20, CD22, CD33, CD52, CA-12-5, HLA-DR, MUC-1 (mucin), A33-antigen, PSMA (prostate specific membrane antigen), Transferrin-receptor, Tenascin and CA-IX. In the context of the present invention, the bispecific antibody molecule(s) described herein comprises an antigen/marker that is endogenously expressed on the surface of tumor cells selected from the group consisting of EpCAM, HER-1, HER-2, HER-3, CD20, CD22, CD33, CD52, CA-12-5, HLA-DR, MUC-1 (mucin), A33-antigen, PSMA (prostate specific membrane antigen), Transferrin-receptor, Tenascin and CA-IX.

The sequence(s) of the (human) members of the EpCAM, HER-1, HER-2, HER-3, CD20, CD22, CD33, CD52, CA-12-5, HLA-DR, MUC-1 (mucin), A33-antigen, PSMA (prostate specific membrane antigen), Transferrin-receptor, Tenascin or CA-IX are available in the UniProtKB/Swiss-Prot database and can be retrieved from www.uniprotorg/uniprot/?query=reviewed %3Ayes. These (protein) sequences also relate to annotated modified sequences. The present invention also provides techniques and methods wherein homologous sequences, and also genetic allelic variants and the like of the concise sequences provided herein are used. Preferably such "variants" and the like of the concise sequences herein are used. Preferably, such "variants" are genetic variants. The skilled person may easily deduce the relevant coding region of these (protein) sequences in these databank entries, which may also comprise the entry of genomic DNA as well as mRNA/cDNA.

The sequence(s) of the of the (human) EpCAM (Epithelial cell adhesion molecule) can be obtained from the Swiss-Prot database entry P16422 (entry version 117, sequence version 2); the sequence(s) of the (human) HER-1 (Epidermal growth factor receptor) can be obtained from the Swiss-Prot database entry P00533 (entry version 177, sequence version 2); the sequence(s) of the (human) HER-2 (Receptor tyrosine-protein kinase erbB-2) can be obtained from the Swiss-Prot database entry P04626 (entry version 161, sequence version 1); the sequence(s) of the (human) HER-3 (Receptor tyrosine-protein kinase erbB-3) can be obtained from the Swiss-Prot database entry P21860 (entry version 140, sequence version 1); the sequence(s) of the (human) CD20 (B-lymphocyte antigen CD20) can be obtained from the Swiss-Prot database entry P11836 (entry version 117, sequence version 1); the sequence(s) of the (human) CD22 (B-lymphocyte antigen CD22) can be obtained from the Swiss-Prot database entry P20273 (entry version 135, sequence version 2); the sequence(s) of the (human) CD33 (B-lymphocyte antigen CD33) can be obtained from the Swiss-Prot database entry P20138 (entry version 129, sequence version 2); the sequence(s) of the (human) CA-12-5 (Mucin 16) can be obtained from the Swiss-Prot database entry Q8WXI7 (entry version 66, sequence version 2); the sequence(s) of the (human) HLA-DR can be obtained from the Swiss-Prot database entry Q29900 (entry version 59, sequence version 1); the sequence(s) of the (human) MUC-1 (Mucin-1) can be obtained from the Swiss-Prot database entry P15941 (entry version 135, sequence version 3); the sequence(s) of the (human) A33 (cell surface A33 antigen) can be obtained from the Swiss-Prot database entry Q99795 (entry version 104, sequence version 1); the sequence(s) of the (human) PSMA (Glutamate carboxypeptidase 2) can be obtained from the Swiss-Prot database entry Q04609 (entry version 133, sequence version 1), the sequence(s) of the (human) Transferrin receptor can be obtained from the Swiss-Prot database entries Q9UP52 (entry version 99, sequence version 1) and P02786 (entry version 152, sequence version 2); the sequence of the (human) Tenascin can be obtained from the Swiss-Prot database entry P24821 (entry version 141, sequence version 3); or the sequence(s) of the (human) CA-IX (the carbonic anhydrase 9) can be obtained from the Swiss-Prot database entry Q16790 (entry version 115, sequence version 2).

In the context of the present invention, a bispecific antibody which comprises a first binding domain binding to/directed against/interacting with or on (human) Cripto and a second domain binding to/directed against/interacting with (human) EpCAM is described.

The molecules or constructs (i.e., the bispecific antibody molecules described herein) provided herein are particularly useful in medical settings. For examples malignant diseases may be treated with a bispecific construct described herein. In the context of the present invention the malignant disease may be a cancer/carcinoma of epithelial, endothelial or mesothelial origin or a cancer of the blood. In the context of the present invention the cancer/carcinoma is selected from the group consisting of gastrointestinal cancer, pancreatic cancer, cholangiocellular cancer, lung cancer, breast cancer, ovarian cancer, skin cancer, oral cancer, gastric cancer, cervical cancer, B and T-cell lymphoma, myeloid leukemia, ovarial cancer, leukemia, lymphatic leukemia, nasopharyngeal carcinoma, colon cancer, prostate cancer, renal cell cancer, head and neck cancer, skin cancer (melanoma), cancers of the genitor-urinary tract, e.g., testis cancer, ovarial cancer, endothelial cancer, cervix cancer and kidney cancer, cancer of the bile duct, esophagus cancer, cancer of the salivatory glands and cancer of the thyroid gland or other tumorous diseases like haematological tumors, gliomas, sarcomas or osteosarcomas.

The molecules or constructs (i.e., the bispecific antibody molecules described herein) provided herein are particularly useful in medical settings. For example, tumorous diseases and/or lymphomas may be treated with a bispecific construct directed against these medical indication(s). The indication for a bispecific antibody (molecule) is given by the expression of the tumor antigen. A tumor antigen expressed in an entity could be virtually combined with any of the above mentioned T-cell marker (representing the antigen that naturally occurs/that is endogenously expressed on the surface of a tumor cell). For example, gastrointestinal cancer, pancreatic cancer, cholangiocellular cancer, lung cancer, breast cancer, ovarian cancer, skin cancer and/or oral cancer may be treated with a bispecific molecule or construct (i.e., the bispecific antibody molecule described herein) directed against (human) EpCAM (as the tumor-specific antigen naturally occurring on the surface of a tumor cell) via the second binding domain and comprises a first binding domain directed against/binding to/interacting with one of the herein defined antigens that does not naturally occur in and/or on T-cells (CD8+ T-cells). Accordingly, in the context of the present, a bispecific antibody construct directed against (human) EpCAM (as second binding domain) and comprises a first binding domain directed against/binding to/interacting with Cripto may be used in the treatment of gastrointestinal cancer, for example adenocarcinoma of gastrointestinal origin. Gastrointestinal cancer, pancreatic cancer, cholangiocellular cancer, lung cancer, breast cancer, ovarian cancer, skin cancer and/or oral cancer may be treated with a bispecific molecule or construct (i.e., the bispecific antibody molecule described herein) directed against (human) HER1 (as the tumor-specific antigen naturally occurring on the surface of a tumor cell) via the second binding domain and comprises a first binding domain directed against/binding to/interacting with one of the herein defined antigens that does not naturally occur in and/or on T-cells (CD8+ T-cells). Gastric cancer, breast cancer and/or cervical cancer may be treated with a bispecific molecule or construct (i.e., the bispecific antibody molecule described herein) directed against (human) HER2 (as the tumor-specific antigen naturally occurring on the surface of a tumor cell) via the second binding domain and comprises a first binding domain directed against/binding to/interacting with one of the herein defined antigens that does not naturally occur in and/or on T-cells (CD8+ T-cells). Gastric cancer and/or lung cancer may be treated with a bispecific molecule or construct (i.e., the bispecific antibody molecule described herein) directed against (human) HERS (as the tumor-specific antigen naturally occurring on the surface of a tumor cell) via the second binding domain and comprises a first binding domain directed against/binding to/interacting with one of the herein defined antigens that does not naturally occur in and/or on T-cells (CD8+ T-cells). B-cell lymphoma and/or T-cell lymphoma may be treated with a bispecific molecule or construct (i.e., the bispecific antibody molecule described herein) directed against (human) CD20 (as the tumor-specific antigen naturally occurring on the surface of a tumor cell) via the second binding domain and comprises a first binding domain directed against/binding to/interacting with one of the herein defined antigens that does not naturally occur in and/or on T-cells (CD8+ T-cells). B-cell lymphoma and/or T-cell lymphoma may be treated with a bispecific molecule or construct (i.e., the bispecific antibody molecule described herein) directed against (human) CD22 (as the tumor-specific antigen naturally occurring on the surface of a tumor cell) via the second binding domain and comprises a first binding domain directed against/binding to/interacting with one of the herein defined antigens that does not naturally occur in and/or on T-cells (CD8+ T-cells). Myeloid leukemia may be treated with a bispecific construct directed against (human) CD33 (as the tumor-specific antigen naturally occurring on the surface of a tumor cell) via the second binding domain and comprises a first binding domain directed against/binding to/interacting with one of the herein defined antigens that does not naturally occur in and/or on T-cells (CD8+ T-cells). Ovarian cancer, lung cancer, breast cancer and/or gastrointestinal cancer may be treated with a bispecific molecule or construct (i.e., the bispecific antibody molecule described herein) directed against (human) CA12-5 (as the tumor-specific antigen naturally occurring on the surface of a tumor cell) via the second binding domain and comprises a first binding domain directed against/binding to/interacting with one of the herein defined antigens that does not naturally occur in and/or on T-cells (CD8+ T-cells). Gastrointestinal cancer, leukemia and/or nasopharyngeal carcinoma may be treated with a bispecific molecule or construct (i.e., the bispecific antibody molecule described herein) directed against (human) HLA-DR (as the tumor-specific antigen naturally occurring on the surface of a tumor cell) via the second binding domain and comprises a first binding domain directed against/binding to/interacting with one of the herein defined antigens that does not naturally occur in and/or on T-cells (CD8+ T-cells). Colon cancer, breast cancer, ovarian cancer, lung cancer and/or pancreatic cancer may be treated with a bispecific molecule or construct (i.e., the bispecific antibody molecule described herein) directed against (human) MUC-1 (as the tumor-specific antigen naturally occurring on the surface of a tumor cell) via the second binding domain and comprises a first binding domain directed against/binding to/interacting with one of the herein defined antigens that does not naturally occur in and/or on T-cells (CD8+ T-cells). Colon cancer may be treated with a bispecific molecule or construct (i.e., the bispecific antibody molecule described herein) directed against (human) A33 (as the tumor-specific antigen naturally occurring on the surface of a tumor cell) via the second binding domain and comprises a first binding domain directed against/binding to/interacting with one of the herein defined antigens that does not naturally occur in and/or on T-cells (CD8+ T-cells). Prostate cancer may be treated with a bispecific molecule or construct (i.e., the bispecific antibody molecule described herein) directed against (human) PSMA (as the tumor-specific antigen naturally occurring on the surface of a tumor cell) via the second binding domain and comprises a first binding domain directed against/binding to/interacting with one of the herein defined antigens that does not naturally occur in and/or on T-cells (CD8+ T-cells). Gastrointestinal cancer, pancreatic cancer, cholangiocellular cancer, lung cancer, breast cancer, ovarian cancer, skin cancer and/or oral cancer may be treated with a bispecific molecule or construct (i.e., the bispecific antibody molecule described herein) directed against (human) transferrin receptor (as the tumor-specific antigen naturally occurring on the surface of a tumor cell) via the second binding domain and comprises a first binding domain directed against/binding to/interacting with one of the herein defined antigens that does not naturally occur in and/or on T-cells (CD8+ T-cells). Pancreatic cancer, lunger cancer and/or breast cancer may be treated with a bispecific molecule or construct (i.e., the bispecific antibody molecule described herein) directed against (human) transferrin receptor (as the tumor-specific antigen naturally occurring on the surface of a tumor cell) via the second binding domain and comprises a first binding domain directed against/binding to/interacting with one of the herein defined antigens that does not naturally occur in and/or on T-cells (CD8+ T-cells). Renal cancer may be treated with a bispecific molecule or construct (i.e., the bispecific antibody molecule described herein) directed against (human) CA-IX (as the tumor-specific antigen naturally occurring on the surface of a tumor cell) via the second binding domain and comprises a first binding domain directed against/binding to/interacting with one of the herein defined antigens that does not naturally occur in and/or on T-cells (CD8+ T-cells).

As also illustrated in the appended examples, as a proof of concept of the present invention, a specific bispecific antibody molecule of the invention comprises the above defined first (Ig-derived) domain binding to/directed against/interacting with or on (human) EGFR and a second, (Ig-derived) domain binding to/directed against/interacting with or on (human) EpCAM.

Epithelial cell adhesion molecule (EpCAM, also called 17-1A antigen, KSA, EGP40, GA733-2, ks1-4 or esa) is a 40-kDa membrane-integrated glycoprotein of 314 amino acids with specific expression in certain epithelia and on many human carcinomas (reviewed in Balzar, *J. Mol. Med.* (1999), 77, 699-712). EpCAM was discovered and subsequently cloned through its recognition by the murine monoclonal antibody 17-1A/edrecolomab (Goettlinger, Int J Cancer 38 (1986), 47-53 and Simon, Proc. Natl. Acad. Sci. USA 87 (1990), 2755-2759). EpCAM serves to adhere epithelial cells in an oriented and highly ordered fashion (Litvinov, J Cell Biol. 139 (1997), 1337-1348). Upon malignant transformation of epithelial cells the rapidly growing tumor cells are abandoning the high cellular order of epithelia. Consequently, the surface distribution of EpCAM becomes less restricted and the molecule better exposed on tumor cells and accessible for binding of antibodies, antibody fragments or antibody derivatives on the surface of tumor cells. Due to their epithelial cell origin, tumor cells from most carcinomas still express EpCAM on their surface.

In vivo, expression of EpCAM is related to increased epithelial proliferation and negatively correlates with cell differentiation (for review see Balzar, J. Mol. Med. 77 (1999), 699-712). Expression of EpCAM is essentially seen with all major carcinomas (reviewed in Balzar, J. Mol. Med. 77 (1999), 699-712 or documented, inter alia, in De Bree, Nucl Med Commun. 15 (1994), 613-27; Zhang, Clin Cancer Res. 4 (1998), 295-302). Because of its widespread expression, EpCAM is referred to as a "pan-carcinoma" antigen. In many cases, tumor cells were observed to express EpCAM to a much higher degree than their parental epithelium or less aggressive forms of said cancers. For example, increased EpCAM expression represents an early event in the development of prostate cancer (Poczatek, J. Urol. 162 (1999), 1462-1644). In addition, in the majority of both squamous and adenocarcinomas of the cervix a strong EpCAM expression correlates with an increased proliferation and the disappearance of markers for terminal differentiation (Litvinov, Am. J. Pathol. 148 (1996), 865-75). In breast cancer, overexpression of EpCAM on tumor cells is a predictor of survival (Gastl, Lancet 356 (2000), 1981-1982). EpCAM is a marker for the detection of disseminated tumor cells in patients suffering from squamous cell carcinoma of the head, neck and lung (Chaubal, Anticancer Res. 19 (1999), 2237-2242 and Piyathilake, Hum. Pathol. 31 (2000), 482-487). Normal squamous epithelium, as found in epidermis, oral cavity, epiglottis, pharynx, larynx and esophagus did not significantly express EpCAM (Quak, Hybridoma 9 (1990), 377-387). EpCAM has been shown to be expressed on the majority of primary, metastatic, and disseminated NSCLC (non small cell lung cancer cells (Passlick, Int J Cancer 87 (2000), 548-552)), on gastric and gastro-oesophageal junction adenocarcinomas (Martin, J. Clin. Pathol. 52 (1999), 701-4) and in cell lines derived from colorectal, pancreatic carcinomas and breast carcinomas (Szala, Proc. Natl. Acad. Sci. USA 87 (1990), 3542-6 and Packeisen, Hybridoma 18 (1999), 37-40).

As illustratively shown in the appended Examples, as a proof of concept of the present invention, the (human) anti-EGFR antibody was combined with the (murine) anti-EpCAM (G8.8) in order to form the bispecific construct MAb225_scFv_G8.8. The amino acid sequence of the light chain of the (human) anti-EGFR antibody is shown below (referring to SEQ ID NO: 1):

```
Met Arg Cys Leu Ala Glu Phe Leu Gly Leu Leu Val
Leu Trp Ile Pro Gly Ala Ile Gly Asp Ile Leu Leu
Thr Gln Ser Pro Val Ile Leu Ser Val Ser Pro Gly
Glu Arg Val Ser Phe Ser Cys Arg Ala Ser Gln Ser
Ile Gly Thr Asn Ile His Trp Tyr Gln Gln Arg Thr
Asn Gly Ser Pro Arg Leu Leu Ile Lys Tyr Ala Ser
Glu Ser Ile Ser Gly Ile Pro Ser Arg Phe Ser Gly
Ser Gly Ser Gly Thr Asp Phe Thr Leu Ser Ile Asn
Ser Val Glu Ser Glu Asp Ile Ala Asp Tyr Tyr Cys
Gln Gln Asn Asn Asn Trp Pro Thr Thr Phe Gly Ala
Gly Thr Lys Leu Glu Leu Lys Arg Ala Asp Ala Ala
Pro Thr Val Ser Ile Phe Pro Pro Ser Ser Glu Gln
Leu Thr Ser Gly Gly Ala Ser Val Val Cys Phe Leu
Asn Asn Phe Tyr Pro Lys Asp Ile Asn Val Lys Trp
```

-continued

```
Lys Ile Asp Gly Ser Glu Arg Gln Asn Gly Val Leu
Asn Ser Trp Thr Asp Gln Asp Ser Lys Asp Ser Thr
Tyr Ser Met Ser Ser Thr Leu Thr Leu Thr Lys Asp
Glu Tyr Glu Arg His Asn Ser Tyr Thr Cys Glu Ala
Thr His Lys Thr Ser Thr Ser Pro Ile Val Lys Ser
Phe Asn Arg Asn Glu Cys
```

The amino acid sequence of the heavy chain of the (human) anti-EGFR antibody is shown below (referring to SEQ ID NO: 2):

```
Met Ala Val Leu Ala Leu Leu Phe Cys Leu Val Thr
Phe Pro Ser Cys Val Leu Ser Gln Val Gln Leu Lys
Gln Ser Gly Pro Gly Leu Val Gln Pro Ser Gln Ser
Leu Ser Ile Thr Cys Thr Val Ser Gly Phe Ser Leu
Thr Asn Tyr Gly Val His Trp Val Arg Gln Ser Pro
Gly Lys Gly Leu Glu Trp Leu Gly Val Ile Trp Ser
Gly Gly Asn Thr Asp Tyr Asn Thr Pro Phe Thr Ser
Arg Leu Ser Ile Asn Lys Asp Asn Ser Lys Ser Gln
Val Phe Phe Lys Met Asn Ser Leu Gln Ser Asn Asp
Thr Ala Ile Tyr Tyr Cys Ala Arg Ala Leu Thr Tyr
Tyr Asp Tyr Glu Phe Ala Tyr Trp Gly Gln Gly Thr
Leu Val Thr Val Ser Ala Ala Lys Thr Thr Ala Pro
Ser Val Tyr Pro Leu Ala Pro Val Cys Gly Asp Thr
Thr Gly Ser Ser Val Thr Leu Gly Cys Leu Val Lys
Gly Tyr Phe Pro Glu Pro Val Thr Leu Thr Trp Asn
Ser Gly Ser Leu Ser Ser Gly Val His Thr Phe Pro
Ala Val Leu Gln Ser Asp Leu Tyr Thr Leu Ser Ser
Ser Val Thr Val Thr Ser Ser Thr Trp Pro Ser Gln
Ser Ile Thr Cys Asn Val Ala His Pro Ala Ser Ser
Thr Lys Val Asp Lys Lys Ile Glu Pro Arg Gly Pro
Thr Ile Lys Pro Cys Pro Pro Cys Lys Cys Pro Ala
Pro Asn Leu Leu Gly Gly Pro Ser Val Phe Ile Phe
Pro Pro Lys Ile Lys Asp Val Leu Met Ile Ser Leu
Ser Pro Ile Val Thr Cys Val Val Val Asp Val Ser
Glu Asp Asp Pro Asp Val Gln Ile Ser Trp Phe Val
Asn Asn Val Glu Val His Thr Ala Gln Thr Gln Thr
His Arg Glu Asp Tyr Asn Ser Thr Leu Arg Val Val
Ser Ala Leu Pro Ile Gln His Gln Asp Trp Met Ser
Gly Lys Glu Phe Lys Cys Lys Val Asn Asn Lys Asp
Leu Pro Ala Pro Ile Glu Arg Thr Ile Ser Lys Pro
Lys Gly Ser Val Arg Ala Pro Gln Val Tyr Val Leu
```

-continued

```
Pro Pro Pro Glu Glu Glu Met Thr Lys Lys Gln Val
Thr Leu Thr Cys Met Val Thr Asp Phe Met Pro Glu
Asp Ile Tyr Val Glu Trp Thr Asn Asn Gly Lys Thr
Glu Leu Asn Tyr Lys Asn Thr Glu Pro Val Leu Asp
Ser Asp Gly Ser Tyr Phe Met Tyr Ser Lys Leu Arg
Val Glu Lys Lys Asn Trp Val Glu Arg Asn Ser Tyr
Ser Cys Ser Val Val His Glu Gly Leu His Asn His
His Thr Thr Lys Ser Phe Ser Arg Thr Pro Gly Lys
```

The amino acid sequence of the light chain of the (murine) anti-EpCAM (G8.8) antibody is shown below (referring to SEQ ID NO: 3):

```
Met Arg Cys Leu Ala Glu Phe Leu Gly Leu Leu Val
Leu Trp Ile Pro Gly Ala Ile Gly Asp Ile Gln Met
Thr Gln Ser Pro Ala Ser Leu Ser Ala Ser Leu Gly
Glu Thr Val Ser Ile Glu Cys Leu Ala Ser Glu Gly
Ile Ser Asn Asp Leu Ala Trp Tyr Gln Gln Lys Ser
Gly Lys Ser Pro Gln Leu Leu Ile Tyr Ala Thr Ser
Arg Leu Gln Asp Gly Val Pro Ser Arg Phe Ser Gly
Ser Gly Ser Gly Thr Arg Tyr Ser Leu Lys Ile Ser
Gly Met Gln Pro Glu Asp Glu Ala Asp Tyr Phe Cys
Gln Gln Ser Tyr Lys Tyr Pro Trp Thr Phe Gly Gly
Gly Thr Lys Leu Glu Leu Lys Arg Ala Asp Ala Ala
Pro Thr Val Ser Ile Phe Pro Pro Ser Ser Glu Gln
Leu Thr Ser Gly Gly Ala Ser Val Val Cys Phe Leu
Asn Asn Phe Tyr Pro Lys Asp Ile Asn Val Lys Trp
Lys Ile Asp Gly Ser Glu Arg Gln Asn Gly Val Leu
Asn Ser Trp Thr Asp Gln Asp Ser Lys Asp Ser Thr
Tyr Ser Met Ser Ser Thr Leu Thr Leu Thr Lys Asp
Glu Tyr Glu Arg His Asn Ser Tyr Thr Cys Glu Ala
Thr His Lys Thr Ser Thr Ser Pro Ile Val Lys Ser
Phe Asn Arg Asn Glu Cys
```

The amino acid sequence of the heavy chain of the (murine) anti-EpCAM (G8.8) antibody is shown below (referring to SEQ ID NO: 4):

```
Met Asp Ile Arg Leu Ser Leu Ala Phe Leu Val Leu
Phe Ile Lys Gly Val Gln Cys Glu Val Gln Leu Ala
Glu Ser Gly Gly Gly Leu Val Gln Pro Gly Arg Ser
Met Lys Leu Ser Cys Ala Ala Ser Gly Phe Thr Phe
Ser Asn Phe Pro Met Ala Trp Val Arg Gln Ala Pro
Thr Lys Gly Leu Glu Trp Val Ala Thr Ile Ser Thr
Ser Gly Gly Ser Thr Tyr Tyr Arg Asp Ser Val Lys
```

-continued

```
Gly Arg Phe Thr Ile Ser Arg Asp Asn Ala Lys Ser
Thr Leu Tyr Leu Gln Met Asn Ser Leu Arg Ser Glu
Asp Thr Ala Thr Tyr Tyr Cys Thr Arg Thr Leu Tyr
Ile Leu Arg Val Phe Tyr Phe Asp Tyr Trp Gly Gln
Gly Val Met Val Thr Val Ser Ser Ala Lys Thr Thr
Ala Pro Ser Val Tyr Pro Leu Ala Pro Val Cys Gly
Asp Thr Thr Gly Ser Ser Val Thr Leu Gly Cys Leu
Val Lys Gly Tyr Phe Pro Glu Pro Val Thr Leu Thr
Trp Asn Ser Gly Ser Leu Ser Ser Gly Val His Thr
Phe Pro Ala Val Leu Gln Ser Asp Leu Tyr Thr Leu
Ser Ser Ser Val Thr Val Thr Ser Ser Thr Trp Pro
Ser Gln Ser Ile Thr Cys Asn Val Ala His Pro Ala
Ser Ser Thr Lys Val Asp Lys Lys Ile Glu Pro Arg
Gly Pro Thr Ile Lys Pro Cys Pro Pro Cys Lys Cys
Pro Ala Pro Asn Leu Leu Gly Gly Pro Ser Val Phe
Ile Phe Pro Pro Lys Ile Lys Asp Val Leu Met Ile
Ser Leu Ser Pro Ile Val Thr Cys Val Val Val Asp
Val Ser Glu Asp Asp Pro Asp Val Gln Ile Ser Trp
Phe Val Asn Asn Val Glu Val His Thr Ala Gln Thr
Gln Thr His Arg Glu Asp Tyr Asn Ser Thr Leu Arg
Val Val Ser Ala Leu Pro Ile Gln His Gln Asp Trp
Met Ser Gly Lys Glu Phe Lys Cys Lys Val Asn Asn
Lys Asp Leu Pro Ala Pro Ile Glu Arg Thr Ile Ser
Lys Pro Lys Gly Ser Val Arg Ala Pro Gln Val Tyr
Val Leu Pro Pro Pro Glu Glu Glu Met Thr Lys Lys
Gln Val Thr Leu Thr Cys Met Val Thr Asp Phe Met
Pro Glu Asp Ile Tyr Val Glu Trp Thr Asn Asn Gly
Lys Thr Glu Leu Asn Tyr Lys Asn Thr Glu Pro Val
Leu Asp Ser Asp Gly Ser Tyr Phe Met Tyr Ser Lys
Leu Arg Val Glu Lys Lys Asn Trp Val Glu Arg Asn
Ser Tyr Ser Cys Ser Val Val His Glu Gly Leu His
Asn His His Thr Thr Lys Ser Phe Ser Arg Thr Pro
Gly Lys
```

The amino acid sequence of the light chain of the bispecific product (MAb225_scFv_G8.8) is shown below (referring to SEQ ID NO: 5):

```
Met Arg Cys Leu Ala Glu Phe Leu Gly Leu Leu Val
Leu Trp Ile Pro Gly Ala Ile Gly Asp Ile Leu Leu
Thr Gln Ser Pro Val Ile Leu Ser Val Ser Pro Gly
Glu Arg Val Ser Phe Ser Cys Arg Ala Ser Gln Ser
```

-continued

Ile Gly Thr Asn Ile His Trp Tyr Gln Gln Arg Thr

Asn Gly Ser Pro Arg Leu Leu Ile Lys Tyr Ala Ser

Glu Ser Ile Ser Gly Ile Pro Ser Arg Phe Ser Gly

Ser Gly Ser Gly Thr Asp Phe Thr Leu Ser Ile Asn

Ser Val Glu Ser Glu Asp Ile Ala Asp Tyr Tyr Cys

Gln Gln Asn Asn Asn Trp Pro Thr Thr Phe Gly Ala

Gly Thr Lys Leu Glu Leu Lys Arg Ala Asp Ala Ala

Pro Thr Val Ser Ile Phe Pro Pro Ser Ser Glu Gln

Leu Thr Ser Gly Gly Ala Ser Val Val Cys Phe Leu

Asn Asn Phe Tyr Pro Lys Asp Ile Asn Val Lys Trp

Lys Ile Asp Gly Ser Glu Arg Gln Asn Gly Val Leu

Asn Ser Trp Thr Asp Gln Asp Ser Lys Asp Ser Thr

Tyr Ser Met Ser Ser Thr Leu Thr Leu Thr Lys Asp

Glu Tyr Glu Arg His Asn Ser Tyr Thr Cys Glu Ala

Thr His Lys Thr Ser Thr Ser Pro Ile Val Lys Ser

Phe Asn Arg Asn Glu Cys

The amino acid sequence of the heavy chain of the bispecific product (MAb225_scFv_G8.8) is shown below (referring to SEQ ID NO: 6):

Met Ala Val Leu Ala Leu Leu Phe Cys Leu Val Thr

Phe Pro Ser Cys Val Leu Ser Gln Val Gln Leu Lys

Gln Ser Gly Pro Gly Leu Val Gln Pro Ser Gln Ser

Leu Ser Ile Thr Cys Thr Val Ser Gly Phe Ser Leu

Thr Asn Tyr Gly Val His Trp Val Arg Gln Ser Pro

Gly Lys Gly Leu Glu Trp Leu Gly Val Ile Trp Ser

Gly Gly Asn Thr Asp Tyr Asn Thr Pro Phe Thr Ser

Arg Leu Ser Ile Asn Lys Asp Asn Ser Lys Ser Gln

Val Phe Phe Lys Met Asn Ser Leu Gln Ser Asn Asp

Thr Ala Ile Tyr Tyr Cys Ala Arg Ala Leu Thr Tyr

Tyr Asp Tyr Glu Phe Ala Tyr Trp Gly Gln Gly Thr

Leu Val Thr Val Ser Ala Ala Lys Thr Thr Ala Pro

Ser Val Tyr Pro Leu Ala Pro Val Cys Gly Asp Thr

Thr Gly Ser Ser Val Thr Leu Gly Cys Leu Val Lys

Gly Tyr Phe Pro Glu Pro Val Thr Leu Thr Trp Asn

Ser Gly Ser Leu Ser Ser Gly Val His Thr Phe Pro

Ala Val Leu Gln Ser Asp Leu Tyr Thr Leu Ser Ser

Ser Val Thr Val Thr Ser Ser Thr Trp Pro Ser Gln

Ser Ile Thr Cys Asn Val Ala His Pro Ala Ser Ser

Thr Lys Val Asp Lys Lys Ile Glu Pro Arg Gly Pro

Thr Ile Lys Pro Cys Pro Pro Cys Lys Cys Pro Ala

Pro Asn Leu Leu Gly Gly Pro Ser Val Phe Ile Phe

-continued

Pro Pro Lys Ile Lys Asp Val Leu Met Ile Ser Leu

Ser Pro Ile Val Thr Cys Val Val Val Asp Val Ser

Glu Asp Asp Pro Asp Val Gln Ile Ser Trp Phe Val

Asn Asn Val Glu Val His Thr Ala Gln Thr Gln Thr

His Arg Glu Asp Tyr Asn Ser Thr Leu Arg Val Val

Ser Ala Leu Pro Ile Gln His Gln Asp Trp Met Ser

Gly Lys Glu Phe Lys Cys Lys Val Asn Asn Lys Asp

Leu Pro Ala Pro Ile Glu Arg Thr Ile Ser Lys Pro

Lys Gly Ser Val Arg Ala Pro Gln Val Tyr Val Leu

Pro Pro Pro Glu Glu Glu Met Thr Lys Lys Gln Val

Thr Leu Thr Cys Met Val Thr Asp Phe Met Pro Glu

Asp Ile Tyr Val Glu Trp Thr Asn Asn Gly Lys Thr

Glu Leu Asn Tyr Lys Asn Thr Glu Pro Val Leu Asp

Ser Asp Gly Ser Tyr Phe Met Tyr Ser Lys Leu Arg

Val Glu Lys Lys Asn Trp Val Glu Arg Asn Ser Tyr

Ser Cys Ser Val Val His Glu Gly Leu His Asn His

His Thr Thr Lys Ser Phe Ser Arg Thr Pro Gly Lys

Gly Gly Gly Gly Ser Gly Gly Gly Gly Ser Glu Val

Gln Leu Ala Glu Ser Gly Gly Gly Leu Val Gln Pro

Gly Arg Ser Met Lys Leu Ser Cys Ala Ala Ser Gly

Phe Thr Phe Ser Asn Phe Pro Met Ala Trp Val Arg

Gln Ala Pro Thr Lys Cys Leu Glu Trp Val Ala Thr

Ile Ser Thr Ser Gly Gly Ser Thr Tyr Tyr Arg Asp

Ser Val Lys Gly Arg Phe Thr Ile Ser Arg Asp Asn

Ala Lys Ser Thr Leu Tyr Leu Gln Met Asn Ser Leu

Arg Ser Glu Asp Thr Ala Thr Tyr Tyr Cys Thr Arg

Thr Leu Tyr Ile Leu Arg Val Phe Tyr Phe Asp Tyr

Trp Gly Gln Gly Val Met Val Thr Val Ser Ser Gly

Gly Gly Gly Ser Gly Gly Gly Gly Ser Gly Gly Gly

Gly Ser Asp Ile Gln Met Thr Gln Ser Pro Ala Ser

Leu Ser Ala Ser Leu Gly Glu Thr Val Ser Ile Glu

Cys Leu Ala Ser Glu Gly Ile Ser Asn Asp Leu Ala

Trp Tyr Gln Gln Lys Ser Gly Lys Ser Pro Gln Leu

Leu Ile Tyr Ala Thr Ser Arg Leu Gln Asp Gly Val

Pro Ser Arg Phe Ser Gly Ser Gly Ser Gly Thr Arg

Tyr Ser Leu Lys Ile Ser Gly Met Gln Pro Glu Asp

Glu Ala Asp Tyr Phe Cys Gln Gln Ser Tyr Lys Tyr

Pro Trp Thr Phe Gly Cys Gly Thr Lys Leu Glu Leu

Lys

Figure 20:
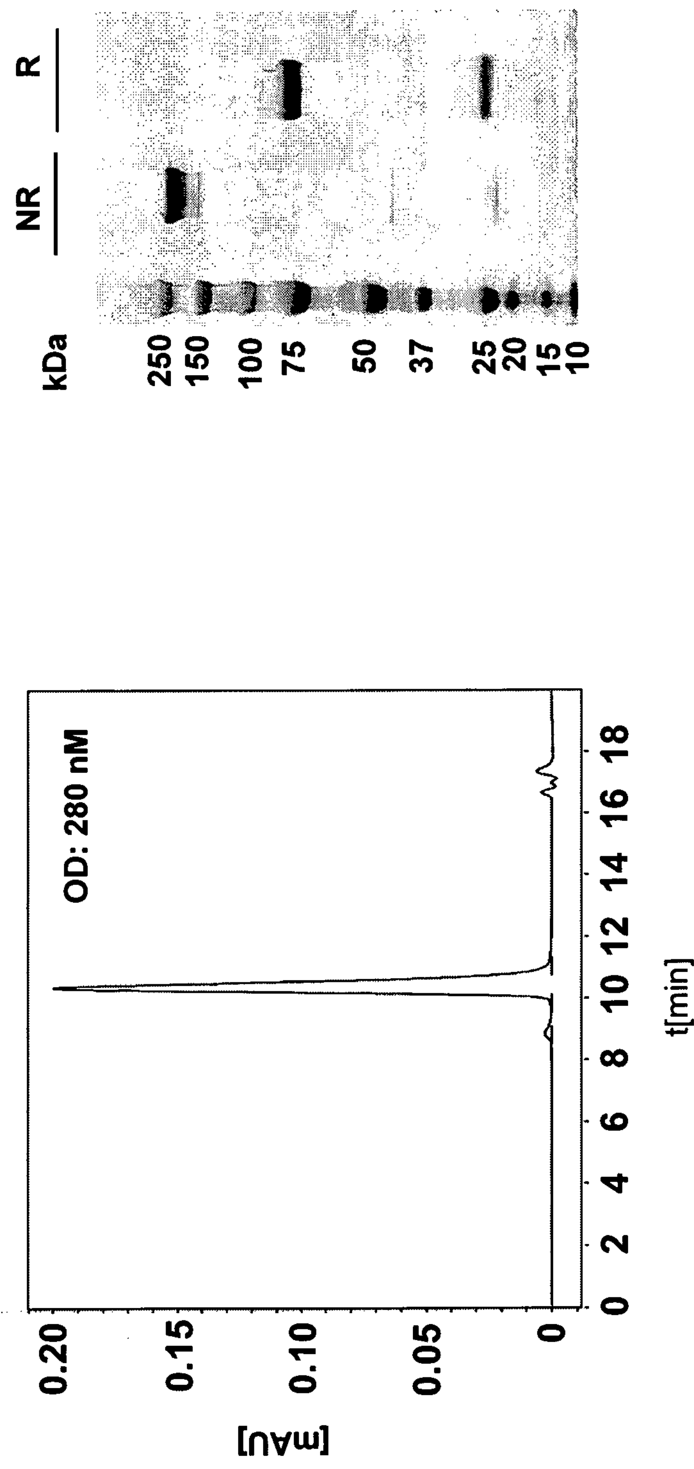

Furthermore, as illustrated in FIGS. 20 and 21, as a (further) proof of concept of the present invention, the bispecific antibody (BiAb) "BsAb EpCAM-EGFRvIII, MR1.1" with an antigen binding site for del-(human) hEGFRvIII on one arm and for (murine) EpCAM on the other arm was constructed; see Example 4. The amino acid sequence of the light chain of the bispecific product (BsAb EpCAM-EGFRvIII, MR1.1) is shown in FIG. 23A (referring to SEQ ID NO: 15). The amino acid sequence of the heavy chain of the bispecific product (BsAb EpCAM-EGFRvIII, MR1.1) is shown in FIG. 23B (referring to SEQ ID NO: 16).

The invention also provides nucleic acid sequences encoding a bispecific antibody molecule of the invention.

It is evident to the skilled person that regulatory sequences may be added to the nucleic acid molecule of the invention. For example, promoters, transcriptional enhancers and/or sequences which allow for induced expression of the polynucleotide of the invention may be employed. A suitable inducible system is for example tetracycline-regulated gene expression as described, e.g., by Gossen and Bujard Proc. Natl. Acad. Sci. USA 89 (1992), 5547-5551 and Gossen et al. Trends Biotech. 12 (1994), 58-62, or a dexamethasone-inducible gene expression system as described, e.g. by Crook EMBO J. 8 (1989), 513-519.

Furthermore, it is envisaged for further purposes that nucleic acid molecules may contain, for example, thioester bonds and/or nucleotide analogues. Said modifications may be useful for the stabilization of the nucleic acid molecule against endo- and/or exonucleases in the cell. Said nucleic acid molecules may be transcribed by an appropriate vector containing a chimeric gene which allows for the transcription of said nucleic acid molecule in the cell. In this respect, it is also to be understood that such polynucleotide can be used for "gene targeting" or "gene therapeutic" approaches. In another embodiment said nucleic acid molecules are labeled. Methods for the detection of nucleic acids are well known in the art, e.g., Southern and Northern blotting, PCR or primer extension. This embodiment may be useful for screening methods for verifying successful introduction of the nucleic acid molecules described above during gene therapy approaches.

Said nucleic acid molecule(s) may be a recombinantly produced chimeric nucleic acid molecule comprising any of the aforementioned nucleic acid molecules either alone or in combination. In the context of the present invention, the nucleic acid molecule is part of a vector.

The present invention therefore also relates to a vector comprising the nucleic acid molecule described in the present invention.

Many suitable vectors are known to those skilled in molecular biology, the choice of which would depend on the function desired and include plasmids, cosmids, viruses, bacteriophages and other vectors used conventionally in genetic engineering. Methods which are well known to those skilled in the art can be used to construct various plasmids and vectors; see, for example, the techniques described in Sambrook et al. (loc cit.) and Ausubel, Current Protocols in Molecular Biology, Green Publishing Associates and Wiley Interscience, N.Y. (1989), (1994). Alternatively, the polynucleotides and vectors of the invention can be reconstituted into liposomes for delivery to target cells. As discussed in further details below, a cloning vector was used to isolate individual sequences of DNA. Relevant sequences can be transferred into expression vectors where expression of a particular polypeptide is required. Typical cloning vectors include pBluescript SK, pGEM, pUC9, pBR322, pGA18 and pGBT9.

Typical expression vectors include pTRE, pCAL-n-EK, pESP-1, pOP13CAT.

The invention also relates to a vector comprising a nucleic acid sequence which is a regulatory sequence operably linked to said nucleic acid sequence encoding a bispecific antibody construct (molecule) defined herein.

Such regulatory sequences (control elements) are known to the skilled person and may include a promoter, a splice cassette, translation initiation codon, translation and insertion site for introducing an insert into the vector. In the context of the present invention, said nucleic acid molecule is operatively linked to said expression control sequences allowing expression in eukaryotic or prokaryotic cells.

It is envisaged that said vector is an expression vector comprising the nucleic acid molecule encoding the bispecific antibody constructs (molecules) defined herein.

The term "regulatory sequence" refers to DNA sequences, which are necessary to effect the expression of coding sequences to which they are ligated. The nature of such control sequences differs depending upon the host organism. In prokaryotes, control sequences generally include promoter, ribosomal binding site, and terminators. In eukaryotes generally control sequences include promoters, terminators and, in some instances, enhancers, transactivators or transcription factors. The term "control sequence" is intended to include, at a minimum, all components the presence of which are necessary for expression, and may also include additional advantageous components.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is obvious for a skilled person that double-stranded nucleic acid is preferably used.

In the context of the present invention the recited vector is an expression vector. An "expression vector" is a construct that can be used to transform a selected host and provides for expression of a coding sequence in the selected host. Expression vectors can for instance be cloning vectors, binary vectors or integrating vectors. Expression comprises transcription of the nucleic acid molecule preferably into a translatable mRNA. Regulatory elements ensuring expression in prokaryotes and/or eukaryotic cells are well known to those skilled in the art. In the case of eukaryotic cells they comprise normally promoters ensuring initiation of transcription and optionally poly-A signals ensuring termination of transcription and stabilization of the transcript. Possible regulatory elements permitting expression in prokaryotic host cells comprise, e.g., the $P_L$, lac, trp or tac promoter in *E. coli*, and examples of regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells.

Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the recited nucleic acid sequence and are well known in the art; see also, e.g., appended examples.

The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including an N-terminal identification peptide imparting desired characteristics, e.g., stabilization or simplified purification of expressed recombinant product; see supra. In this context, suitable expression vectors are known in the art such as Okayama-Berg cDNA expression vector pcDV1 (Pharmacia), pCDM8, pRc/CMV, pcDNA1, pcDNA3 (In-vitrogene), pEF-DHFR, pEF-ADA or pEF-neo (Raum et al. Cancer Immunol Immunother 50 (2001), 141-150) or pSPORT1 (GIBCO BRL).

In the context of the present invention, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and as desired, the collection and purification of the polypeptide of the invention may follow; see, e.g., the appended examples.

An alternative expression system which could be used to express a cell cycle interacting protein is an insect system. In one such system, *Autographa californica* nuclear polyhedrosis virus (AcNPV) is used as a vector to express foreign genes in *Spodoptera frugiperda* cells or in *Trichoplusia* larvae. The coding sequence of a recited nucleic acid molecule may be cloned into a nonessential region of the virus, such as the polyhedrin gene, and placed under control of the polyhedrin promoter. Successful insertion of said coding sequence will render the polyhedrin gene inactive and produce recombinant virus lacking coat protein coat. The recombinant viruses are then used to infect *S. frugiperda* cells or *Trichoplusia* larvae in which the protein of the invention is expressed (Smith, J. Virol. 46 (1983), 584; Engelhard, Proc. Nat. Acad. Sci. USA 91 (1994), 3224-3227).

Additional regulatory elements may include transcriptional as well as translational enhancers. Advantageously, the above-described vectors of the invention comprise a selectable and/or scorable marker.

Selectable marker genes useful for the selection of transformed cells and, e.g., plant tissue and plants are well known to those skilled in the art and comprise, for example, antimetabolite resistance as the basis of selection for dhfr, which confers resistance to methotrexate (Reiss, Plant Physiol. (Life Sci. Adv.) 13 (1994), 143-149), npt, which confers resistance to the aminoglycosides neomycin, kanamycin and paromycin (Herrera-Estrella, EMBO J. 2 (1983), 987-995) and hygro, which confers resistance to hygromycin (Marsh, Gene 32 (1984), 481-485). Additional selectable genes have been described, namely trpB, which allows cells to utilize indole in place of tryptophan; hisD, which allows cells to utilize histinol in place of histidine (Hartman, Proc. Natl. Acad. Sci. USA 85 (1988), 8047); mannose-6-phosphate isomerase which allows cells to utilize mannose (WO 94/20627) and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.) or deaminase from *Aspergillus terreus* which confers resistance to Blasticidin S (Tamura, Biosci. Biotechnol. Biochem. 59 (1995), 2336-2338).

Useful scorable markers are also known to those skilled in the art and are commercially available. Advantageously, said marker is a gene encoding luciferase (Giacomin, Pl. Sci. 116 (1996), 59-72; Scikantha, J. Bact. 178 (1996), 121), green fluorescent protein (Gerdes, FEBS Lett. 389 (1996), 44-47) or β-glucuronidase (Jefferson, EMBO J. 6 (1987), 3901-3907). This embodiment is particularly useful for simple and rapid screening of cells, tissues and organisms containing a recited vector.

As described above, the recited nucleic acid molecule can be used alone or as part of a vector to express the encoded bispecific construct in cells, for, e.g., purification but also for gene therapy purposes, preferably in combination with the transduced CD8+ T-cells. The nucleic acid molecules or vectors containing the DNA sequence(s) encoding any one of the above described bispecific constructs is introduced into the cells which in turn produced the polypeptide of interest. Gene therapy, which is based on introducing therapeutic genes into cells by ex-vivo or in-vivo techniques is one of the most important applications of gene transfer. Suitable vectors, methods or gene-delivery systems for in methods or gene-delivery systems for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813; Verma, Nature 389 (1994), 239; Isner, Lancet 348 (1996), 370-374; Muhlhauser, Circ. Res. 77 (1995), 1077-1086; Onodera, Blood 91 (1998), 30-36; Verma, Gene Ther. 5 (1998), 692-699; Nabel, Ann. N.Y. Acad. Sci. 811 (1997), 289-292; Verzeletti, Hum. Gene Ther. 9 (1998), 2243-51; Wang, Nature Medicine 2 (1996), 714-716; WO 94/29469; WO 97/00957; U.S. Pat. Nos. 5,580,859; 5,589,466; or Schaper, Current Opinion in Biotechnology 7 (1996), 635-640. The recited nucleic acid molecules and vectors may be designed for direct introduction or for introduction via liposomes, or viral vectors (e.g., adenoviral, retroviral) into the cell. In the context of the present invention, said cell is a germ line cell, embryonic cell, or egg cell or derived therefrom, most preferably said cell is a stem cell. An example for an embryonic stem cell can be, inter alia, a stem cell as described in, Nagy, Proc. Natl. Acad. Sci. USA 90 (1993), 8424-8428.

In accordance with the above, the present invention relates to methods to derive vectors, particularly plasmids, cosmids and bacteriophages used conventionally in genetic engineering that comprise a nucleic acid molecule encoding the polypeptide sequence of a bispecific antibody construct defined herein. In the context of the present invention, said vector is an expression vector and/or a gene transfer or targeting vector. Expression vectors derived from viruses such as retroviruses, vaccinia virus, adeno-associated virus, herpes virus, or bovine papilloma virus, may be used for delivery of the recited polynucleotides or vector into targeted cell populations.

Methods which are well known to those skilled in the art can be used to construct recombinant vectors; see, for example, the techniques described in Sambrook et al. (loc cit.), Ausubel (1989, loc cit.) or other standard text books. Alternatively, the recited nucleic acid molecules and vectors can be reconstituted into liposomes for delivery to target cells. The vectors containing the nucleic acid molecules of the invention can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sambrook, supra. The recited vector may, inter alia, be the pEF-DHFR, pEF-ADA or pEF-neo. The vectors pEF-DHFR, pEF-ADA and pEF-neo have been described in the art, e.g. in Mack et al. Proc. Natl. Acad. Sci. USA 92 (1995), 7021-7025 and Raum et al. Cancer Immunol immunother 50 (2001), 141-150.

The invention also provides for a host transformed or transfected with a vector as described herein. Said host may be produced by introducing at least one of the above described vector or at least one of the above described nucleic acid molecules into the host. The presence of said at least one vector or at least one nucleic acid molecule in the host may mediate the expression of a gene encoding the above described bispecific antibody molecules or constructs (i.e., the bispecific antibody molecules described herein).

The described nucleic acid molecule or vector which is introduced in the host may either integrate into the genome of the host or it may be maintained extrachromosomally.

The host can be any prokaryotic or eukaryotic cell.

The term "prokaryote" is meant to include all bacteria which can be transformed, transduced or transfected with DNA or DNA or RNA molecules for the expression of a protein of the invention. Prokaryotic hosts may include gram negative as well as gram positive bacteria such as, for example, *E. coli, S. typhimurium, Serratia marcescens* and *Bacillus subtilis*. The term "eukaryotic" is meant to include yeast, higher plant, insect and preferably mammalian cells. Depending upon the host employed in a recombinant production procedure, the protein encoded by the polynucleotide of the present invention may be glycosylated or may be non-glycosylated. Especially preferred is the use of a plasmid or a virus containing the coding sequence of the polypeptide of the invention and genetically fused thereto an N-terminal FLAG-tag and/or C-terminal His-tag. Preferably, the length of said FLAG-tag is about 4 to 8 amino acids, most preferably 8 amino acids. An above described polynucleotide can be used to transform or transfect the host using any of the techniques commonly known to those of ordinary skill in the art. Furthermore, methods for preparing fused, operably linked genes and expressing them in, e.g., mammalian cells and bacteria are well-known in the art (Sambrook, loc. cit.).

In the context of the present invention, the host (cell) is a bacteria, an insect, fungal, plant or animal cell.

It is particularly envisaged that the recited host may be a mammalian cell, more preferably a human cell or human cell line.

Particularly preferred host cells comprise HEK293, CHO cells, COS cells, myeloma cells lines like SP2/0 or NS/0. As illustrated in the appended examples, particularly preferred are HEK293 cells as hosts.

In a further embodiment, the present invention thus relates to a method for the production of a bispecific antibody molecule or construct (i.e., the bispecific antibody molecule described herein) described above comprising culturing (cultivating) a cell and/or a host cell of the invention under conditions allowing the expression of the bispecific antibody molecule or construct (i.e., the bispecific antibody molecule described herein) and recovering the molecule or construct (i.e., the bispecific antibody molecule described herein) from the cell and/or culture medium.

The transformed hosts can be grown in fermentators and cultured according to techniques known in the art to achieve optimal cell growth. The polypeptide of the invention can then be isolated from the growth medium. The isolation and purification of the, e.g., microbially expressed polypeptides of the invention may be by any conventional means such as, e.g., preparative chromotagraphie separations and immunological separations such as those involving the use of monoclonal or polyclonal antibodies directed, e.g., against a tag of the polypeptide of the invention or as described in the appended examples.

Furthermore, the invention provides a composition (medicament) comprising a bispecific (monoclonal) antibody molecule as defined herein or a (human) bispecific antibody molecule as produced by the method disclosed above, a nucleic acid molecule or the invention, a vector or a host of the invention transduced CD8+ T-cells. In the context of the present invention, said composition is a pharmaceutical composition further comprising, optionally, suitable formulations of carrier, stabilizers and/or excipients.

Furthermore, the invention provides a bispecific antibody molecule as defined herein above for use as a medicament, wherein said bispecific antibody molecule is to be administered before, simultaneously with or after administration of transduced CD8+ T-cells comprising an antigen which does not naturally occur in or on CD8+ T-cells and wherein said CD8+ T-cells were obtained from a subject to be treated.

In the context of the present invention a pharmaceutical composition/medicament is provided that comprises a bispecific antibody molecule as defined herein above which is to be administered in combination with a transduced CD8+ T-cells comprising an antigen which does not naturally occur in or on CD8+ T cells, wherein said bispecific antibody molecule is to be administered before simultaneously with or after administration of transduced CD8+ T-cells comprising an antigen which does not naturally occur in or on CD8+ T cells and wherein said CD8+ T-cells were obtained from a subject to be treated.

In the context of the present invention T-cells are transduced with an antigen that does not naturally occur/that is not endogenously expressed in and/or on T-cells as defined herein above. The invention also relates to CD8+ T-cells that are transduced with an antigen that does not naturally occur/that is not endogenously expressed in and/or on CD8+ T-cells as defined herein above. In the context of the present invention, these transduced T-cells (CD8+ T-cells) further comprise a T-cell receptor (TCR). These transduced T-cells (CD8+ T-cells) are tumor specific either because these T-cells have been isolated from a natural autologous T-cell pool and are able to lyse tumor cells or because these T-cells have been co-transduced with a tumor specific T-cell receptor (TCR). T-cells (CD8+ T-cells) include in the context of the present invention also those capable of recognizing a complex by a T-cell receptor, the complex that is a conjugate of a major histocompatibility gene complex (hereinafter simply referred to as "MHC")-encoding major histocompability antigen molecule (MHC molecule; in case of human, it is called "human leukocyte antigen" (HLA)) and an T-cell receptor specific antigen peptide (which is (structurally) different to the antigen that does not naturally occur in CD8+ T-cells as defined herein above). Accordingly, in the context of the present invention, in order to establish a cytotoxic reaction, it may be necessary that (i) a T-cell (CD8+ T-cell) having a T-cell receptor specific to the HLA-type of a target cell (referring to the tumor cell of the subject to be treated) exists and (ii) an antigen peptide so that a complex formed by binding to the HLA molecule is capable of being recognized by the TCR exists.

The term "T-cell receptor" as used herein refers to any T-cell receptor, provided that the following three criteria are fulfilled: (i) tumor specificity, (ii) recognition of (most) tumor cells, which means that an antigen of target should be expressed in (most) tumor cells and (iii) that the TCR matches to the HLA-type of the subjected to be treated.

In this context, suitable T-cell receptors which fulfils the above mentioned three criteria are known in the art such as WT1 (Wilms tumor specific antigen 1; for sequence information(s) see, e.g., Sugiyama H., Japanese Journal of Clinical Oncology 40 (2010), 377-87), MAGE (for sequence see, e.g., WO 2007/032255 and PCT/US2011/57272), SSX (U.S. Provisional Application No. 61/388,983), NY-ESO-1 (for sequence information(s) see, e.g., PCT/GB2005/001924) and/or HER2neu (for sequence information(s) see WO 2011/0280894).

In the context of the present invention, T-cells (CD8+ T-cells) are isolated/obtained from a subject. Methods for isolating/obtaining T-cells (CD8+ T-cells) from patients are well known in the art and include, without being limiting by leukapheresis from a patient, by isolating/obtaining cells using a FACSort apparatus, by picking living of dead cells from fresh biopsy specimens harbouring living cells by hand or by using micromanipulator (Dudley et al., J. Immunother. 26 (2003), 332-342; Robbins et al., J. Clin. Oncol. 29 (2011), 917-924 and Leisegang, J. Mol. Med. 86 (2008), 573-58). The term "fresh patient biopsy" refers to tumor tissue removed from a subject by surgical or any other known means as well as tumor cell lines or (isolated) cells from a tumor tissue/tumor cell. The isolated/obtained T-cells are subsequently cultivated and expanded by using an anti-CD3 antibody, by using an anti-CD3 and anti-CD28 monoclonal antibodies and/or by using an anti-CD3 antibody, an anti-CD28 antibody and IL-2 (Dudley et al., J. Immunother. 26 (2003), 332-342; Dudley et al., J. Clin. Oncol. 26 (2008), 5233-5239).

In the context of the present invention, these isolated/obtained T-cells are CD8+ T-cells. Methods for identifying the naturally occurring/endogenously expressed antigen/marker on the surface are known in the art and include, without being limiting, flow cytometry (Koch et al., Immunity & Ageing 5 (2008), 6), polymerase-chain-reaction (Fernandes S., Clinical and Diagnostic Laboratory Immunology 12 (2005), 477-483) and confocal microscopy (Kenny E. et al., Immunology 101 (2000), 178-184).

In a subsequent step the T-cells are artificially/genetically modified/transduced by methods known in the art (Francois M. Lemoine et al., J Gene Med 6 (2004), 374-386). Methods for transducing T-cells are known in the art and include, without being limited, in a case where nucleic acid or a recombinant nucleic acid is transduced, for example, an electroporation method, calcium phosphate method, cationic lipid method or liposome method. The nucleic to be transduced can be conventionally and highly efficiently transduced by using a commercially available transfection reagent, for example, Lipofectamine (manufactured by Invitrogene). In a case, where a vector is used, the vector can be transduced in the same manner as the above-mentioned nucleic acid as long as the vector is a plasmid vector. In the context of the present application, the methods for transducing T-cells include retroviral or lentiviral T-cell transduction as well as mRNA transfection.

In this context, suitable (retroviral) vectors for (human) T-cell transduction are known in the art such as SAMEN CMV/SRa (Clay et al., J. Immunol. 163 (1999), 507-513), LZRS-id3-IHRES (Heemskerk et al., J. Exp. Med. 186 (1997), 1597-1602), FeLV (Neil et al., Nature 308 (1984), 814-820), SAX (Kantoff et al., Proc. Natl. Acad. Sci. USA 83 (1986), 6563-6567), pDOL (Desiderio, J. Exp. Med. 167 (1988), 372-388), N2 (Kasid et al., Proc. Natl. Acad. Sci. USA 87 (1990), 473-477), LNL6 (Tiberghien et al., Blood 84 (1994), 1333-1341), pZipNEO (Chen et al., J. Immunol. 153 (1994), 3630-3638), LASN (Mullen et al., Hum. Gene Ther. 7 (1996), 1123-1129), pG1XsNa (Taylor et al., J. Exp. Med. 184 (1996), 2031-2036), LCNX and LXSN (Sun et al., Hum. Gene Ther. 8 (1997), 1041-1048), SFG (Gallardo et al., Blood 90 (1997), 952-957), HMB-Hb-Hu (Vieillard et al., Proc. Natl. Acad. Sci. USA 94 (1997), 11595-11600), pMV7 (Cochlovius et al., Cancer Immunol. Immunother. 46 (1998), 61-66), pSTITCH (Weitjens et al., Gene Ther 5 (1998), 1195-1203), pLZR (Yang et al., Hum. Gene Ther. 10 (1999), 123-132), pBAG (Wu et al., Hum. Gene Ther. 10 (1999), 977-982), rKat.43.267bn (Gilham et al., J. Immunother. 25 (2002), 139-151), pLGSN (Engels et al., Hum. Gene Ther. 14 (2003), 1155-1168), pMP71 (Engels et al., Hum. Gene Ther. 14 (2003), 1155-1168), pGCSAM (Morgan et al., J. Immunol. 171 (2003), 3287-3295), pMSGV (Zhao et al., J. Immunol. 174 (2005), 4415-4423), pMX (de Witte et al., J. Immunol. 181 (2008), 5128-5136).

In accordance with this invention, the term "medicament" is used interchangeably with the term "pharmaceutical composition" and relates to a composition for administration to a patient, preferably a human patient. In the context of the present invention that medicament/pharmaceutical composition is to be administered to a patient from which the CD8+ T-cells were isolated/obtained. In the context of the present invention, the patient refers to human patient. Furthermore, in the context of the present invention that patient suffers from a disease, wherein said disease is a malignant disease, especially cancers/carcinomas of ephithelial, endothelial or mesothelial origin or a cancer of the blood. In the context of the present invention the cancers/carcinomas is selected from the group consisting of gastrointestinal cancer, pancreatic cancer, cholangiocellular cancer, lung cancer, breast cancer, ovarian cancer, skin cancer, oral cancer, gastric cancer, cervical cancer, B and T-cell lymphoma, myeloid leukemia, ovarial cancer, leukemia, lymphatic leukemia, nasopharyngeal carcinoma, colon cancer, prostate cancer, renal cell cancer, head and neck cancer, skin cancer (melanoma), cancers of the genitor-urinary tract, e.g., testis cancer, endothelial cancer, cervix cancer and kidney cancer, cancer of the bile duct, esophagus cancer, cancer of the salivatory glands and cancer of the thyroid gland or other tumorous diseases like haematological tumors, gliomas, sarcomas or osteosarcomas.

In a preferred embodiment, the pharmaceutical composition/medicament comprises a bispecific antibody molecule as defined herein for parenteral, transdermal, intraluminal, intra arterial, intrathecal administration or by direct injection into the tissue or tumor. In the context of the present invention the composition/medicament comprises a bispecific antibody molecule as defined herein that is to be administered before, simultaneously with or after administration of transduced CD8+ T-cells comprising an antigen which is not endogenously expressed/naturally occurred in and/or on the surface of T-cells. In the context of the present invention the pharmaceutical composition/medicament comprising a bispecific antibody molecule as defined herein is to be administered in combination with a transduced CD8+ T-cells comprising an antigen which does not naturally occur in or on CD8+ T-cells, wherein said CD8+ T-cells were obtained from a subject to be treated.

The use of the term "in combination" does not restrict the order in which the components of the treatment regimen are to be administered to the subject. Accordingly, the pharmaceutical composition/medicament described herein encompass the administration of a bispecific antibody molecule as defined herein before, simultaneously with or after administration of transduced CD8+ T-cells comprising an antigen which does not naturally occur/endogenously expressed in or on CD8+ T-cells. "In combination" as used herein also does not restrict the timing between the administration of a bispecific antibody molecule as defined herein before and the transduced CD8+ T cells comprising an antigen which does not naturally occur/endogenously expressed in or on CD8+ T-cells. Thus, when the two components are not administered simultaneously with/concurrently, the administrations may be separated by 1 minute, 5 minutes, 15 minutes, 30 minutes, 45 minutes, 1 hour, 2 hours, 4 hours, 6 hours, 12 hours, 24 hours, 48 hours or 72 hours or by any suitable time differential readily determined by one of skill in art and/or described herein.

In the context of the present invention the term "in combination" also encompasses the situation where the bispecific antibody molecule as defined herein and the transduced CD8+ T-cells comprising an antigen which does not naturally occur/endogenously expressed in and/or on CD8+ T-cells are preincubated together before administration to the subject. Thus, the two components may be preincubated before administration, for example, for 1 minute, 5 minutes, 10 minutes, 15 minutes, 30 minutes, 45 minutes or 1 hour or for any suitable time readily determined by one skilled in the art. The invention, in another preferred embodiment, relates to a treatment regimen, in which the bispecific antibody molecule as defined herein and the transduced CD8+ T-cells comprising an antigen/marker which does not naturally occur/endogenously expressed in and/or on CD8+ T-cells, are to be administered simultaneously with/concurrently. In the context of the present invention, the bispecific antibody molecule as defined herein may be administered after the transduced CD8+ T-cells comprising an antigen which does not naturally occur/endogenously expressed in and/or on CD8+ T-cells has been administered.

Further, "in combination" as used herein does not restrict the disclosed treatment regimens to the administration of a bispecific antibody molecule as defined herein and transduced CD8+ T-cells comprising an antigen which does not naturally occur/endogenously expressed in or on CD8+ T-cells in immediate sequence (i.e., the administration of one of the two components, followed (after a certain time interval) by the administration of the other without the administration and/or practice of any other treatment protocol in between. Therefore, the present treatment regimens also encompass the separate administration of a bispecific antibody molecule as defined herein and transduced CD8+ T-cells comprising an antigen which does not naturally occur/endogenously expressed in or on CD8+ T-cells, wherein the administrations are separated by one or more treatment protocols necessary and/or suitable for the treatment or prevention of the disease, or a symptom thereof. Examples of such intervening treatment protocols include but are not limited to, administration of pain medications; administration of chemotherapeutics, surgical handling of the disease or a symptom thereof. Accordingly, the treatment regimens as disclosed herein encompass the administration of a bispecific antibody molecule as defined herein and a transduced CD8+ T-cells comprising an antigen which does not naturally occur/endogenously expressed in or on CD8+ T-cells together with none, one, or more than one treatment protocol suitable for the treatment or prevention of a disease, or a symptom thereof, as described herein or as known in the art.

It is particular envisaged, that said pharmaceutical composition/medicament is to be administered to a patient via infusion or injection. In the context of the present invention the transduced CD8+ T cells comprising an antigen which does not naturally occur in or on CD8+ T-cells is to be administered to a patient via infusion or injection. Administration of the suitable compositions/medicaments may be effected by different ways, intravenous, intraperitoneal, subcutaneous, intramuscular, topical or intradermal administration.

The pharmaceutical composition/medicament of the present invention may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, etc. Compositions comprising such carriers can be formulated by well known conventional methods. These pharmaceutical compositions can be administered to the subject at a suitable dose. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. Generally, the regimen as a regular administration of the pharmaceutical composition should be in the range of 1 μg to 5 g units per day. However, a more preferred dosage for continuous infusion might be in the range of 0.01 μg to 2 mg, preferably 0.01 μg to 1 mg, more preferably 0.01 μg to 100 μg, even more preferably 0.01 μg to 50 μg and most preferably 0.01 μg to 10 μg units per kilogram of body weight per hour. Particularly preferred dosages are recited herein below. Progress can be monitored by periodic assessment. Dosages will vary but a preferred dosage for intravenous administration of DNA is from approximately $10^6$ to $10^{12}$ copies of the DNA molecule. The compositions of the invention may be administered locally or systematically. Administration will generally be parenterally, e.g., intravenously; DNA may also be administered directed to the target site, e.g., by biolistic delivery to an internal or external target site or by catheter to a site in an artery. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the pharmaceutical composition of the present invention might comprise proteinaceous carriers, like, e.g., serum albumine or immunoglobuline, preferably of human origin. It is envisaged that the pharmaceutical composition of the invention might comprise, in addition to the proteinaceous bispecific antibody constructs or nucleic acid molecules or vectors encoding the same (as described in this invention), further biologically active agents, depending on the intended use of the pharmaceutical composition. Such agents might be drugs acting on the gastro-intestinal system, drugs acting as cytostatica, drugs preventing hyperurikemia, drugs inhibiting immunereactions (e.g. corticosteroids), drugs acting on the circulatory system and/or agents such as T-cell co-stimulatory molecules or cytokines known in the art.

Possible indication for administration of the composition (s)/medicament(s) of the invention are malignant diseases especially epithelial cancers/carcinomas such as breast cancer, colon cancer, prostate cancer, head and neck cancer, skin cancer (melanoma), cancers of the genitor-urinary tract, e.g., ovarial cancer, testis cancer, endothelial cancer, cervix cancer and kidney cancer, lung cancer, gastric cancer, cancer of the bile duct, esophagus cancer, cancer of the salivatory glands and cancer of the thyroid gland or other tumorous diseases like haematological tumors, gliomas, sarcomas or osteosarcomas.

The invention further envisages the co-administration protocols with other compounds, e.g., molecules capable of providing an activation signal for immune effector cells, for cell proliferation or for cell stimulation. Said molecule may be, e.g., a further primary activation signal for T-cells (e.g. a further costimulatory molecule: molecules of B7 family, Ox40L, 4.1 BBL, CD40L, anti-CTLA-4, anti-PD-1), or a further cytokine interleukin (e.g., IL-2).

The composition of the invention as described above may also be a diagnostic composition further comprising, optionally, means and methods for detection.

The bispecific binding molecules or constructs (i.e., the bispecific antibody molecules described herein) provided herein are also suited for use in immunoassays in which they can be utilized in liquid phase or bound to a solid phase carrier. Examples of immunoassays which can utilize the polypeptide of the invention are competitive or non-competitive immunoassays in either a direct or indirect format. Examples of such immunoassays are the enzyme linked immunosorbent assay (ELISA), enzyme immunoassay (EIA), radioimmunoassay (RIA), the sandwich (immunometric assay) and the Western blot assay.

The bispecific binding molecules or constructs (i.e., the bispecific antibody molecules described herein) of the invention can be bound to many different carriers and used to isolate cells specifically bound to said polypeptides. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble, e.g. as beads, for the purposes of the invention.

There are many different labels and methods of labeling known to those of ordinary skill in the art. Examples of the types of labels which can be used in the present invention include enzymes, radioisotypes, colloidal metals, fluorescent compounds, chemiluminescent compounds, and bioluminescent compounds.

In a most preferred embodiment of the present invention, the bispecific antibody constructs/molecules of the invention for use as a medicament is envisaged. In the context of the present invention, the bispecific antibody molecules for use as a medicament are described, wherein said bispecific antibody molecule is to be administered before, simultaneously with or after administration of transduced $CD8^+$ T-cells comprising an antigen which does not naturally occur in or on $CD8^+$ T cells and wherein said $CD8^+$ T-cells were obtained from a subject to be treated. Said medicament may be employed in a method of treatment of malignant diseases especially cancers/carcinomas of epithelial, endothelial or mesothelial origin or of the blood. In the context of the present invention the cancer/carcinoma is selected from the group consisting of gastrointestinal cancer, pancreatic cancer, cholangiocellular cancer, lung cancer, breast cancer, ovarian cancer, skin cancer, oral cancer, gastric cancer, cervical cancer, B and T-cell lymphoma, myeloid leukemia, ovarial cancer, leukemia, lymphatic leukemia, nasopharyngeal carcinoma, colon cancer, prostate cancer, renal cell cancer, head and neck cancer, skin cancer (melanoma), cancers of the genitor-urinary tract, e.g., testis cancer, ovarial cancer, endothelial cancer, cervix cancer and kidney cancer, cancer of the bile duct, esophagus cancer, cancer of the salivatory glands and cancer of the thyroid gland or other tumorous diseases like haematological tumors, gliomas, sarcomas or osteosarcomas.

Furthermore, in the context of the present invention a bispecific antibody molecule as described herein which comprises (i) a first binding domain binding an antigen on CD8+ T-cells that does not naturally occur in or on CD8+ T-cells; and (ii) a second binding domain binding a tumor-specific antigen naturally occurring on the surface of a tumor cell for use in a method of treating a malignant disease is envisaged, wherein said bispecific antibody molecule is to be administered before, simultaneously with or after administration of transduced CD8+ T-cells comprising an antigen which does not naturally occur in or on CD8+ T cells and wherein said CD8+ T-cells were obtained from a subject to be treated.

Furthermore, in the context of the present invention a method of treatment of a malignant disease, the method comprising the administration of a bispecific antibody molecule of the present invention to a subject in need thereof which comprises (i) a first binding domain binding an antigen on CD8+ T-cells that does not naturally occur in or on CD8+ T-cells; and (ii) a second binding domain binding a tumor-specific antigen naturally occurring on the surface of a tumor cell; wherein said bispecific antibody molecule is to be administered before, simultaneously with or after administration of transduced CD8+ T-cells from said subject comprising an antigen which does not naturally occur in or on CD8+ T cells. In the context of the present invention the cancer/carcinoma is selected from the group consisting of of gastrointestinal cancer, pancreatic cancer, cholangiocellular cancer, lung cancer, breast cancer, ovarian cancer, skin cancer, oral cancer, gastric cancer, cervical cancer, B and T-cell lymphoma, myeloid leukemia, ovarial cancer, leukemia, lymphatic leukemia, nasopharyngeal carcinoma, colon cancer, prostate cancer, renal cell cancer, head and neck cancer, skin cancer (melanoma), cancers of the genitor-urinary tract, e.g., testis cancer, ovarial cancer, endothelial cancer, cervix cancer and kidney cancer, cancer of the bile duct, esophagus cancer, cancer of the salivatory glands and cancer of the thyroid gland or other tumorous diseases like haematological tumors, gliomas, sarcomas or osteosarcomas.

Furthermore, in accordance to the invention, a molecule or construct (i.e., the bispecific antibody molecule described herein) comprising (human) EpCAM (as the tumor-specific antigen naturally occurring on the surface of a tumor cell) and one of the herein defined antigens that does not naturally occur in and/or on T-cells (CD8+ T-cells) can be used in a method for the treatment of gastrointestinal cancer, pancreatic cancer, cholangiocellular cancer, lung cancer, breast cancer, ovarian cancer, skin cancer and/or oral cancer. In the context of the present invention a bispecific antibody molecule directed against (human) EpCAM (as second binding domain) and comprises a first binding domain directed against/binding to/interacting with Cripto may be used in the treatment of gastrointestinal cancer, for example adenocarcinoma of gastrointestinal origin. A molecule or construct (i.e., the bispecific antibody molecule described herein)

comprising (human) HER1 (as the tumor-specific antigen naturally occurring on the surface of a tumor cell) and one of the herein defined antigens that does not naturally occur in and/or on T-cells (CD8+ T-cells) can be used in a method for the treatment of gastrointestinal cancer, pancreatic cancer, cholangiocellular cancer, lung cancer, breast cancer, ovarian cancer, skin cancer and/or oral cancer. A molecule or construct (i.e., the bispecific antibody molecule described herein) comprising (human) HER2 (as the tumor-specific antigen naturally occurring on the surface of a tumor cell) and one of the herein defined antigens that does not naturally occur in and/or on T-cells (CD8+ T-cells) can be used in a method for the treatment of gastric cancer, breast cancer and/or cervical cancer. A molecule or construct (i.e., the bispecific antibody molecule described herein) comprising (human) HER3 (as the tumor-specific antigen naturally occurring on the surface of a tumor cell) and one of the herein defined antigens that does not naturally occur in and/or on T-cells (CD8+ T-cells) can be used in a method for the treatment of gastric cancer and/or lung cancer. A molecule or construct (i.e., the bispecific antibody molecule described herein) comprising (human) CD20 as the tumor-specific antigen naturally occurring on the surface of a tumor cell) and one of the herein defined antigens that does not naturally occur in and/or on T-cells (CD8+ T-cells) can be used in a method for the treatment of B-cell lymphoma and/or T-cell lymphoma. A molecule or construct (i.e., the bispecific antibody molecule described herein) comprising (human) CD22 (as the tumor-specific antigen naturally occurring on the surface of a tumor cell) and one of the herein defined antigens that does not naturally occur in and/or on T-cells (CD8+ T-cells) can be used in a method for the treatment of B-cell lymphoma and/or T-cell lymphoma. A molecule or construct (i.e., the bispecific antibody molecule described herein) comprising (human) CD33 (as the tumor-specific antigen naturally occurring on the surface of a tumor cell) and one of the herein defined antigens that does not naturally occur in and/or on T-cells (CD8+ T-cells) can be used in a method for the treatment of myeloid leukemia. A molecule or construct (i.e., the bispecific antibody molecule described herein) comprising (human) CA12-5 (as the tumor-specific antigen naturally occurring on the surface of a tumor cell) and one of the herein defined antigens that does not naturally occur in and/or on T-cells (CD8+ T-cells) can be used in a method for the treatment of ovarian cancer, lung cancer, breast cancer and/or gastrointestinal cancer. A molecule or construct (i.e., the bispecific antibody molecule described herein) comprising (human) HLA-DR (as the tumor-specific antigen naturally occurring on the surface of a tumor cell) and one of the herein defined antigens that does not naturally occur in and/or T-cells (CD8+ T-cells) can be used in a method for the treatment of gastrointestinal cancer, leukemia and/or nasopharyngeal carcinoma. A molecule or construct (i.e., the bispecific antibody molecule described herein) comprising (human) MUC-1 (as the tumor-specific antigen naturally occurring on the surface of a tumor cell) and one of the herein defined antigens that does not naturally occur in and/or on T-cells (CD8+ T-cells) can be used in a method for the treatment of colon cancer, breast cancer, ovarian cancer, lung cancer and/or pancreatic cancer. A molecule construct (i.e., the bispecific antibody molecule described herein) comprising (human) A33 (as the tumor-specific antigen naturally occurring on the surface of a tumor cell) and one of the herein defined antigens that does not naturally occur in and/or on T-cells (CD8+ T-cells) can be used in a method for the treatment of colon cancer. A molecule or construct (i.e., the bispecific antibody molecule described herein) comprising (human) PSMA (as the tumor-specific antigen naturally occurring on the surface of a tumor cell) and one of the herein defined antigens that does not naturally occur in and/or on T-cells (CD8+ T-cells) can be used in a method for the treatment of prostate cancer. A molecule or construct (i.e., the bispecific antibody molecule described herein) comprising (human) transferrin receptor (as the tumor-specific antigen naturally occurring on the surface of a tumor cell) and one of the herein defined antigens that does not naturally occur in and/or on T-cells (CD8+ T-cells) can be used in a method for the treatment of gastrointestinal cancer, pancreatic cancer, cholangiocellular cancer, lung cancer, breast cancer, ovarian cancer, skin cancer and/or oral cancer. A molecule or construct (i.e., the bispecific antibody molecule described herein) comprising (human) CA-IX (as the tumor-specific antigen naturally occurring on the surface of a tumor cell) and one of the herein defined antigens that does not naturally occur in and/or on T-cells (CD8+ T-cells) can be used in a method for the treatment of renal cancer.

The invention also relates to a method for the treatment of a disease, a malignant disease such as cancer of epithelial, endothelial or mesothelial origin and/or cancer of blood. Such diseases would be among others: cancer of esophagus, stomach, colon, small bowel, liver, pancreas, breast, lungs, brain, kidney, testis, skin cancer, leukemias and/or lymphonas comprising the administration the transduced CD8+ T-cells to a subject. In the context of the present invention, said subject is a human.

In the context of the present invention a method for the treatment of a disease is described that comprises the steps of (a) isolating CD8+ T-cells from a subject;
(b) transducing said isolated CD8+ T-cells with an antigen which does not naturally occur in CD8+ T-cells as described herein above; and
(c) administering the transduced CD8+ T-cells to said subject.

In the context of the present invention, said transduced CD8+ T-cells are administered to said subject by intravenous infusion.

Moreover, the present invention provides a method for the treatment of a disease comprising the steps of (a) isolating CD8+ T-cells from a subject;
(b) transducing said isolated CD8+ T-cells with an antigen which does not naturally occur in CD8+ T-cells as described herein above;
(c) co-transducing said isolated CD8+ T-cells with a T-cell receptor;
(d) expanding the CD8+ T-cells by anti-CD3 and anti-CD28 antibodies; and
(e) administering the transduced CD8+ T-cells to said subject.

The present invention relates to isolated CD8+ T-cells that are analyzed by methods in order to make sure that the (tumor) antigen that naturally occurs on the isolated CD8+ T-cells is identical to the tumor antigen to which the bispecific antibody described herein bind via its second binding domain. In the context of the present invention the isolated/obtained CD8+ T-cells (comprising an antigen that naturally occurs on the surface of the isolated CD8+ T-cells) are artificially modified by introducing an antigen/marker that does not naturally occur/that is not naturally expressed in and/or on CD8+ T-cells. In the context of the present invention, the artificial modification of the isolated/obtained CD8+ T-cells relates to transduction methods described herein. Accordingly, in the context of the present invention, the subject to be treated, relates to a subject being characterized by suffering from a disease characterized by having a tumor-specific antigen naturally occurring on the surface of a tumor cell as described herein above. In the context of the present invention the administration of the transduced CD8+ T-cells obtained/isolated from the subject to be treated will be performed by intravenous infusion.

In a further embodiment, the present invention relates to a method for the treatment of a disease comprising the steps of (a) isolating tumor infiltrated lymphocytes (TIL) from a resected tumor from the patient;
(b) culturing and transduction of TIL with an antigen which does not naturally occur in CD8+ T-cells as described herein above;
(c) selecting TIL cultures on the basis of functional tumor recognition assays;
(d) expanding the TIL by anti-CD3 and/or anti-CD28 antibodies; and
(e) administering the transduced CD8+ T-cells to said subject.

The term "functional tumor recognition" assays means coculture of TIL with either autologous, e.g. patient's, tumor cells or a cell line of identical HLA-type. The read out is the cytotoxic activity to the tumor cell (LDH, calcein-release). Further read outs could be cytokine secretion, flow cytometry of T-cells for the presence of intracellular cytokines, ELISPOT assays.

The above mentioned step (d) (referring to the expanding step of the TIL by anti-CD3 and/or anti-CD28 antibodies) may also be performed in the presence of (stimulating) cytokines such as interleukin-2 and/or interleukin-15 (IL-15). In the context of the present invention, the above mentioned step (d) (referring to the expanding step of the TIL by anti-CD3 and/or anti-CD28 antibodies) may also be performed in the presence of interleukin-12 (IL-12), interleukin-7 (IL-7) and/or interleukin-21 (IL-21).

The method for the treatment may also, in addition, comprise the administration of the bispecific (monoclonal) antibody of the present invention. Said (monoclonal) bispecific antibody may be administered before, simultaneously with or after the transduced CD8+ T-cells are to be administered. In the context of the present invention the administration of the transduced CD8+ T-cells will be performed by intravenous infusion. In the context of the present invention that transduced CD8+ T-cells are isolated/obtained from the subject to be treated.

The invention provides a kit comprising the bispecific (monoclonal) antibody, a nucleic acid molecule, a vector or a host of the invention. Said kit is particularly useful in the preparation of a pharmaceutical composition of the present invention and may, inter alia, consist of a container useful for injections or infusions. Advantageously, the kit of the present invention further comprises, optionally (a) buffer(s), storage solutions and/or remaining reagents or materials required for the conduct of medical or scientific purposes. The present invention relates to a kit comprising (A) a bispecific antibody molecule comprising (i) a first binding domain binding an antigen on CD8+ T-cells that does not naturally occur in or on CD8+ T-cells; and a second binding domain binding a tumor-specific antigen naturally occurring on the surface of a tumor cell; and (B) material required for transducing CD8+ T-cells isolated/obtained from a subject to be treated with an antigen that does not naturally occur in or on said CD8+ T-cells.

In the context of the present invention the "material required for transducing CD8+ T-cells" isolated/obtained from a subject to be treated is at least a nucleic acid encoding an antigen that does not naturally occur/that is not endogenously expressed in and/or on CD8+ T-cells. The nucleic acid encoding an antigen that does not naturally occur/that is not endogenously expressed in and/or on CD8+ T-cells may be operably linked to (a) regulatory sequence(s) which are usually carried within a vector (e.g., a plasmid or viral DNA) which includes sequences that are necessary for in vitro selection and amplification of the vector in a bacteria. A vector allowing the expression of the antigen that does not naturally occur/that is not endogenously expressed in CD8+ T-cells is referred to herein as an "expression vector". Thus, another useful "material required for transducing CD8+ T-cells" isolated/obtained from a subject to be treated may be a vector/expression vector comprising at least a nucleic acid encoding an antigen that does not naturally occur in and/or on CD8+ T-cells. In this context, suitable vectors for T-cell/CD8+ T-cell transduction encompass the vector selected from the group consisting of SAMEN CMV/SRa (Clay et al., J. Immunol. 163 (1999), 507-513), LZRS-id3-IHRES (Heemskerk et al., J. Exp. Med. 186 (1997), 1597-1602), FeLV (Neil et al., Nature 308 (1984), 814-820), SAX (Kantoff et al., Proc. Natl, Acad. Sci. USA 83 (1986), 6563-6567), pDOL (Desiderio, J. Exp. Med. 167 (1988), 372-388), N2 (Kasid et al., Proc. Natl. Acad. Sci. USA 87 (1990), 473-477), LNL6 (Tiberghien et al., Blood 84 (1994), 1333-1341), pZipNEO (Chen et al., J. Immunol. 153 (1994), 3630-3638), LASN (Mullen et al., Hum. Gene Ther. 7 (1996), 1123-1129), pG1XsNa (Taylor et al., J. Exp. Med. 184 (1996), 2031-2036), LCNX and LXSN (Sun et al., Hum. Gene Ther. 8 (1997), 1041-1048), SFG (Gallardo et al., Blood 90 (1997), 952-957), HMB-Hb-Hu (Vieillard et al., Proc. Natl. Acad. Sci. USA 94 (1997), 11595-11600), pMV7 (Cochlovius et al., Cancer Immunol. Immunother. 46 (1998), 61-66), pSTITCH (Weitjens et al., Gene Ther 5 (1998), 1195-1203), pLZR (Yang et al., Hum. Gene Ther. 10 (1999), 123-132), pBAG (Wu et al., Hum. Gene Ther. 10 (1999), 977-982), rKat.43.267bn (Gilham et al., J. Immunother. 25 (2002), 139-151), pLGSN (Engels et al., Hum. Gene Ther. 14 (2003), 1155-1168), pMP71 (Engels et al., Hum. Gene Ther. 14 (2003), 1155-1168), pGCSAM (Morgan et al., J. Immunol. 171 (2003), 3287-3295), pMSGV (Zhao et al., J. Immunol. 174 (2005), 4415-4423) and pMX (de Witte et al., J. Immunol. 181 (2008), 5128-5136). The "material required for transducing CD8+ T-cells" may also encompass a host cell transformed or transfected with a vector as a tool for the expression of the antigen that does not naturally occur/that is not endogenously expressed in and/or on CD8+ T-cells. Said host cell may be produced by introducing at least one of the above described vectors or at least a nucleic acid molecule encoding an antigen that does not naturally occur/that is not endogenously expressed in and/or on CD8+ T-cells into the host cell. The presence of said at least one vector or at least one nucleic acid in the host cell may mediate the expression of a gene encoding the herein described antigen that does not naturally occur/that is not endogenously expressed in and/or on CD8+ T-cells.

The material required for transducing CD8+ T-cells can further encompass detailed information and/or equipment necessary in connection with the genetical/artificial modification/transduction of these isolated/obtained CD8+ T-cells. If a nucleic acid or a recombinant nucleic acid encoding an antigen that does not naturally occur/that is not endogenously expressed in and/or on CD8+ T-cells is used for the transduction of CD8+ T-cells, information and/or equipment necessary for an electroporation method, calcium phosphate method, cationic lipid method, liposome method like (a)

transfection reagent(s), buffer(s) and/or remaining reagents required for the transduction may be provided in the kit.

The material required for transducing CD8+ T-cells can further encompass information and/or equipment necessary in connection with the cultivation and expansion of the isolated/obtained CD8+ T cells, such as an anti-CD3 antibody, an anti-CD3 and anti-CD28 monoclonal antibody and/or an anti-CD3 antibody, an anti-CD28 antibody and IL-2.

Thus, in summary, the "material required for transducing CD8+ T-cells" isolated/obtained from a subject to be treated is at least a nucleic acid encoding an antigen that does not naturally occur in and/or on CD8+ T-cells, a vector/expression vector comprising at least a nucleic acid encoding an antigen that does not naturally occur in and/or on CD8+ T cells, transfection reagent(s), buffer(s) and/or material required for the transduction and/or cultivation of CD8+ T-cells isolated/obtained from a subject to be treated with an antigen that does not naturally occur in and/or on said CD8+ T-cells.

Furthermore, parts of the kit of the invention can be packaged individually in vials or bottles or in combination in containers or multicontainer units. Furthermore, the kit of the present invention comprises a (closed) bag cell incubation system where patient cells, preferably T-cells as described herein above, can be transduced and incubated under GMP (good manufacturing practice, as described in the guidelines for good manufacturing practice published by the European Commission under europa.eu/health/documents/eudralex/indexen.htm) conditions. Furthermore, the kit of the present invention comprises a (closed) bag cell incubation system where isolated/obtained patients CD8+ T cells can be transduced and incubated under GMP. Furthermore, in the context of the present invention, the kit may also comprise a nucleic acid molecule encoding an antigen that does not naturally occur in CD8+ T-cells as described herein above and/or a nucleic acid molecule encoding a T-cell receptor as described herein above. The kit of the present invention may be advantageously used, inter alia, for carrying out the method of the invention and could be employed in a variety of applications referred herein, e.g., as research tools or medical tools. The manufacture of the kits preferably follows standard procedures which are known to the person skilled in the art.

These and other embodiments are disclosed and encompassed by the description and Examples of the present invention. Further literature concerning any one of the antibodies, methods, uses and compounds to be employed in accordance with the present invention may be retrieved from public libraries and databases, using for example electronic devices. For example, the public database "Medline", available on the Internet, may be utilized, for example under www.ncbi.nlm.nih.gov/PubMed/medline.html. Further databases and addresses, such as www.ncbi.nlm.nih.gov/, infobiogen.fr/, fmi.ch/biology/researchtools.html, tigr.org/, are known to the person skilled in the art and can also be obtained using, e.g., www.lycos.com.

The figures show:

FIG. 1: A representative bispecific antibody that comprises specificities for human EGFR as well as for murine EpCAM (MAb225_scFv_G8.8)

MAb225 with a murine IgG2a backbone has a fusion of a single-chain (sc) Fv fragment at the C-terminus of the heavy chains.

Figure 2:
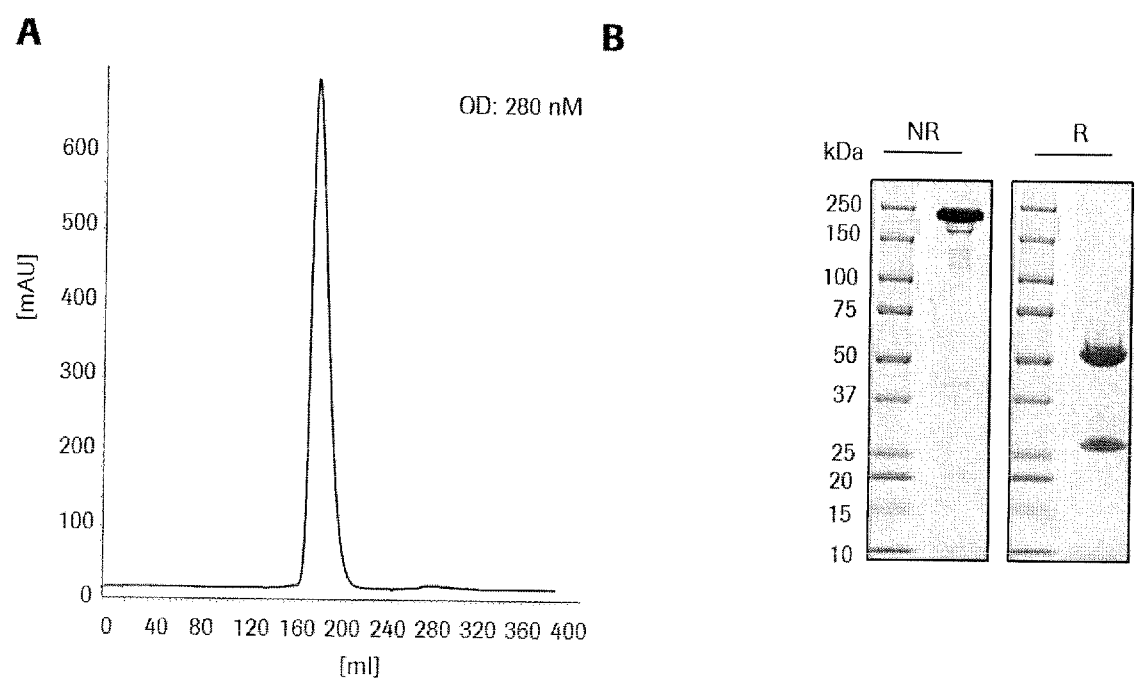

FIG. 2: A representative SEC and SDS-PAGE picture of the human EGFR-specific antibody MAb225

Protein A purified antibody was subjected to size exclusion chromatography. (A) Elution profile from a HiLoad Superdex 200 column. Peak fractions were pooled and protein purity was assessed by SDS-PAGE. (B) Non-reducing (NR) and reducing (R) SDS-PAGE of the bispecific antibody.

FIG. 3: A representative SEC and SDS-PAGE picture of the mouse EpCAM-specific antibody G8.8

Protein A purified antibody was subjected to size exclusion chromatography. (A) Elution profile from a HiLoad Superdex 200 column. Peak fractions were pooled and protein purity was assessed by SDS-PAGE. (B) Non-reducing (NR) and reducing (R) SDS-PAGE of the bispecific antibody.

Figure 4:
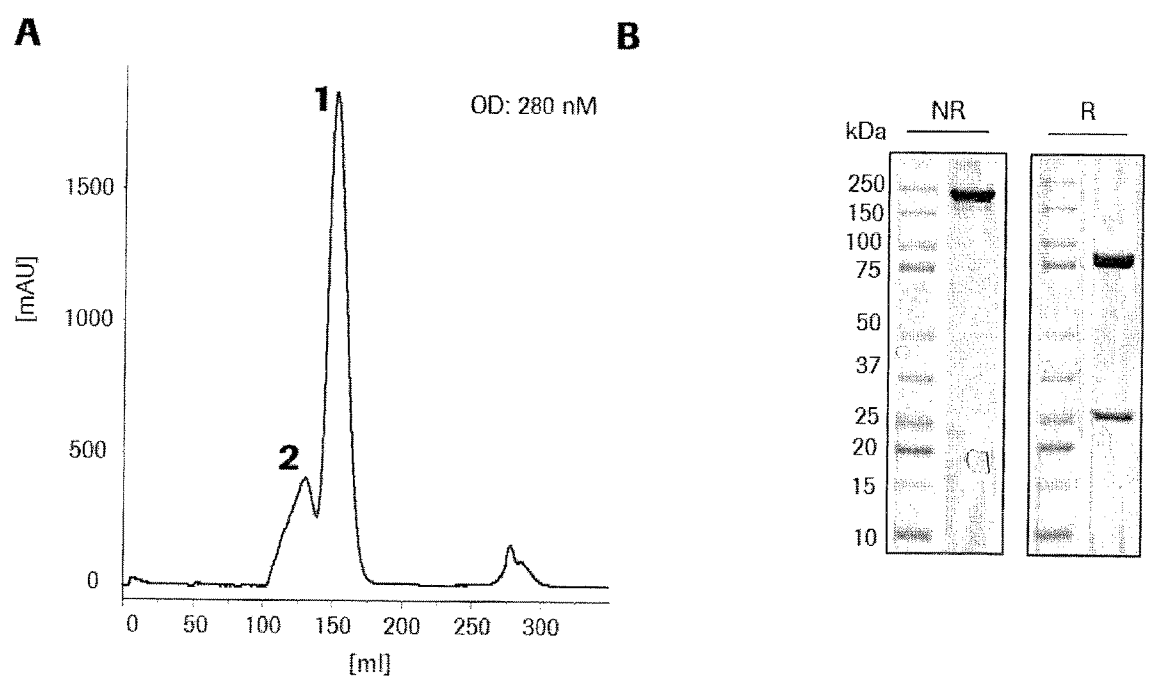

FIG. 4: A representative SEC and SDS-PAGE picture of the bispecific antibody MAb225_scFv_G8.8

(A) Elution profile from a HiLoad Superdex 200 column. Indicated numbers refer to bispecific antibody fraction (1) and aggregate fraction (2). Peak fractions (1) were pooled and protein purity was assessed by SDS-PAGE. (B) Non-reducing (NR) and reducing (R) SDS-PAGE of the bispecific antibody.

Figure 5:
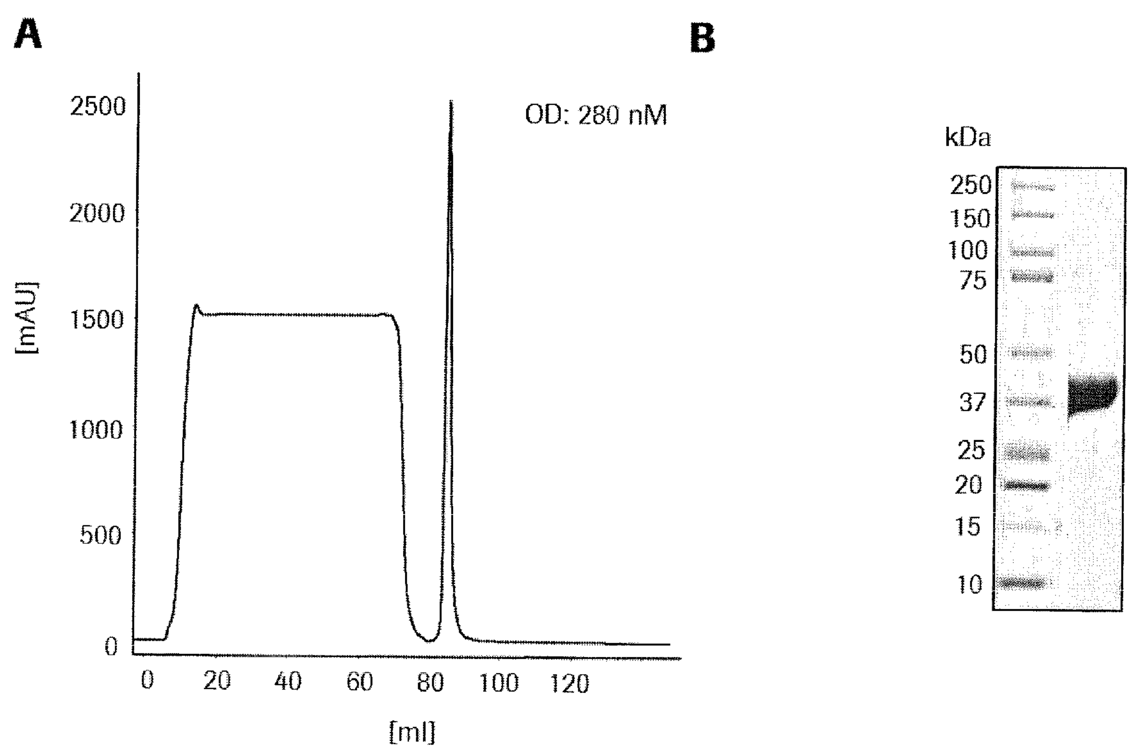

FIG. 5: Affinity chromatography and SDS-PAGE of murine EpCAM ECD

Cell culture supernatants containing murine EpCAM with a C-terminal Histidine epitope tag were purified using Ni-chelate chromatography. (A) Elution profile from HisTrap FF column. (B) SDS-PAGE analysis of the dialysed protein under reducing conditions. The gel was stained with Coomassie Brilliant Blue dye.

Figure 6:
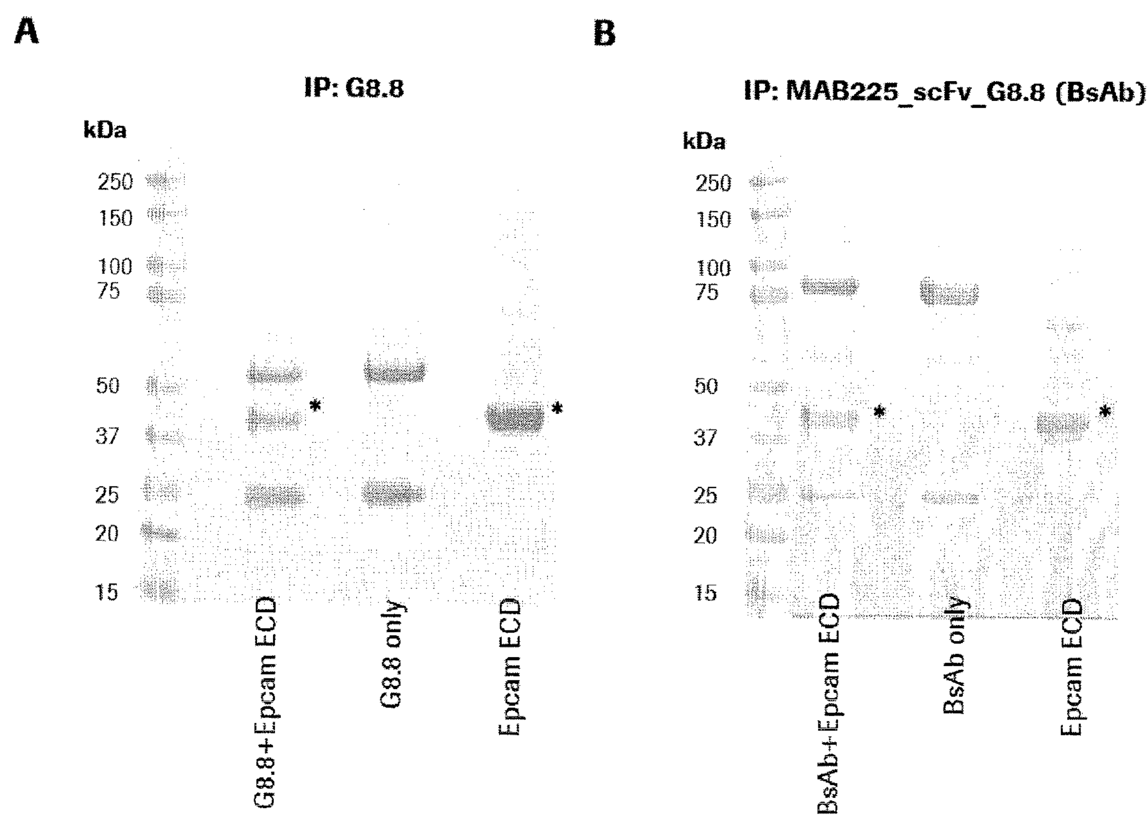

FIG. 6: Interaction of recombinant murine EpCAM ECD with EpCAM-specific antibodies Recombinant murine EpCAM does interact with G8.8 or bispecific antibody MAB225_scFv_G8.8. (A) Recombinant EpCAM was immunoprecipitated with G8.8. Asterisk indicates EpCAM. (B) Recombinant EpCAM was immunoprecipitated with MAB225_scFv_G8.8. Asterisk indicates EpCAM.

FIG. 7: Schematic overview of the new therapeutic principle by recruiting tumor specific T-cells to a tumor through a bispecific antibody T-cells (here transgenic murine TCR-I T-cells; TCR tg T-cell) carry a T-cell receptor for the immunodominant epitope 1 of the large T antigen (TCR T spec.). These T-cells are additionally transduced with a marker antigen (del-hEGFR; SEQ ID NOs: 11 and 12). The targeted tumor cell naturally expresses the large T antigen which is presented in the context of major-histocompatibility-complex (MHC) and the tumor antigen (EpCAM). A bispecific antibody (MAb225_scFv_G8.8) with an antigen binding site for del-hEGFR on one arm and for (murine) EpCAM on the other arm brings both cell types together. The tumor peptide specific TCR, the tumor peptide and the MHC form an "immunological synapse".

Figure 8:
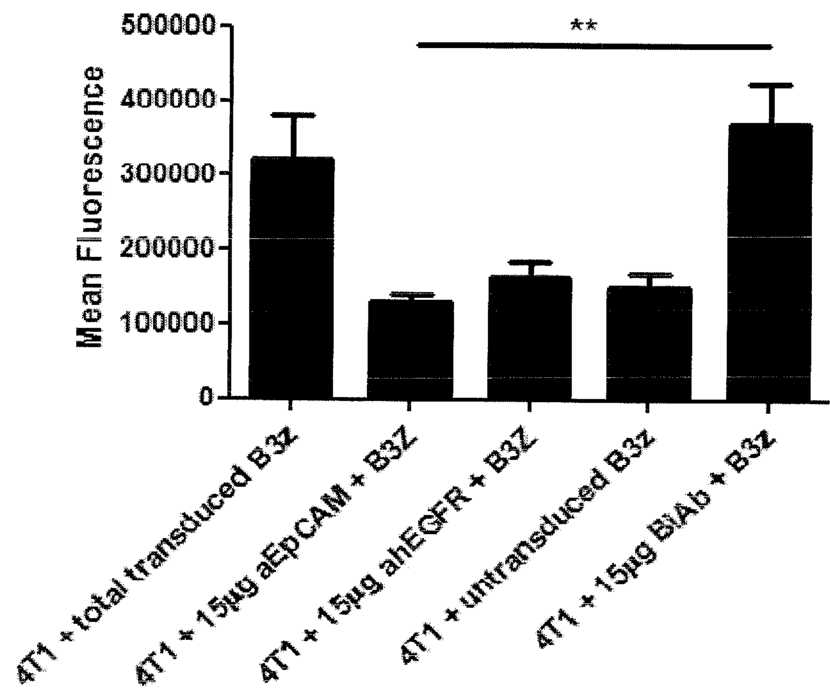

FIG. 8: Transduction efficiency of primary T-cells with del-hEGFR

Primary murine T-cells were retrovirally transduced with the del-hEGFR (SEQ ID NOs: 11 and 12). Flow cytometric analysis revealed an efficient transduction with the del-hEGFR (dark curve) compared to untransduced T-cells (light curve).

Figure 9:
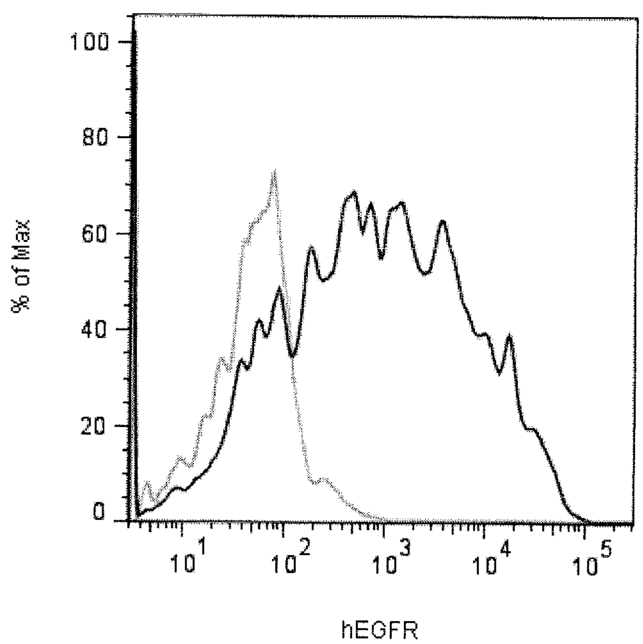

FIG. 9: Cross-linking of transduced T-cells with tumor cells through a bispecific antibody EpCAM expressing 4T1 cells were seeded and grown to confluency. Del-hEGFR-transduced B3Z T-cells (permanent cell line, fluorescently labeled) were preloaded with the bispecific antibody (MAb225_scFv_G8.8) and subsequently incubated in the plate with the adherent 4T1. After thorough washing, remaining cells were lysed and remaining fluorescence was measured. The bispecific antibody against EpCAM and hEFGR or monospecific antibodies (anti-EpCAM and anti-hEGFR as controls) were added. The bispecific antibody retained significantly more transduced cells in the flask than any of the controls. ** indicates p<0.01 for all comparisons.

Figure 10:
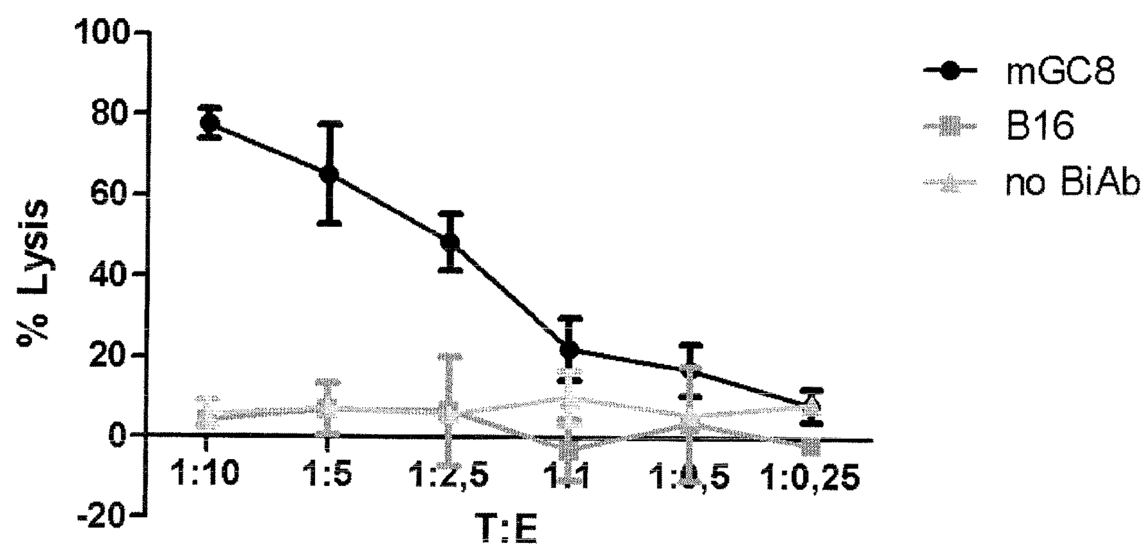

FIG. 10: Bispecific antibody-retargeted T-cell-mediated lysis of tumor cells Tumor specific T-cells (TCR-I, T-cells transgenic for T-cell receptor recognizing the immunodominant epitope of the large T antigen) were transduced with del-hEGFR (SEQ ID NOs: 11 and 12) and were preincubated with the bispecific antibody (MAb225_scFv_G8.8 (SEQ ID NOs: 5 and 6)). mGC8 tumor cells (permanent cell line) expressing EpCAM and the large T antigen or B16 tumor cells expressing neither were fluorescently labeled (with calcein). Cells were cultured at the indicated tumor-to-T-cell ratios (T:E) together over night and lysis of cells was quantified by measuring the fluorescence released. A target-to-effector ratio dependent lysis was induced in the mGC8 cells but not in the B16 cells.

Figure 11:
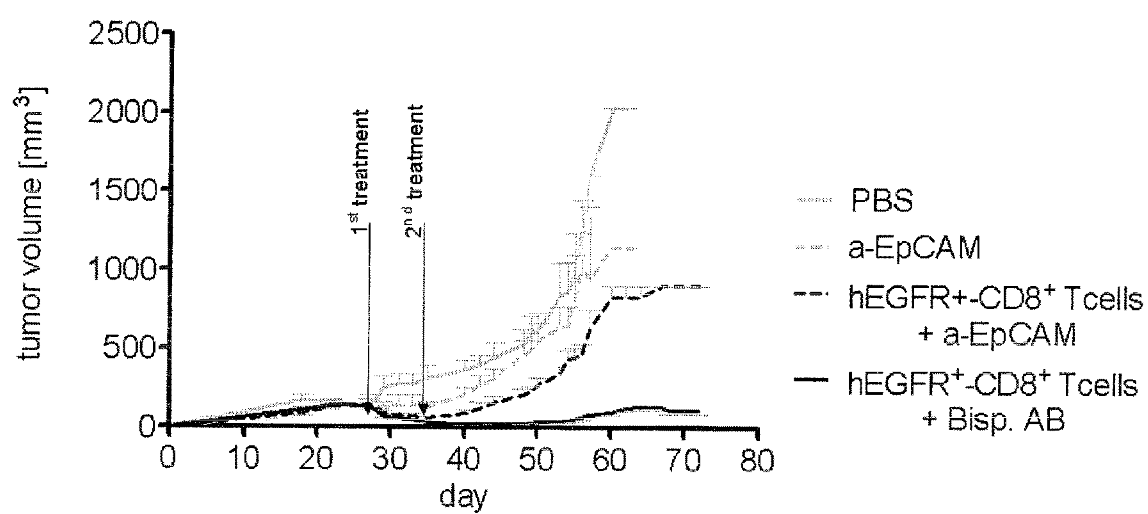

FIG. 11: Treatment of established tumors by the combination of a bispecific antibody and transduced tumor specific T-cells Mice were challenged with a subcutaneous tumor (mGC8 cell line). Mice were treated (i.v. for cell administration; i.v. and i.p. for antibody administration) at the indicated time points with either PBS, an anti-EpCAM mono-specific antibody (EpCAM G8.8 (SEQ ID NOs: 3 and 4)) alone, the transduced T-cells (CD8+ T-cells) with anti-EpCAM monospecific antibody (EpCAM G8.8 (SEQ ID NOs: 3 and 4)) and with anti-EGFR mono-specific antibody (EGFR MAb225 (SEQ ID NOs: 1 and 2)) or with the transduced T-cells (CD8+ T-cells) with the bispecific antibody (MAb225_scFv_G8.8; specific for EpCAM and EGFR (SEQ ID NOs: 5 and 6)). This combination treatment induced a significant reduction and delay in tumor growth when compared to any of the other treatment groups. Differences in tumor volume were significant from day 31 for group 1 versus 4, from day 40 for group 2 versus 4 and from day 50 for group 3 versus 4 (p<0.001 for all comparisons).

Figure 12:
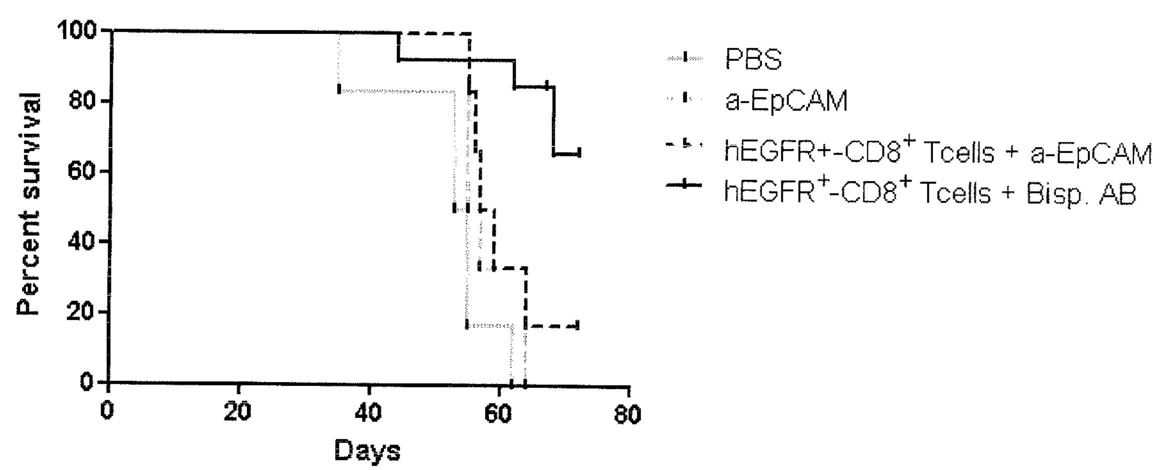

FIG. 12: Treatment of established tumors with the combination of a bispecific antibody with tumor specific transduced T-cells significantly prolongs survival Survival curves of the mouse treatment groups shown in FIG. 11. The termination point of this study was predefined to day 72. The combination treatment significantly prolonged survival of the mice compared to all three control treatments. Differences in survival are significant for group 1 versus 4, 2 versus 4, and 3 versus 4.

Figure 13:
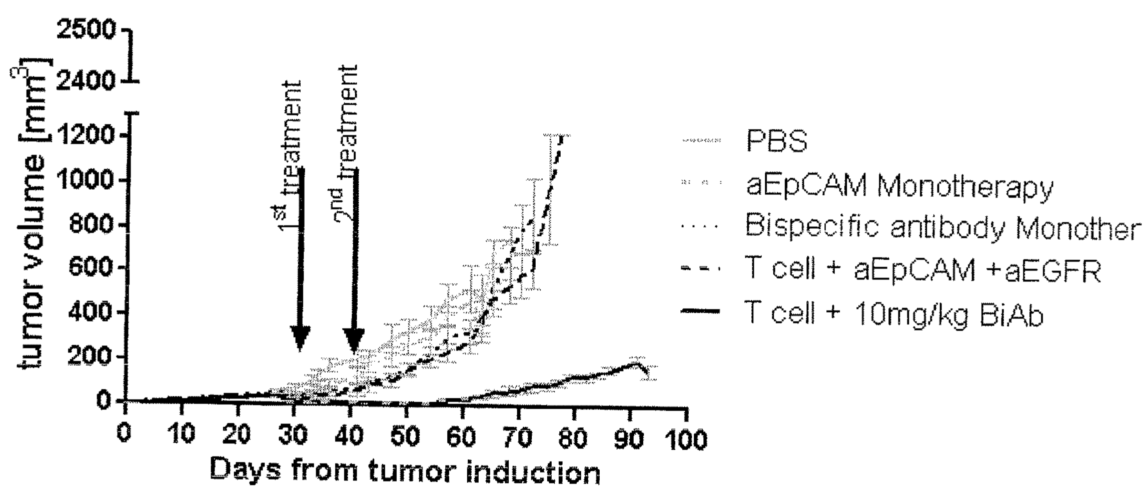

FIG. 13: Treatment of established tumors by the combination of a bispecific antibody and transduced tumor specific T-cells (confirmatory study)

Mice were challenged with a subcutaneous tumor (mGC8) as in the study of FIG. 11. Mice were treated at the indicated time points with either PBS, an anti-EpCAM mono-specific antibody alone (EpCAM G8.8 (SEQ ID NOs: 3 and 4)), the bispecific antibody (MAb225_scFv_G8.8; specific for EpCAM and EGFR (SEQ ID NOs: 5 and 6)), the transduced T-cells (CD8+ T-cells) with anti-EpCAM monospecific antibody (EpCAM G8.8 (SEQ ID NOs: 3 and 4)) plus anti-EGFR mono-specific antibody (MAb 225 (SEQ ID NOs: 1 and 2)) or the transduced T-cells (CD8+ T-cells) with the bispecific antibody (MAb225_scFv_G8.8; specific for EpCAM and EGFR (SEQ ID NOs: 5 and 6)) at two different concentrations. This combination treatment induced a significant reduction and delay in tumor growth when compared to any of the other treatment groups. Differences in tumor volume were significant from day 36 for group 1 versus 5, from day 47 for group 2 versus 5, from day 54 for group 3 versus 5 and from day 63 for group 4 versus 5 (p<0.001 for all comparisons).

FIG. 14: Treatment of established tumors with the combination of a bispecific antibody with tumor specific transduced T-cells significantly prolongs survival (confirmatory study)

Survival curves of the mouse treatment groups shown in FIG. 13. An additional group of three tumor free mice received the combination treatment (as toxicity control, labelled "7-no tumor"). The combination treatment significantly prolonged survival of the mice compared to any of the control treatments. Differences in survival were significant for group 1 versus 5, 2 versus 5, 3 versus 5 and 4 versus 5.

FIG. 15: Murine EpCAM His-Avitag Protein Sequence

Protein sequence of EpCAM ectodomain C-terminally epitope tagged (His-Avi) (corresponding to SEQ ID NO: 10) as encoded by the copy DNA (cDNA) sequence shown in SEQ ID NO: 9.

FIG. 16: Murine EpCAM cDNA Sequence copy DNA (cDNA) sequence of EpCAM ectodomain C-terminally epitope tagged (His-Avi) (SEQ ID NO: 7)

Figure 17:
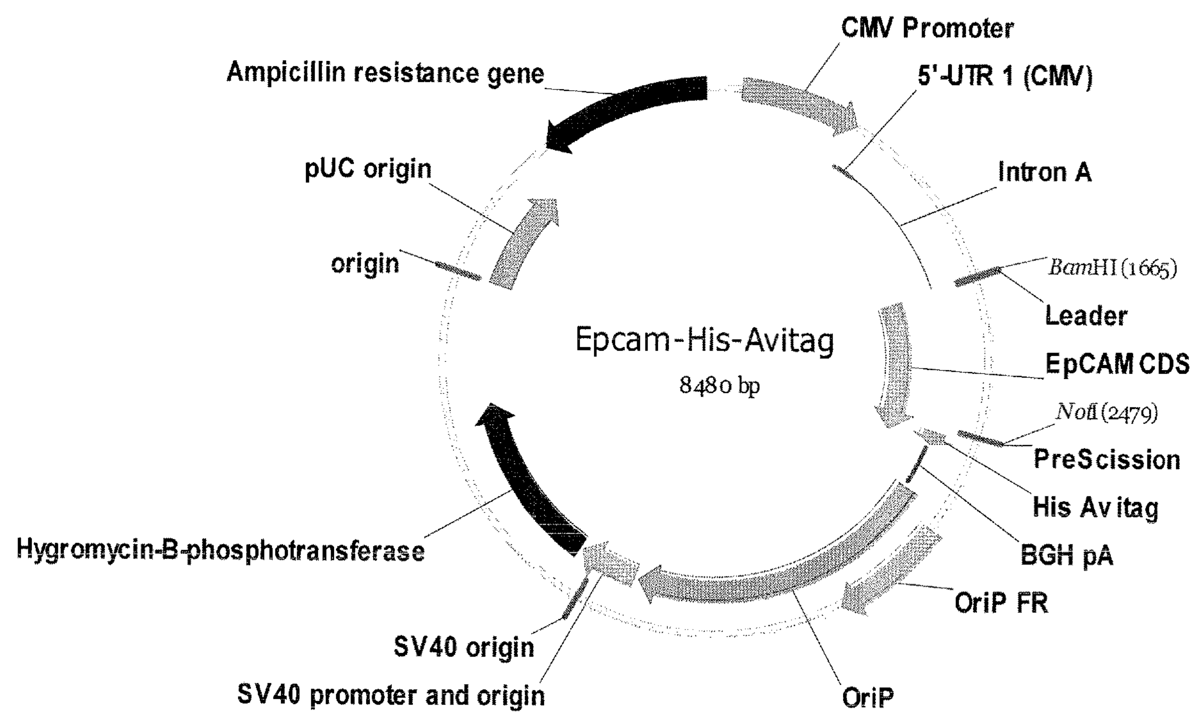

FIG. 17: Vector Map EpCAM ECD

Schematic plasmid map of eukaryotic expression vector containing the EpCAM ectodomain (ECD).

Figure 18:
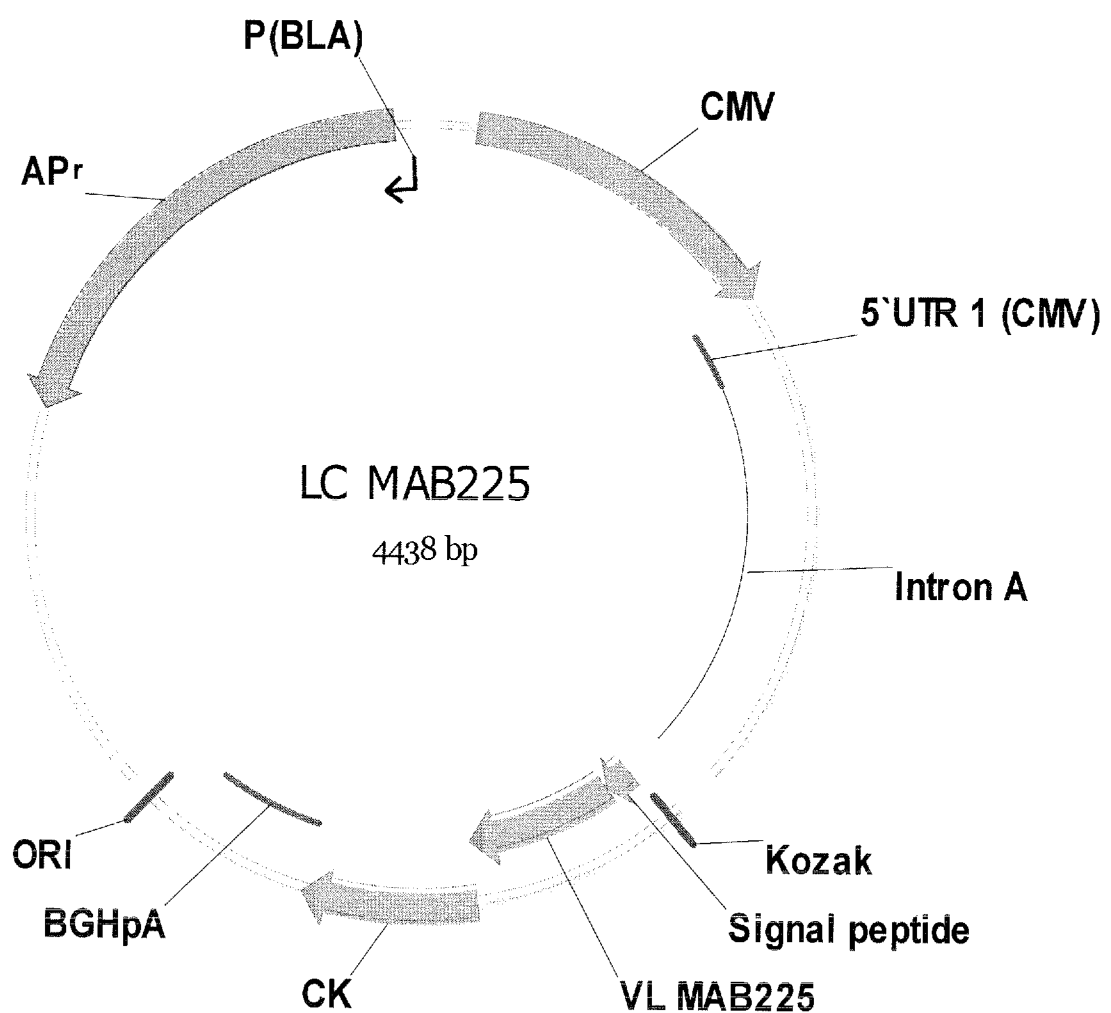

FIG. 18: Vector Map of light chain MAB225

Schematic plasmid map of eukaryotic expression vector containing the light chain of MAB225 (SEQ ID NO: 1).

Figure 19:
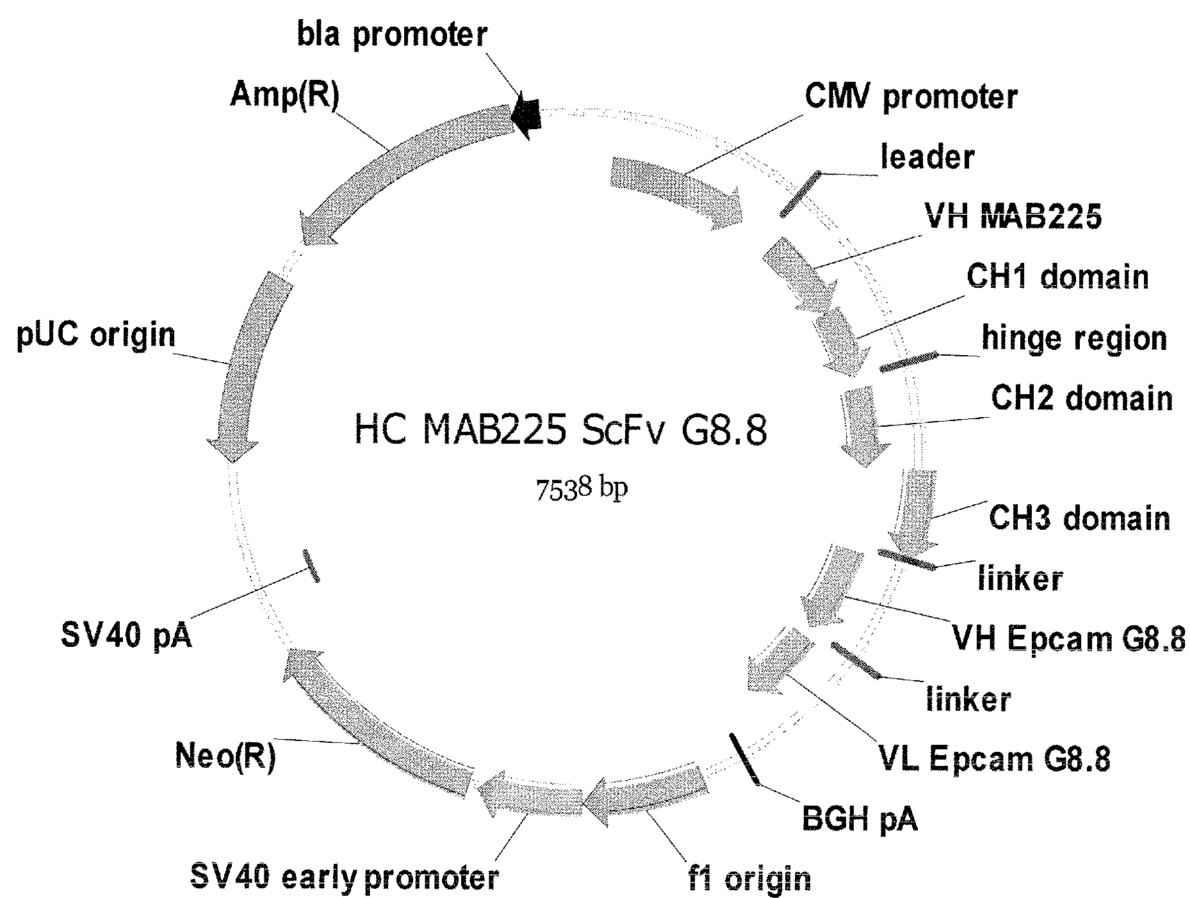

FIG. 19: Vector Map of heavy chain MAB225 with G8.8 scFv fusion

Schematic plasmid map of eukaryotic expression vector containing the heavy chain of MAB225 with a C-terminal G8.8 scFv fusion (SEQ ID NO: 6).

FIG. 20: A representative SEC and SDS-PAGE picture of the bispecific antibody BsAb EpCAM-EGFRvIII, MR1.1

(A) Analytical size exclusion chromatography of a bispecific antibody targeting (human) EGFRvIII and (murine) EpCAM, i.e. BsAb EpCAM-EGFRvIII, MR1.1. (B) Nonreducing (NR) and reducing (R) SDS-PAGE analysis of said bispecific antibody BsAb EpCAM-EGFRvIII, MR1.1. Coomassie blue stained.

FIG. 21: Schematic overview of the new therapeutic principle by recruiting tumor specific T-cells to a tumor through the bispecific antibody BsAb EpCAM-EGFRvIII, MR1.1

Schematic overview of the new therapeutic principle by recruiting tumor specific T-cells to a tumor through a bispecific antibody: T-cells (here transgenic murine OT-I T-cells) carry a T-cell receptor specific for ovalbumin (OVA). These T-cells are additionally transduced with a marker antigen (del-hEGFRvIII; SEQ ID NOs: 17 and 18). The targeted tumor cell (e.g. melanoma B16 cells expressing Ovalbumin (OVA)) naturally expresses the large T antigen which is presented in the context of major histocompatibility complex (MHC) and the tumor antigen (EpCAM). The MHC on the target tumor cell presents in this example the SIINFEKL peptide fragment of OVA. A bispecific antibody (BsAb EpCAM-EGFRvIII, MR1.1) with an antigen binding site for del-hEGFRvIII (SEQ ID NOs: 17 and 18) on one and for (murine) EpCAM on the other arm brings both cell types together. The tumor peptide specific TCR, the tumor peptide and the MHC form an "immunological synapse".

Figure 22:
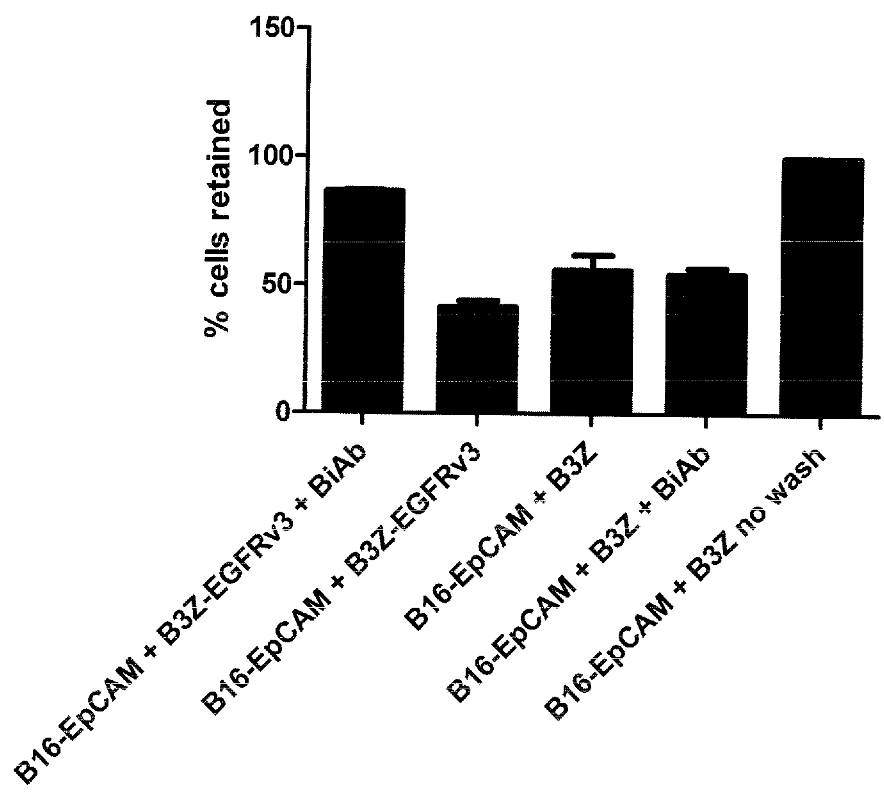

FIG. 22: Cross-linking of transduced T-cells with tumor cells through a bispecific antibody EpCAM expressing B16 melanoma cells (GFP-labelled) were seeded and grown to confluency. Del-hEGFRvIII-transduced B3Z T-cells (permanent cell line) were preloaded with the bispecific antibody (B Ab) (BsAb EpCAM-FG-FRvIII, MR1.1) and subsequently incubated in the plate with the adherent B16 (column no.: 5). After thorough washing (columns nos.: 1 to 4), remaining cells were trypsinized and fluorescent and non-fluorescent cells were measured. The bispecific antibody (BsAb EpCAM-EGFRvIII, MR1.1) retained more transduced cells in the flask (column no.: 1) than any of the controls with washing (column nos.: 2 to 4).

FIG. 23: Amino acid sequences of the bispecific antibody BsAb EpCAM-EGFRvIII, MR1.1

(A) Amino acid sequence of the light chain of the bispecific antibody BsAb EpCAM-EGFRvIII, MR1.1 (without the leader sequence) referring to SEQ ID NO: 15. (B) Amino acid sequence of the heavy chain of the bispecific product BsAb EpCAM-EGFRvIII, MR1.1 (without the leader sequence) referring to SEQ ID NO: 16.

FIG. 24: Sequences of del-hEGFRvIII (A) DNA sequence of del-hEGFRvIII (encoding the protein sequence of FIG. 24(B)) as shown in SEQ ID NO: 17. (B) Protein sequence of del-hEGFRvIII; corresponding to SEQ ID NO: 18.

THE FOLLOWING EXAMPLES ILLUSTRATE THE INVENTION

Illustratively, as proof of the concept, in the following examples, the human anti-EGFR antibody (MAb225; SEQ ID NOs: 1 and 2) was combined with the murine anti-EpCAM (G8.8; SEQ ID NOs: 3 and 4) in order to form a bispecific product (MAb225_scFv_G8.8; SEQ ID NOs: 5 and 6). Furthermore, as illustrated in FIGS. 20 and 21, a bispecific antibody "BsAb EpCAM-EGFRvIII, MR1.1" (SEQ ID NOs: 15 and 16) with an antigen binding site for del-hEGFRvIII (SEQ ID NOs: 17 and 18) on one arm and for (murine) EpCAM on the other arm was constructed; see Example 4.

Example 1

Cloning and Expression of the Bispecific Antibody MAb225_scFv_G8.8 Recombinant DNA Techniques Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

DNA and Protein Sequence Analysis and Sequence Data Management

General information regarding the nucleotide sequences of human immunoglobulins light and heavy chains is given in: Kabat, E. A. et al., (1991) Sequences of Proteins of Immunological Interest, Fifth Ed., NIH Publication No 91-3242. Amino acids of antibody chains are numbered according to EU numbering (Edelman, G. M., et al., PNAS 63 (1969) 78-85; Kabat, E. A., et al., (1991) Sequences of Proteins of Immunological Interest, Fifth Ed., NIH Publication No 91-3242). The GCG's (Genetics Computer Group, Madison, Wis.) software package version 10.2 and Infomax's Vector NTI Advance suite version 11.5 was used for sequence creation, mapping, analysis, annotation and illustration.

DNA Sequencing

DNA sequences were determined by double strand sequencing performed at SequiServe (Vaterstetten, Germany) and Geneart AG (Regensburg, Germany).

Gene Synthesis

Desired gene segments were prepared by Geneart AG (Regensburg, Germany) from synthetic oligonucleotides and PCR products by automated gene synthesis. The gene segments which are flanked by singular restriction endonuclease cleavage sites were cloned into pGA18 (ampR) plasmids. The plasmid DNA was purified from transformed bacteria and concentration determined by UV spectroscopy. The DNA sequence of subcloned gene fragments was confirmed by DNA sequencing. DNA sequences encoding for the light chains were ordered encompassing variable and constant light chain regions with flanking 5' Nan and 3' NheI restriction endonuclease sites. DNA sequences encoding for the variable heavy chain regions plus a fragment of the CH1 region were ordered with flanking 5' KpnI and 3' BamHI restriction sites. DNA sequence encoding the scFv construct was ordered containing a fragment of the CH3 domain with flanking 5' BsrGI and 3' XbaI restriction endonuclease sites. DNA sequence encoding amino acid 1-267 of murine EpCAM (SEQ ID NOs: 7 (cDNA sequence) and 8 (amino acid sequence)) was ordered as gene synthesis with a 5' BamHI and 3' NotI site. All constructs were designed with a 5'-end DNA sequence coding for a leader peptide, which targets proteins for secretion in eukaryotic cells.

1.1 Construction of the Expression Plasmids

An expression vector was used for the construction of all antibody chains. The vector is composed of the following elements (as exemplarily shown in FIG. 18 for the light chain of MAb225 (SEQ ID NO: 1)):

- an origin of replication, oriP, of Epstein-Barr virus (EBV),
- an origin of replication from the vector pUC18 for replication of this plasmid in *E. coli*
- a beta-lactamase gene which confers ampicillin resistance in *E. coli*,
- the immediate early enhancer and promoter from the human cytomegalovirus (HCMV),
- the bovine growth hormone polyadenylation ("poly A") signal sequence, and
- unique KpnI, BamHI, BsrGI and XbaI restriction endonuclease sites (heavy chain vector), or
- unique NarI and NheI restriction endonuclease sites (light chain).

The expression vector coding for production of the heavy chain construct contained the additional following elements (as schematically shown in FIG. 19 for the heavy chain MAb225 with G8.8 scFv fusion (SEQ ID NO: 6)):

- a neomycin resistance cassette (neor),
- the simian virus 40 early promoter, and
- the simian virus 40 polyadenylation ("poly A") signal sequence.

The pG18 (ampR) plasmids carrying the synthesized antibody encoding DNA segments and the expression vector were digested either with KpnI and BamHI in the case of the heavy chain expression vector or with NarI and NheI restriction enzymes in the case of the light chain vector. Similarly, the pG18 plasmid carrying the scFv fragment was cut with BsrGI and XbaI as was the heavy chain vector. All obtained fragments were subjected to agarose gel electrophoresis. Purified DNA segments were then ligated to the isolated expression vector KpnI/BamHI, NarI/NheI, or BsrGI/XbaI fragment resulting in the final expression vectors. The final expression vectors were transformed into *E. coli* cells, expression plasmid DNA was isolated (Miniprep) and subjected to restriction enzyme analysis and DNA sequencing. Correct clones were grown in 150 ml LB-Amp medium, again plasmid DNA was isolated (Maxiprep) and used for subsequent experiments.

An expression vector was used for the construction of the recombinant murine EpCAM ectodomain (referring to the amino acid sequence of SEQ ID NO: 10 (as encoded by the cDNA sequence shown in SEQ ID NO: 9), whereas the origin sequence was derived from PubMed entry NM_008532 (NM 008532.2, GI:112293274). The vector (see FIG. 17) is composed of the following elements:

- an origin of replication, oriP, of Epstein-Barr virus (EBV),
- an origin of replication from the vector pUC18 for replication of this plasmid in *E. coli*
- a beta-lactamase gene which confers ampicillin resistance in *E. coli,*
- a hygromycin-b-phosphotransferase cassette,
- the simian virus 40 early promoter,
- the simian virus 40 polyadenylation ("poly A") signal sequence,
- the immediate early enhancer and promoter from the human cytomegalovirus (HCMV),
- a PreScission Plus site followed by a His Avitag for N-terminal fusion of cDNAs of interest,
- the bovine growth hormone polyadenylation ("poly A") signal sequence, and
- unique BamHI and NotI restriction endonuclease sites.

The pG18 (ampR) plasmids carrying the synthesized EpCAM ectodomain encoding DNA segment and the expression vector (see FIG. 17) were digested with BamHI and NotI. All obtained fragments were subjected to agarose gel electrophoresis. Purified DNA segments were then ligated to the isolated Roche expression vector BamHI/NotI fragment resulting in the final expression vector. The final expression vector was transformed into *E. coli* cells, expression plasmid DNA was isolated (Miniprep) and subjected to restriction enzyme analysis and DNA sequencing. Correct clones were grown in 150 ml LB-Amp medium, again plasmid DNA was isolated (Maxiprep) and used for subsequent experiments.

Example 2

Expression and Purification of the EpCAM Ectodomain Showing High Binding Affinity 2.1 Transient expression of immunoglobulin variants in human embryonic kidney 293 (HEK293) cells Recombinant immunoglobulin variants (MAB225, MAB225_scFv_G8.8 and G8.8) were expressed by transient transfection of human embryonic kidney 293-F cells using the FreeStyle™ 293 Expression System according to the manufacturer's instruction (Invitrogen, USA). Briefly, suspension FreeStyle™ 293-F cells were cultivated in FreeStyle™ 293 expression medium at 37° C./8% $CO_2$. Cells were seeded in fresh medium at a density of $1\times10^6$ viable cells/ml the day before transfection. DNA-293fectin™ complexes were prepared in Opti-MEM® I medium (Invitrogen, USA) using 665 μl of 293-Free™ Transfection Reagent (Novagen, EMD, USA) and 500 μg of total DNA (including the light chain plasmid DNA and the heavy chain plasmid DNA in a 1:1 molar ratio) for 500 ml final transfection volume. Antibody containing cell culture supernatants were harvested 6 days after transfection by centrifugation at 3500 rpm for 15 minutes at room temperature (RT) and filtered through a sterile filter (0.22 μm) Supernatants were stored at −80° C. until purification. The procedure for the production of the murine EpCAM ectodomain was similar to the production of the immunoglobulin variants and 500 μg of DNA were used for a 500 ml final transfection volume.

2.2 Purification of Antibodies

Antibodies were purified from cell culture supernatants by affinity chromatography using Protein A-Sepharosc™ (GE Healthcare, Sweden) and Superdex200 size exclusion chromatography. Briefly, sterile filtered cell culture supernatants were applied on a 5 ml MabSelect Xtra (GE Healthcare) column equilibrated with PBS buffer (10 mM $Na_2HPO_4$, 1 mM $KH_2PO_4$, 137 mM NaCl and 2.7 mM KCl, pH 7.4). Unbound proteins were washed out with equilibration buffer. Antibody and antibody variants were eluted with 0.1 M citrate buffer, pH 3.0, and the protein containing fractions were neutralized with 0.2 M Tris, pH 9.0. Then, the eluted protein fractions were pooled, concentrated with an Amicon Ultra centrifugal filter device (MWCO: 30 K, Millipore) to a volume of 3 ml and loaded on a Superdex200 HiLoad 120 ml 16/60 or 26/60 gel filtration column (GE Healthcare, Sweden) equilibrated with 20 mM Histidin, 140 mM NaCl, pH 6.0. Fractions containing purified antibodies with less than 5% high molecular weight aggregates were pooled and stored as approximately 1.0 mg/ml aliquots at −80° C.

Murine EpCAM ectodomain (SEQ ID NO: 9) was purified from cell culture supernatants by affinity chromatography using Ni-chelate chromatography. Briefly, sterile filtered cell culture supernatants were applied on a HisTrap FF (GE Healthcare, Sweden) column equilibrated in 20 mM "$NaPO_4$", 0.5 M NaCl, 20 mM Imidazole, pH 7.40. Unbound proteins were washed out with equilibration buffer. The EpCAM ectodomain (SEQ ID NO: 9) was eluted with a buffer containing 20 mM "$NaPO_4$", 0.5 M NaCl, 500 mM Imidazole, pH 7.40. Peak fractions were pooled and dialysed over night against a buffer containing 20 mM Histidine, 140 mM NaCl, pH 6.70. The protein was stored as 17.5 mg/ml aliquots at −80° C.

2.3 Analysis of Purified Proteins

The protein concentration of purified protein samples was determined by measuring the optical density (OD) at 280 nm, using the molar extinction coefficient calculated on the basis of the amino acid sequence. Purity and molecular weight of antibodies were analyzed by SDS-PAGE in the presence and absence of a reducing agent (5 mM 1,4-dithiotreitol) and staining with Coomassie brilliant blue. The NuPAGE® Pre-Cast gel system (Invitrogen, USA) was used according to the manufacturer's instruction (4-12% Bis-Tris-gels). The aggregate content of antibody samples was analyzed by high-performance SEC using a TSKgel G3000SW column (TOSOH Bioscience, USA) in 50 mM "$KPO_4$", pH 7.5, 300 mM NaCl running buffer at 25° C. 25 μg protein were injected on the column at a flow rate of 0.8 ml/min and eluted isocratic over 20 minutes. The integrity of the amino acid backbone of reduced immunoglobulin variant chains was verified by NanoElectrospray Q-TOF mass spectrometry after removal of N-glycans by enzymatic treatment with Peptide-N-Glycosidase F (Roche Molecular Biochemicals).

2.4 Immunoprecipitation of Murine Recombinant EpCAM

An IP was performed to check if the antibodies G8.8 (SEQ ID NOs: 3 and 4) and the bispecific MAB225_G8.8 antibody (SEQ ID NOs: 5 and 6) bind to murine EpCAM recombinant ectodomain (ECD) (SEQ ID NO: 10). About 15 μg EpCAM ECD and 10 μg antibody were diluted to 1.5 mL total volume with TBS Tween 0.1% and incubated 10 min at room temperature. Antibody without EpCAM was prepared in parallel as negative control to distinguish heavy and light chain bands. 50 μL, of a 50% protein A slurry were added and samples were incubated for 40 mM under agitation at room temperature, washed with TBS-T, eluted with citrate buffer at pH 3.0 and loaded on a 4-12% Bis-Tris-gel. 4 μg of recombinant EpCAM ECD was loaded as control. The gel was stained with coomassie brilliant blue.

2.5 Mass Spectrometry

The total deglycosylated mass of antibodies was determined and confirmed via electrospray ionization mass spectrometry (ESI-MS). Briefly, 100 μg purified antibodies were deglycosylated with 50 mU N-Glycosidase F (PNGaseF, ProZyme) in 100 mM $KH_2PO_4/K_2HPO_4$, pH 7 at 37° C. for 12-24 h at a protein concentration of up to 2 mg/ml and subsequently desalted via HPLC on a Sephadex G25 column (GE Healthcare). The mass of the respective antibody chains was determined by ESI-MS after deglycosylation and reduction. In brief, 50 μg antibody in 115 μl were incubated with 60 μl 1M TCEP and 50 μl 8 M Guanidine-hydrochloride subsequently desalted. The total mass and the mass of the reduced antibody chains were determined via ESI-MS on a Q-Star Elite MS system equipped with a NanoMate source. The mass range recorded depends on the samples molecular weight. In general for reduced antibodies the mass range was set from 600-2000 m/z and for non-reduced antibodies from 1000-3600 m/z.

2.6 Surface Plasmon Resonance

The binding properties of the EGFR-specific MAb225 (SEQ ID NOs: 1 and 2) and the EpCAM-specific G8.8 antibody (SEQ ID NOs: 3 and 4) as well as of the bispecific MAb225_scFv_G8.8 antibody was analyzed by surface plasmon resonance (SPR) technology using a Biacore instrument (Biacore, GE-Healthcare, Uppsala). This system is well established for the study of molecule interactions. It allows a continuous real-time monitoring of ligand/analyte bindings and thus the determination of association rate constants (ka), dissociation rate constants (kd), and equilibrium constants (KD) in various assay settings. SPR-technology is based on the measurement of the refractive index close to the surface of a gold coated biosensor chip. Changes in the refractive index indicate mass changes on the surface caused by the interaction of immobilized ligand with analyte injected in solution. If molecules bind to immobilized ligand on the surface the mass increases, in case of dissociation the mass decreases. For capturing, a goat anti-mouse IgG antibody was immobilized on the surface of a CM5 biosensorchip using amine-coupling chemistry according to the manufacturer's instructions. Flow cells were activated with a 1:1 mixture of 0.1 M N-hydroxysuccinimide and 0.4 M 1-ethyl-3-(3-dimethylaminopropyl)-carbodiimide hydrochloride at a flow rate of 5 μl/min at 25° C. Anti-mouse IgG antibody was injected in 10 mM sodium acetate, pH 4.5 at 10 μg/mL. A reference control flow cell was treated in the same way but with vehicle buffers only instead of the capturing antibody. Surfaces were blocked with an injection of 1 M ethanolamine/HCl pH 8.5. The antibodies under evaluation were diluted (30 nM MAb225_scFv_G8.8, 5 nM MAb225, 8 nM G8.8) in PBS-T+0.1% BSA (dilution buffer) and captured as ligand in separate cycles by injection with 5 μl/min for 60 sec. All interactions were performed at 37° C., using PBS-T as running buffer. The analytes were injected in a series of threefold increasing concentrations (EGFR ECD 4.12-1000 nM and EpCAM ECD 0.91-2000 nM in PBS-T+0.1% BSA) with a flow rate of 50 μl/min, 180 sec association, 1200 sec dissociation. The capture antibody was regenerated after each cycle with 10 mM glycine, pH 2.0 at a flow rate of 30 μl/min for 60 sec. Signals were detected at a rate of one signal per second.

A summary of the biochemical characterization of the illustrative bispecific antibody MAb225_scFv_G8.8 as well as the individual parental antibodies MAb225 and G8.8 is given in Table 1 showing that all antibodies bound with high affinity to their respective target

| ligand | analyte | $k_a$ [$M^{-1}s^{-1}$] | $k_d$ [$s^{-1}$] | t(½) [min] | $K_D$ [M] |
|---|---|---|---|---|---|
| MAB225_scFv_G8.8 | mu EpCAM | 2.0E+05 | 2.5E−03 | 4.6 | 1.2E−08 |
| G8.8 | mu EpCAM | 2.2E+05 | 1.3E−02 | 0.9 | 6.1E−08 |
| MAB225_scFv_G8.8 | hu Her1 | 1.1E+06 | 5.7E−03 | 2.0 | 5.5E−09 |
| MAB225 | hu Her1 | 1.3E+06 | 5.7E−03 | 2.0 | 4.3E−09 |

Example 3

Transduction of CD8+ T-Cells and Cytotoxic Killing Assay 3.1 Cell Culture

Spleen was harvested from mice described below under item 3.2. Single cell suspension was obtained through mashing the spleen through a 40 μM cell strainer (BD Falcon, Germany). Strainer was washed 3 times with plain T-cell medium and cell pellet was freed from erythrocytes by erilysis solution (BD Pharmingen, Germany) for 90 seconds. Primary murine T-cells were maintained in T-cell medium composed of RPMI, 1% L-Glutamin, 1% Penicillin and Streptomycin, 1% Natrium Pyruvat, 1 mM HEPES (all PAA, Germany) and 10% FBS (Gibco, USA). T-cell line B3Z (Leisegang et al., J Mol Med (2008), 86(5), 573-583) was maintained in the same medium. Plat E packaging cell line (Cell Biolabs, Inc, USA (cellbiolabs.com)) was maintained in DMEM, 1% L-Glutamin, 1% Penicillin-Streptomycin (all PAA, Germany), 10 μg/ml Puromycin and 1 μg/ml Blasticidin (Sigma, Germany). The murine gastric cancer cell line was kindly provided by W. Zimmermann, Munich and cultured in DMEM, 1% L-Glutamin, 1% Penicillin and Streptomycin, 1% Natrium Pyruvat, 1% Non-Essential-Amino-Acids and 10% FBS. Murine mammary carcinoma cell line 4T1 (ATCC NO: ° CRL-2539) was passaged in RPMI, 1% L-Glutamin, 1% Penicillin and Streptomycin, 1% Natrium Pyruvat, 1% Non-Essential-Amino-Acids and 10% FBS. Murine melanoma cell line B16 (ATCC NO° CRL-6322) was maintained in DMEM, 1% L-Glutamin, 1% Penicillin and Steptomycin and 10% FBS.

3.2 Mice

Wild type C57Bl/6 mice were bought from Harlan laboratories (The Netherlands). Mice transgenic for a T-cell receptor specific for the immunodominant epitope I of the large T-antigen were bought from the Jackson Laboratory, USA (B6.Cg-Tg(TcraY1, TcrbY1)416Tev/J), USA). Mouse transgenic for a T-cell receptor specific for OVA (Ovalbumin) were bought from the Jackson Laboratory, USA (C57Bl/6-Tg(TcraTcrb)1100Mjb/j)

3.3 T-Cell: Transduction Vector and Cloning

The vector for T-cell transduction was pMP71 (Schambach et al., *Mol Ther* (2000), 2(5), 435-45). Truncated human Epidermal-Growth-Factor-Receptor (del EGFR, as a prototype example of an immunologically inert protein inserted into the membrane, see SEQ ID NO 11 as the cDNA sequence and SEQ ID Nn: 12 as the (encoded) amino acid sequence) flanked by the restriction sites NotI and EcoRI was created by gene synthesis. Using these two recombination sites, del EGFR was cloned into pMP71 by ligation (T4-ligase, Thermo scientific, Germany). Del EGFR-pMP71 was amplified in *E. coli* (DH5a) and sequence was verified by sequencing using the following primer sequences: forward primer: CAGCATCGTTCTGTGTTGTCT (SEQ ID NO: 13), reverse primer: CATTTAAATGTATACCCAAATCAA (SEQ ID NO: 14). DNA was extracted using the Qiagen plasmid maxi kit (Qiagen, Germany). All steps were performed according to the manufacturer's instructions.

3.4 Primary T-Cell and T-Cell Line Transduction

Transduction was performed according to the method described by Leisegang et al. (*J Mol Med*, (2008) 86, 573-83) with minor modifications. In brief, packaging cell line Plat E (as described by Morita et al., *Gene Ther* (2000). 7, 1063-6) was seeded in 6-well plates and grown over night to 70-80% confluence. On day one, 16 μg of DNA were mixed together with 100 mM CaCl2 (Merck, Germany) and 126.7 μM Chloroquin (Sigma, USA). Plat-E cells were starved for 30 min in low serum medium (3%) and then incubated for 6 h with the precipitated DNA. Medium was then removed and exchanged with culture medium. On day two, primary splenocytes were harvested from C57Bl/6 mice (Harlan Laboratories, The Netherlands). Single cell suspensions of splenocytes were stimulated with anti-CD3 (clone 145-2c11 BD Pharmingen, USA), anti-CD28 (clone 37.51, BD Pharmingen, USA) and recombinant murine IL-2 (Peprotech, Germany) in T-cell medium over night. On day 3, 24-well plates were coated with 12.5 μg/ml recombinant retronectin (Takara Biotech, Japan) for 2 h at room temperature, blocked with 2% Bovine Serum Albumin (Roth, Germany) for 30 min at 37° C. and washed with PBS. Supernatant of Plat E was harvested and passed through a filter (40 μm, Milipore, USA). Fresh T-cell medium was then added to Plat E cells. 1 ml of filtered supernatant was distributed in each well and spinoculated for 2 h at 4° C. Supernatant was then removed from the 24-well plate. $10^6$ T-cells were seeded in one ml T-cell medium supplemented with 10U IL-2 and 400000 anti-CD3 and anti-CD28 beads (Invitrogen, Germany) per well and spinoculated at 800 g for 30 min at 32° C. On day four, Plat E supernatant was again harvested and filtered. 1 ml was added to each well of the 24-well plate and spinoculated at 800 g for 90 min at 32° C. Cells were subsequently incubated for 6 additional hours at 37° C. 1 ml supernatant was replaced by T-cell medium with IL-2. On day five, cells were harvested, counted and reseeded at $10^6$ cells/ml density in T-cell medium supplemented with 10 ng IL-15 per ml (Peprotech, Germany). T-cells were kept at this density until day 10 when cell analysis or functional assays were performed.

3.5 Antibody Crosslinking Assay

EpCAM expressing 4T1 were seeded on 6-well plates and grown to confluence. Del EGFR transduced T-cells were labeled with calcein (Invitrogen, Germany) according to the manufacturer's instructions and preloaded for 30 min at 37° C. with 20 μg/ml EpCAM×EGFR bispecific antibody (MAb225_scFv_G8.8). Cells were added to the 4T1 culture for 2 h at 37° C. The supernatant was removed completely and the plate washed thoroughly with PBS. Cells were then visualized by fluorescence microscopy or lysed and calcein retention was measured with a multilabel reader (Berthold, Germany).

3.6 Killing Assay mGC8 cells (Nöckel et al., *BMC* (2006), 14, 6:57) or B16 cells were labeled with calcein according to the manufacturer's instructions. Del EGFR transduced T-cells (from wild type, OT-1 or TCR-I mice (were preloaded with 20 $\mu g \cdot ml^{-1}$ antibody (bispecific or control antibody) for 30 min at 37° C. T-cells were then incubated at different target to effector cell ratios over night at 37° C. with target cells. Total lysis of target cells was induced by addition of 6% Triton X (Firma). Lysis in % was calculated according to the following formula:

$$(MFI^{of\ interest}-MFI^{background})/(MFI^{total\ lysis}-MFI^{background})*100$$

3.7 In Vivo Therapy

Wild type C57Bl/6 mice were inoculated subcutaneously with $5 \cdot 10^6$ mGC8 cells. When tumors became palpable (by day 15), T-cell transduction was started and 10 days later therapy was given either intraperitoneally (for antibodies at a dose of 10 mg/kg) or intravenously (for T-cells or preloaded T-cells at a dose of $5 \cdot 10^6$ cells per mice). One week later treatment was repeated. Mice were monitored every 2-3 days by measuring the subcutaneous tumor. Mice were killed according to regulations either at a predefined time point or according to the criteria published by GV SOLAS (Morton, *Vet Rec* (1985) 116, 431-436).

3.8. Statistical Analysis

For comparison between groups, unpaired T tests were applied. Tumor volumes were compared by two-way ANOVA and survival differences were assessed using the log-rank test. All the statistical analysis were performed using GraphPad Prism software (GraphPad software inc.). Results were considered significant when $p<0.05$.

Example 4

Cloning and Expression of the Bispecific Antibody BsAb EpCAM-EGFRvIII, MR1.1

Analogously to example 1 and 2 the (A) Analytical size exclusion chromatography of a bispecific antibody BsAb EpCAM-EGFRvIII, MR1.1 targeting (human) EGFRvIII and (murine) EpCAM was prepared, purified and characterized (see FIG. 20 (A) Analytical size exclusion chromatography (B) Non-reducing (NR) and reducing (R) SDS-PAGE analysis of said bispecific antibody. Coomassie blue stained).

Example 5

Cross-Linking of Transduced T-Cells with B16 Melanoma Cells Through a Bispecific Antibody BsAb EpCAM-EGFRvIII, MR1.1 (See Scheme in FIG. 21)

EpCAM expressing B16 melanoma cells (GFP-labelled) (B16-OVA-mEpCAM cells) (were seeded in a 12-well-plate and grown to confluency over night. The following day del-hEGFRvIII transduced (del-hEGFRvIII inserted; see SEQ ID NO: 17 as the DNA sequence and SEQ ID NO: 18 as the (encoded) amino acid sequence) B3Z T-cells (permanent cell line) were preincubated with the bispecific antibody BsAb EpCAM-EGFRvIII, MR1.1 (20 μg) for 1 hour at 37° C. The remaining unbound bispecific antibody was subsequently washed off. Bispecific antibody (BiAb) pre-loaded B3Z T cells were incubated with adherent B16 tumor cells at 37° C. (column no.: 5). After thorough washing four times with PBS (columns nos.: 1 to 4), remaining cells were trypsinized and fluorescent and non-fluorescent cells were measured by flow cytometry. As controls B16 melanoma cells were treated with delEGFRvIII transduced B3Z T-cells only (without antibody BsAb EpCAM-EGFRvIII; see column no.: 2), with untransduced B3Z T-cells only (without antibody BsAb EpCAM-EGFRvIII see column no.: 3) with and without washing and with untransduced B3Z T-cells with bispecific antibody BsAb EpCAM-EGFRvIII (column no: 4). The bispecific antibody (BiAb) BsAb EpCAM-EGFRvIII retained more transduced cells in the flask (column no.: 1) than any of the controls with washing (column nos.: 2 to 4). Results are shown in FIG. 22

The invention claimed is:

1. A kit comprising (A) bispecific antibody which comprises (i) a first binding domain comprising a variable heavy chain (VH) and a variable light chain (VL) which binds an antigen on CD8+ T-cells that does not naturally occur in or on CD8+ T-cells, wherein the antigen is EGFR; and (ii) a second binding domain comprising a VH and a VL which binds a tumor-specific antigen naturally occurring on the surface of a tumor cell, wherein the antigen is EpCAM;

(B) a nucleic acid encoding EGFR for transducing CD8+ T-cells obtained from a subject to be treated for a cancer, wherein cells of the cancer express EpCAM on their surface; and (C) instructions for use; wherein the bispecific antibody is to be administered before, simultaneously with, or after administration of the transduced CD8+ T-cells comprising the antigen that does not naturally occur in or on CD8+ T-cells; wherein the CD8+ T-cells were obtained from a subject to be treated for a cancer; wherein cells of the cancer express EpCAM on their surface.

2. The kit of claim 1, wherein said bispecific antibody is selected from the group consisting of a full antibody, a F(ab)-, Fab'-SH-, Fv-, Fab'-, F(ab')2-fragment, a chimeric antibody, a CDR-grafted antibody, a fully human antibody, a bivalent antibody-construct, an antibody-fusion protein, a synthetic antibody, a bivalent antibody, a trivalent antibody, a tetravalent antibody, bivalent single chain antibody, a trivalent single chain antibody and a multivalent single chain antibody.

3. The kit of claim 1, wherein said first domain and/or second binding domain is human and/or humanized.

4. The kit of claim 1, wherein the transduced CD8+ T-cells further comprises a T-cell receptor that naturally occurs on said T-cells and/or a T-cell receptor that has been genetically introduced into said T-cell.

5. The kit of claim 1, wherein the bispecific antibody is encoded by a nucleic acid sequence.

6. A bispecific antibody which comprises (i) a first binding domain comprising a VH and a VL which binds an antigen on CD8+ T-cells that does not naturally occur in or on CD8+ T-cells, wherein the antigen is EGFR; and (ii) a second binding domain comprising a VH and a VL which binds a tumor-specific antigen naturally occurring on the surface of a tumor cell, wherein the antigen is EpCAM, wherein said bispecific antibody is to be administered before, simultaneously with or after administration of transduced CD8+ T-cells comprising said antigen which does not naturally occur in or on CD8+ T-cells and wherein said CD8+ T-cells were obtained from a subject to be treated for a cancer, wherein cells of the cancer express EpCAM on their surface.

7. The bispecific antibody of claim 6, wherein said cancer is of epithelial, endothelial or mesothelial origin, or is a cancer of the blood.

8. The bispecific antibody of claim 6, wherein said bispecific antibody is selected from the group consisting of a full antibody, a F(ab)-, Fab'-SH-, Fv-, Fab'-, F(ab')2-fragment, a chimeric antibody, a CDR-grafted antibody, a fully human antibody, a bivalent antibody-construct, an antibody-fusion protein, a synthetic antibody, a bivalent antibody, a trivalent antibody, a tetravalent antibody, bivalent single chain antibody, a trivalent single chain antibody and a multivalent single chain antibody.

9. The bispecific antibody of claim 6, wherein said first domain and/or second binding domain is human and/or humanized.

10. The bispecific antibody of claim 6, wherein the transduced CD8+ T-cells further comprises a T-cell receptor that naturally occurs on said T-cells and/or a T-cell receptor that has been genetically introduced into said T-cell.

11. The bispecific antibody of claim 6, wherein the bispecific antibody is encoded by a nucleic acid sequence.

12. A pharmaceutical composition comprising a bispecific antibody which comprises (i) a first binding domain comprising a VH and a VL which binds an antigen on CD8+ T-cells that does not naturally occur in or on CD8+ T-cells, wherein the antigen is EGFR; and (ii) a second binding domain comprising a VH and a VL which binds a tumor-specific antigen naturally occurring on the surface of a tumor cell, wherein the antigen is EpCAM, which composition is to be administered in combination with transduced CD8+ T-cells comprising said antigen which does not naturally occur in or on CD8+ T-cells, wherein said composition is to be administered before, simultaneously with or after administration of the transduced CD8+ T-cells and wherein said CD8+ T-cells were obtained from a subject to be treated for a cancer, wherein cells of the cancer express EpCAM on their surface.

13. The pharmaceutical composition of claim 12, wherein said bispecific antibody is selected from the group consisting of a full antibody, a F(ab)-, Fab'-SH-, Fv-, Fab'-, F(ab')2-fragment, a chimeric antibody, a CDR-grafted antibody, a fully human antibody, a bivalent antibody-construct, an antibody-fusion protein, a synthetic antibody, a bivalent antibody, a trivalent antibody, a tetravalent antibody, bivalent single chain antibody, a trivalent single chain antibody and a multivalent single chain antibody.

14. The pharmaceutical composition of claim 12, wherein said first domain and/or second binding domain is human and/or humanized.

15. The pharmaceutical composition of claim 12, wherein the transduced CD8+ T-cells further comprises a T-cell receptor that naturally occurs on said T-cells and/or a T-cell receptor that has been genetically introduced into said T-cell.

16. The pharmaceutical composition of claim 12, wherein the bispecific antibody is encoded by a nucleic acid sequence.

* * * * *

SEQUENCE LISTING

```
<160> NUMBER OF SEQ ID NOS: 18

<210> SEQ ID NO 1
<211> LENGTH: 234
<212> TYPE: PRT
<213> ORGANISM: Homo sapiens
<220> FEATURE:
<221> NAME/KEY: SOURCE
<222> LOCATION: 1..234
<223> OTHER INFORMATION: /mol_type=“protein”
      /note=“MAb 225 (human EGFR-specific antibody) light chain”
      /organism=“Homo sapiens”

<400> SEQUENCE: 1

Met Arg Cys Leu Ala Glu Phe Leu Gly Leu Leu Val Leu Trp Ile Pro
1               5                   10                  15

Gly Ala Ile Gly Asp Ile Leu Leu Thr Gln Ser Pro Val Ile Leu Ser
            20                  25                  30

Val Ser Pro Gly Glu Arg Val Ser Phe Ser Cys Arg Ala Ser Gln Ser
        35                  40                  45

Ile Gly Thr Asn Ile His Trp Tyr Gln Gln Arg Thr Asn Gly Ser Pro
    50                  55                  60

Arg Leu Leu Ile Lys Tyr Ala Ser Glu Ser Ile Ser Gly Ile Pro Ser
65                  70                  75                  80

Arg Phe Ser Gly Ser Gly Ser Gly Thr Asp Phe Thr Leu Ser Ile Asn
                85                  90                  95

Ser Val Glu Ser Glu Asp Ile Ala Asp Tyr Tyr Cys Gln Gln Asn Asn
            100                 105                 110

Asn Trp Pro Thr Thr Phe Gly Ala Gly Thr Lys Leu Glu Leu Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230


<210> SEQ ID NO 2
<211> LENGTH: 468
<212> TYPE: PRT
<213> ORGANISM: Homo sapiens
<220> FEATURE:
<221> NAME/KEY: SOURCE
```

```
<222> LOCATION: 1..468
<223> OTHER INFORMATION: /mol_type="protein"
      /note="MAb 225 (human EGFR-specific antibody)  heavy chain"
      /organism="Homo sapiens"

<400> SEQUENCE: 2

Met Ala Val Leu Ala Leu Leu Phe Cys Leu Val Thr Phe Pro Ser Cys
1               5                   10                  15

Val Leu Ser Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
        35                  40                  45

Thr Asn Tyr Gly Val His Trp Val Arg Gln Ser Pro Gly Lys Gly Leu
    50                  55                  60

Glu Trp Leu Gly Val Ile Trp Ser Gly Gly Asn Thr Asp Tyr Asn Thr
65                  70                  75                  80

Pro Phe Thr Ser Arg Leu Ser Ile Asn Lys Asp Asn Ser Lys Ser Gln
                85                  90                  95

Val Phe Phe Lys Met Asn Ser Leu Gln Ser Asn Asp Thr Ala Ile Tyr
            100                 105                 110

Tyr Cys Ala Arg Ala Leu Thr Tyr Tyr Asp Tyr Glu Phe Ala Tyr Trp
        115                 120                 125

Gly Gln Gly Thr Leu Val Thr Val Ser Ala Ala Lys Thr Thr Ala Pro
    130                 135                 140

Ser Val Tyr Pro Leu Ala Pro Val Cys Gly Asp Thr Thr Gly Ser Ser
145                 150                 155                 160

Val Thr Leu Gly Cys Leu Val Lys Gly Tyr Phe Pro Glu Pro Val Thr
                165                 170                 175

Leu Thr Trp Asn Ser Gly Ser Leu Ser Ser Gly Val His Thr Phe Pro
            180                 185                 190

Ala Val Leu Gln Ser Asp Leu Tyr Thr Leu Ser Ser Ser Val Thr Val
        195                 200                 205

Thr Ser Ser Thr Trp Pro Ser Gln Ser Ile Thr Cys Asn Val Ala His
    210                 215                 220

Pro Ala Ser Ser Thr Lys Val Asp Lys Lys Ile Glu Pro Arg Gly Pro
225                 230                 235                 240

Thr Ile Lys Pro Cys Pro Pro Cys Lys Cys Pro Ala Pro Asn Leu Leu
                245                 250                 255

Gly Gly Pro Ser Val Phe Ile Phe Pro Pro Lys Ile Lys Asp Val Leu
            260                 265                 270

Met Ile Ser Leu Ser Pro Ile Val Thr Cys Val Val Val Asp Val Ser
        275                 280                 285

Glu Asp Asp Pro Asp Val Gln Ile Ser Trp Phe Val Asn Asn Val Glu
    290                 295                 300

Val His Thr Ala Gln Thr Gln Thr His Arg Glu Asp Tyr Asn Ser Thr
305                 310                 315                 320

Leu Arg Val Val Ser Ala Leu Pro Ile Gln His Gln Asp Trp Met Ser
                325                 330                 335

Gly Lys Glu Phe Lys Cys Lys Val Asn Asn Lys Asp Leu Pro Ala Pro
            340                 345                 350

Ile Glu Arg Thr Ile Ser Lys Pro Lys Gly Ser Val Arg Ala Pro Gln
        355                 360                 365

Val Tyr Val Leu Pro Pro Pro Glu Glu Glu Met Thr Lys Lys Gln Val
    370                 375                 380
```

```
Thr Leu Thr Cys Met Val Thr Asp Phe Met Pro Glu Asp Ile Tyr Val
385                 390                 395                 400

Glu Trp Thr Asn Asn Gly Lys Thr Glu Leu Asn Tyr Lys Asn Thr Glu
                405                 410                 415

Pro Val Leu Asp Ser Asp Gly Ser Tyr Phe Met Tyr Ser Lys Leu Arg
            420                 425                 430

Val Glu Lys Lys Asn Trp Val Glu Arg Asn Ser Tyr Ser Cys Ser Val
        435                 440                 445

Val His Glu Gly Leu His Asn His His Thr Thr Lys Ser Phe Ser Arg
    450                 455                 460

Thr Pro Gly Lys
465
```

<210> SEQ ID NO 3
<211> LENGTH: 234
<212> TYPE: PRT
<213> ORGANISM: Mus musculus
<220> FEATURE:
<221> NAME/KEY: SOURCE
<222> LOCATION: 1..234
<223> OTHER INFORMATION: /mol_type="protein"
/note="MAb EpCAM (mouse EpCAM-specific antibody, G8.8), light chain" /organism="Mus musculus"

<400> SEQUENCE: 3

```
Met Arg Cys Leu Ala Glu Phe Leu Gly Leu Leu Val Leu Trp Ile Pro
1               5                   10                  15

Gly Ala Ile Gly Asp Ile Gln Met Thr Gln Ser Pro Ala Ser Leu Ser
            20                  25                  30

Ala Ser Leu Gly Glu Thr Val Ser Ile Glu Cys Leu Ala Ser Glu Gly
        35                  40                  45

Ile Ser Asn Asp Leu Ala Trp Tyr Gln Gln Lys Ser Gly Lys Ser Pro
    50                  55                  60

Gln Leu Leu Ile Tyr Ala Thr Ser Arg Leu Gln Asp Gly Val Pro Ser
65                  70                  75                  80

Arg Phe Ser Gly Ser Gly Ser Gly Thr Arg Tyr Ser Leu Lys Ile Ser
                85                  90                  95

Gly Met Gln Pro Glu Asp Glu Ala Asp Tyr Phe Cys Gln Gln Ser Tyr
            100                 105                 110

Lys Tyr Pro Trp Thr Phe Gly Gly Gly Thr Lys Leu Glu Leu Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 4

```
<211> LENGTH: 470
<212> TYPE: PRT
<213> ORGANISM: Mus musculus
<220> FEATURE:
<221> NAME/KEY: SOURCE
<222> LOCATION: 1..470
<223> OTHER INFORMATION: /mol_type="protein"
      /note="MAb EpCAM (mouse EpCAM-specific antibody G8.8), heavy
      chain" /organism="Mus musculus"

<400> SEQUENCE: 4

Met Asp Ile Arg Leu Ser Leu Ala Phe Leu Val Leu Phe Ile Lys Gly
1               5                   10                  15

Val Gln Cys Glu Val Gln Leu Ala Glu Ser Gly Gly Gly Leu Val Gln
            20                  25                  30

Pro Gly Arg Ser Met Lys Leu Ser Cys Ala Ala Ser Gly Phe Thr Phe
        35                  40                  45

Ser Asn Phe Pro Met Ala Trp Val Arg Gln Ala Pro Thr Lys Gly Leu
    50                  55                  60

Glu Trp Val Ala Thr Ile Ser Thr Ser Gly Gly Ser Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asn Ser Leu Arg Ser Glu Asp Thr Ala Thr
            100                 105                 110

Tyr Tyr Cys Thr Arg Thr Leu Tyr Ile Leu Arg Val Phe Tyr Phe Asp
        115                 120                 125

Tyr Trp Gly Gln Gly Val Met Val Thr Val Ser Ser Ala Lys Thr Thr
    130                 135                 140

Ala Pro Ser Val Tyr Pro Leu Ala Pro Val Cys Gly Asp Thr Thr Gly
145                 150                 155                 160

Ser Ser Val Thr Leu Gly Cys Leu Val Lys Gly Tyr Phe Pro Glu Pro
                165                 170                 175

Val Thr Leu Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Thr Ser Ser Thr Trp Pro Ser Gln Ser Ile Thr Cys Asn Val
    210                 215                 220

Ala His Pro Ala Ser Ser Thr Lys Val Asp Lys Lys Ile Glu Pro Arg
225                 230                 235                 240

Gly Pro Thr Ile Lys Pro Cys Pro Pro Cys Lys Cys Pro Ala Pro Asn
                245                 250                 255

Leu Leu Gly Gly Pro Ser Val Phe Ile Phe Pro Pro Lys Ile Lys Asp
            260                 265                 270

Val Leu Met Ile Ser Leu Ser Pro Ile Val Thr Cys Val Val Val Asp
        275                 280                 285

Val Ser Glu Asp Asp Pro Asp Val Gln Ile Ser Trp Phe Val Asn Asn
    290                 295                 300

Val Glu Val His Thr Ala Gln Thr Gln Thr His Arg Glu Asp Tyr Asn
305                 310                 315                 320

Ser Thr Leu Arg Val Val Ser Ala Leu Pro Ile Gln His Gln Asp Trp
                325                 330                 335

Met Ser Gly Lys Glu Phe Lys Cys Lys Val Asn Asn Lys Asp Leu Pro
            340                 345                 350

Ala Pro Ile Glu Arg Thr Ile Ser Lys Pro Lys Gly Ser Val Arg Ala
```

```
        355                 360                 365

Pro Gln Val Tyr Val Leu Pro Pro Pro Glu Glu Glu Met Thr Lys Lys
    370                 375                 380

Gln Val Thr Leu Thr Cys Met Val Thr Asp Phe Met Pro Glu Asp Ile
385                 390                 395                 400

Tyr Val Glu Trp Thr Asn Asn Gly Lys Thr Glu Leu Asn Tyr Lys Asn
                405                 410                 415

Thr Glu Pro Val Leu Asp Ser Asp Gly Ser Tyr Phe Met Tyr Ser Lys
            420                 425                 430

Leu Arg Val Glu Lys Lys Asn Trp Val Glu Arg Asn Ser Tyr Ser Cys
        435                 440                 445

Ser Val Val His Glu Gly Leu His Asn His His Thr Thr Lys Ser Phe
    450                 455                 460

Ser Arg Thr Pro Gly Lys
465                 470


<210> SEQ ID NO 5
<211> LENGTH: 234
<212> TYPE: PRT
<213> ORGANISM: artificial sequences
<220> FEATURE:
<221> NAME/KEY: SOURCE
<222> LOCATION: 1..234
<223> OTHER INFORMATION: /mol_type="protein"
      /note="MAb 225_scFv G8.8 (human EGFR-specific MAb with mouse-EpCA
      M-specific scFv fusion), light chain"
      /organism="artificial sequences"

<400> SEQUENCE: 5

Met Arg Cys Leu Ala Glu Phe Leu Gly Leu Leu Val Leu Trp Ile Pro
1               5                   10                  15

Gly Ala Ile Gly Asp Ile Leu Leu Thr Gln Ser Pro Val Ile Leu Ser
            20                  25                  30

Val Ser Pro Gly Glu Arg Val Ser Phe Ser Cys Arg Ala Ser Gln Ser
        35                  40                  45

Ile Gly Thr Asn Ile His Trp Tyr Gln Gln Arg Thr Asn Gly Ser Pro
    50                  55                  60

Arg Leu Leu Ile Lys Tyr Ala Ser Glu Ser Ile Ser Gly Ile Pro Ser
65                  70                  75                  80

Arg Phe Ser Gly Ser Gly Ser Gly Thr Asp Phe Thr Leu Ser Ile Asn
                85                  90                  95

Ser Val Glu Ser Glu Asp Ile Ala Asp Tyr Tyr Cys Gln Gln Asn Asn
            100                 105                 110

Asn Trp Pro Thr Thr Phe Gly Ala Gly Thr Lys Leu Glu Leu Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220
```

```
Ile Val Lys Ser Phe Asn Arg Asn Glu Cys
225                 230


<210> SEQ ID NO 6
<211> LENGTH: 721
<212> TYPE: PRT
<213> ORGANISM: artificial sequences
<220> FEATURE:
<221> NAME/KEY: SOURCE
<222> LOCATION: 1..721
<223> OTHER INFORMATION: /mol_type="protein"
      /note="MAb 225_scFv G8.8 (human EGFR-specific MAb with mouse-EpCA
      M-specific scFv fusion), heavy chain"
      /organism="artificial sequences"

<400> SEQUENCE: 6

Met Ala Val Leu Ala Leu Leu Phe Cys Leu Val Thr Phe Pro Ser Cys
1               5                   10                  15

Val Leu Ser Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
        35                  40                  45

Thr Asn Tyr Gly Val His Trp Val Arg Gln Ser Pro Gly Lys Gly Leu
    50                  55                  60

Glu Trp Leu Gly Val Ile Trp Ser Gly Gly Asn Thr Asp Tyr Asn Thr
65                  70                  75                  80

Pro Phe Thr Ser Arg Leu Ser Ile Asn Lys Asp Asn Ser Lys Ser Gln
                85                  90                  95

Val Phe Phe Lys Met Asn Ser Leu Gln Ser Asn Asp Thr Ala Ile Tyr
            100                 105                 110

Tyr Cys Ala Arg Ala Leu Thr Tyr Tyr Asp Tyr Glu Phe Ala Tyr Trp
        115                 120                 125

Gly Gln Gly Thr Leu Val Thr Val Ser Ala Ala Lys Thr Thr Ala Pro
    130                 135                 140

Ser Val Tyr Pro Leu Ala Pro Val Cys Gly Asp Thr Thr Gly Ser Ser
145                 150                 155                 160

Val Thr Leu Gly Cys Leu Val Lys Gly Tyr Phe Pro Glu Pro Val Thr
                165                 170                 175

Leu Thr Trp Asn Ser Gly Ser Leu Ser Ser Gly Val His Thr Phe Pro
            180                 185                 190

Ala Val Leu Gln Ser Asp Leu Tyr Thr Leu Ser Ser Ser Val Thr Val
        195                 200                 205

Thr Ser Ser Thr Trp Pro Ser Gln Ser Ile Thr Cys Asn Val Ala His
    210                 215                 220

Pro Ala Ser Ser Thr Lys Val Asp Lys Lys Ile Glu Pro Arg Gly Pro
225                 230                 235                 240

Thr Ile Lys Pro Cys Pro Pro Cys Lys Cys Pro Ala Pro Asn Leu Leu
                245                 250                 255

Gly Gly Pro Ser Val Phe Ile Phe Pro Pro Lys Ile Lys Asp Val Leu
            260                 265                 270

Met Ile Ser Leu Ser Pro Ile Val Thr Cys Val Val Val Asp Val Ser
        275                 280                 285

Glu Asp Asp Pro Asp Val Gln Ile Ser Trp Phe Val Asn Asn Val Glu
    290                 295                 300

Val His Thr Ala Gln Thr Gln Thr His Arg Glu Asp Tyr Asn Ser Thr
305                 310                 315                 320
```

```
Leu Arg Val Val Ser Ala Leu Pro Ile Gln His Gln Asp Trp Met Ser
                325                 330                 335

Gly Lys Glu Phe Lys Cys Lys Val Asn Asn Lys Asp Leu Pro Ala Pro
            340                 345                 350

Ile Glu Arg Thr Ile Ser Lys Pro Lys Gly Ser Val Arg Ala Pro Gln
        355                 360                 365

Val Tyr Val Leu Pro Pro Pro Glu Glu Glu Met Thr Lys Lys Gln Val
    370                 375                 380

Thr Leu Thr Cys Met Val Thr Asp Phe Met Pro Glu Asp Ile Tyr Val
385                 390                 395                 400

Glu Trp Thr Asn Asn Gly Lys Thr Glu Leu Asn Tyr Lys Asn Thr Glu
                405                 410                 415

Pro Val Leu Asp Ser Asp Gly Ser Tyr Phe Met Tyr Ser Lys Leu Arg
            420                 425                 430

Val Glu Lys Lys Asn Trp Val Glu Arg Asn Ser Tyr Ser Cys Ser Val
        435                 440                 445

Val His Glu Gly Leu His Asn His His Thr Thr Lys Ser Phe Ser Arg
    450                 455                 460

Thr Pro Gly Lys Gly Gly Gly Gly Ser Gly Gly Gly Gly Ser Glu Val
465                 470                 475                 480

Gln Leu Ala Glu Ser Gly Gly Gly Leu Val Gln Pro Gly Arg Ser Met
                485                 490                 495

Lys Leu Ser Cys Ala Ala Ser Gly Phe Thr Phe Ser Asn Phe Pro Met
            500                 505                 510

Ala Trp Val Arg Gln Ala Pro Thr Lys Cys Leu Glu Trp Val Ala Thr
        515                 520                 525

Ile Ser Thr Ser Gly Gly Ser Thr Tyr Tyr Arg Asp Ser Val Lys Gly
    530                 535                 540

Arg Phe Thr Ile Ser Arg Asp Asn Ala Lys Ser Thr Leu Tyr Leu Gln
545                 550                 555                 560

Met Asn Ser Leu Arg Ser Glu Asp Thr Ala Thr Tyr Tyr Cys Thr Arg
                565                 570                 575

Thr Leu Tyr Ile Leu Arg Val Phe Tyr Phe Asp Tyr Trp Gly Gln Gly
            580                 585                 590

Val Met Val Thr Val Ser Ser Gly Gly Gly Gly Ser Gly Gly Gly Gly
        595                 600                 605

Ser Gly Gly Gly Gly Ser Asp Ile Gln Met Thr Gln Ser Pro Ala Ser
    610                 615                 620

Leu Ser Ala Ser Leu Gly Glu Thr Val Ser Ile Glu Cys Leu Ala Ser
625                 630                 635                 640

Glu Gly Ile Ser Asn Asp Leu Ala Trp Tyr Gln Gln Lys Ser Gly Lys
                645                 650                 655

Ser Pro Gln Leu Leu Ile Tyr Ala Thr Ser Arg Leu Gln Asp Gly Val
            660                 665                 670

Pro Ser Arg Phe Ser Gly Ser Gly Ser Gly Thr Arg Tyr Ser Leu Lys
        675                 680                 685

Ile Ser Gly Met Gln Pro Glu Asp Glu Ala Asp Tyr Phe Cys Gln Gln
    690                 695                 700

Ser Tyr Lys Tyr Pro Trp Thr Phe Gly Cys Gly Thr Lys Leu Glu Leu
705                 710                 715                 720

Lys
```

<210> SEQ ID NO 7

```
<211> LENGTH: 801
<212> TYPE: DNA
<213> ORGANISM: Mus musculus
<220> FEATURE:
<221> NAME/KEY: source
<222> LOCATION: 1..801
<223> OTHER INFORMATION: /mol_type="DNA"
      /note="murine EpCAM cDNA (encodes amino acids 1 - 267)"
      /organism="Mus musculus"

<400> SEQUENCE: 7

atggctggac ctcaggccct ggcctttggc ctgctgctgg ccgtcgtgac agccacactg     60

gccgctgccc agagggactg cgtgtgcgac aactataagc tggccaccag ctgcagcctg    120

aacgagtacg gcgagtgcca gtgcaccagc tacggcaccc agaacaccgt gatctgcagc    180

aagctggctt ccaagtgcct ggccatgaag gccgagatga cccacagcaa gagcggcaga    240

cggatcaagc ccgagggcgc catccagaac aacgacggcc tgtacgaccc cgactgcgac    300

gagcagggcc tgttcaaggc caagcagtgc aacggcaccg ccacctgttg gtgtgtgaac    360

acagctggcg tgcggcggac agacaaggac accgagatca cctgtagcga gagagtgcgg    420

acctactgga tcatcatcga gctgaagcac aaagagagag agagccccta cgaccaccag    480

agcctgcaga ccgccctgca agaagccttc accagccggt acaagctgaa ccagaagttc    540

atcaagaaca ttatgtacga gaacaacgtg atcaccatcg acctgatgca gaacagcagc    600

cagaaaaccc aggacgacgt ggacattgcc gacgtggcct actacttcga gaaggacgtg    660

aagggcgaga gcctgttcca cagcagcaag agcatggacc tgagagtgaa cggcgagccc    720

ctggacctgg accctggcca gaccctgatc tactacgtgg acgagaaggc ccccgagttc    780

agcatgcagg gcctgaccgc g                                              801


<210> SEQ ID NO 8
<211> LENGTH: 267
<212> TYPE: PRT
<213> ORGANISM: Mus musculus
<220> FEATURE:
<221> NAME/KEY: SOURCE
<222> LOCATION: 1..267
<223> OTHER INFORMATION: /mol_type="protein"
      /note="murine EpCAM protein sequence"
      /organism="Mus musculus"

<400> SEQUENCE: 8

Met Ala Gly Pro Gln Ala Leu Ala Phe Gly Leu Leu Leu Ala Val Val
1               5                   10                  15

Thr Ala Thr Leu Ala Ala Ala Gln Arg Asp Cys Val Cys Asp Asn Tyr
            20                  25                  30

Lys Leu Ala Thr Ser Cys Ser Leu Asn Glu Tyr Gly Glu Cys Gln Cys
        35                  40                  45

Thr Ser Tyr Gly Thr Gln Asn Thr Val Ile Cys Ser Lys Leu Ala Ser
    50                  55                  60

Lys Cys Leu Ala Met Lys Ala Glu Met Thr His Ser Lys Ser Gly Arg
65                  70                  75                  80

Arg Ile Lys Pro Glu Gly Ala Ile Gln Asn Asn Asp Gly Leu Tyr Asp
                85                  90                  95

Pro Asp Cys Asp Glu Gln Gly Leu Phe Lys Ala Lys Gln Cys Asn Gly
            100                 105                 110

Thr Ala Thr Cys Trp Cys Val Asn Thr Ala Gly Val Arg Arg Thr Asp
        115                 120                 125

Lys Asp Thr Glu Ile Thr Cys Ser Glu Arg Val Arg Thr Tyr Trp Ile
```

-continued

```
    130                 135                 140

Ile Ile Glu Leu Lys His Lys Glu Arg Glu Ser Pro Tyr Asp His Gln
145                 150                 155                 160

Ser Leu Gln Thr Ala Leu Gln Glu Ala Phe Thr Ser Arg Tyr Lys Leu
                165                 170                 175

Asn Gln Lys Phe Ile Lys Asn Ile Met Tyr Glu Asn Asn Val Ile Thr
            180                 185                 190

Ile Asp Leu Met Gln Asn Ser Ser Gln Lys Thr Gln Asp Asp Val Asp
        195                 200                 205

Ile Ala Asp Val Ala Tyr Tyr Phe Glu Lys Asp Val Lys Gly Glu Ser
    210                 215                 220

Leu Phe His Ser Ser Lys Ser Met Asp Leu Arg Val Asn Gly Glu Pro
225                 230                 235                 240

Leu Asp Leu Asp Pro Gly Gln Thr Leu Ile Tyr Tyr Val Asp Glu Lys
                245                 250                 255

Ala Pro Glu Phe Ser Met Gln Gly Leu Thr Ala
            260                 265


<210> SEQ ID NO 9
<211> LENGTH: 915
<212> TYPE: DNA
<213> ORGANISM: Artificial Sequence
<220> FEATURE:
<221> NAME/KEY: source
<222> LOCATION: 1..915
<223> OTHER INFORMATION: /mol_type="DNA"
      /note="recombinant murine EpCAM ectodomain"
      /organism="Artificial Sequence"

<400> SEQUENCE: 9

atggctggac ctcaggccct ggcctttggc ctgctgctgg ccgtcgtgac agccacactg     60

gccgctgccc agagggactg cgtgtgcgac aactataagc tggccaccag ctgcagcctg    120

aacgagtacg gcgagtgcca gtgcaccagc tacggcaccc agaacaccgt gatctgcagc    180

aagctggctt ccaagtgcct ggccatgaag gccgagatga cccacagcaa gagcggcaga    240

cggatcaagc ccgagggcgc catccagaac aacgacggcc tgtacgaccc cgactgcgac    300

gagcagggcc tgttcaaggc caagcagtgc aacggcaccg ccacctgttg gtgtgtgaac    360

acagctggcg tgcggcggac agacaaggac accgagatca cctgtagcga gagagtgcgg    420

acctactgga tcatcatcga gctgaagcac aaagagagag agagccccta cgaccaccag    480

agcctgcaga ccgccctgca agaagccttc accagccggt acaagctgaa ccagaagttc    540

atcaagaaca ttatgtacga gaacaacgtg atcaccatcg acctgatgca gaacagcagc    600

cagaaaaccc aggacgacgt ggacattgcc gacgtggcct actacttcga gaaggacgtg    660

aagggcgaga gcctgttcca cagcagcaag agcatggacc tgagagtgaa cggcgagccc    720

ctggacctgg accctggcca gaccctgatc tactacgtgg acgagaaggc ccccgagttc    780

agcatgcagg gcctgaccgc ggccgcactg gaagttctgt tccaggggcc cggtacccac    840

caccaccatc accatcatca ccaccatatt ggcctgaacg atatttttga agcgcagaaa    900

atcgaatggc acgaa                                                      915


<210> SEQ ID NO 10
<211> LENGTH: 305
<212> TYPE: PRT
<213> ORGANISM: artificial sequences
<220> FEATURE:
<221> NAME/KEY: SOURCE
```

```
<222> LOCATION: 1..305
<223> OTHER INFORMATION: /mol_type="protein"
      /note="recombinant murine EpCAM ectodomain"
      /organism="artificial sequences"

<400> SEQUENCE: 10

Met Ala Gly Pro Gln Ala Leu Ala Phe Gly Leu Leu Leu Ala Val Val
1               5                   10                  15

Thr Ala Thr Leu Ala Ala Ala Gln Arg Asp Cys Val Cys Asp Asn Tyr
            20                  25                  30

Lys Leu Ala Thr Ser Cys Ser Leu Asn Glu Tyr Gly Glu Cys Gln Cys
        35                  40                  45

Thr Ser Tyr Gly Thr Gln Asn Thr Val Ile Cys Ser Lys Leu Ala Ser
    50                  55                  60

Lys Cys Leu Ala Met Lys Ala Glu Met Thr His Ser Lys Ser Gly Arg
65                  70                  75                  80

Arg Ile Lys Pro Glu Gly Ala Ile Gln Asn Asn Asp Gly Leu Tyr Asp
                85                  90                  95

Pro Asp Cys Asp Glu Gln Gly Leu Phe Lys Ala Lys Gln Cys Asn Gly
            100                 105                 110

Thr Ala Thr Cys Trp Cys Val Asn Thr Ala Gly Val Arg Arg Thr Asp
        115                 120                 125

Lys Asp Thr Glu Ile Thr Cys Ser Glu Arg Val Arg Thr Tyr Trp Ile
    130                 135                 140

Ile Ile Glu Leu Lys His Lys Glu Arg Glu Ser Pro Tyr Asp His Gln
145                 150                 155                 160

Ser Leu Gln Thr Ala Leu Gln Glu Ala Phe Thr Ser Arg Tyr Lys Leu
                165                 170                 175

Asn Gln Lys Phe Ile Lys Asn Ile Met Tyr Glu Asn Asn Val Ile Thr
            180                 185                 190

Ile Asp Leu Met Gln Asn Ser Ser Gln Lys Thr Gln Asp Asp Val Asp
        195                 200                 205

Ile Ala Asp Val Ala Tyr Tyr Phe Glu Lys Asp Val Lys Gly Glu Ser
    210                 215                 220

Leu Phe His Ser Ser Lys Ser Met Asp Leu Arg Val Asn Gly Glu Pro
225                 230                 235                 240

Leu Asp Leu Asp Pro Gly Gln Thr Leu Ile Tyr Tyr Val Asp Glu Lys
                245                 250                 255

Ala Pro Glu Phe Ser Met Gln Gly Leu Thr Ala Ala Ala Leu Glu Val
            260                 265                 270

Leu Phe Gln Gly Pro Gly Thr His His His His His His His His His
        275                 280                 285

His Ile Gly Leu Asn Asp Ile Phe Glu Ala Gln Lys Ile Glu Trp His
    290                 295                 300

Glu
305


<210> SEQ ID NO 11
<211> LENGTH: 2034
<212> TYPE: DNA
<213> ORGANISM: artificial sequences
<220> FEATURE:
<221> NAME/KEY: source
<222> LOCATION: 1..2034
<223> OTHER INFORMATION: /mol_type="DNA"
      /note="Recombinant human EGFR ectodomain + transmembrane domain"
      /organism="artificial sequences"
```

<400> SEQUENCE: 11

```
atgcgaccct ccgggacggc cggggcagcg ctcctggcgc tgctggctgc gctctgcccg     60

gcgagtcggg ctctggagga aaagaaagtt tgccaaggca cgagtaacaa gctcacgcag    120

ttgggcactt ttgaagatca ttttctcagc ctccagagga tgttcaataa ctgtgaggtg    180

gtccttggga atttggaaat tacctatgtg cagaggaatt atgatctttc cttcttaaag    240

accatccagg aggtggctgg ttatgtcctc attgccctca acacagtgga gcgaattcct    300

ttggaaaacc tgcagatcat cagaggaaat atgtactacg aaaattccta tgccttagca    360

gtcttatcta actatgatgc aaataaaacc ggactgaagg agctgcccat gagaaattta    420

caggaaatcc tgcatggcgc cgtgcggttc agcaacaacc ctgccctgtg caacgtggag    480

agcatccagt ggcgggacat agtcagcagt gactttctca gcaacatgtc gatggacttc    540

cagaaccacc tgggcagctg ccaaaagtgt gatccaagct gtcccaatgg gagctgctgg    600

ggtgcaggag aggagaactg ccagaaactg accaaaatca tctgtgccca gcagtgctcc    660

gggcgctgcc gtggcaagtc ccccagtgac tgctgccaca accagtgtgc tgcaggctgc    720

acaggccccc gggagagcga ctgcctggtc tgccgcaaat tccgagacga agccacgtgc    780

aaggacacct gccccccact catgctctac aaccccacca cgtaccagat ggatgtgaac    840

cccgagggca aatacagctt tggtgccacc tgcgtgaaga agtgtccccg taattatgtg    900

gtgacagatc acggctcgtg cgtccgagcc tgtggggccg acagctatga gatggaggaa    960

gacggcgtcc gcaagtgtaa gaagtgcgaa gggccttgcc gcaaagtgtg taacggaata   1020

ggtattggtg aatttaaaga ctcactctcc ataaatgcta cgaatattaa acacttcaaa   1080

aactgcacct ccatcagtgg cgatctccac atcctgccgg tggcatttag ggggtgactcc  1140

ttcacacata ctcctcctct ggatccacag gaactggata ttctgaaaac cgtaaaggaa   1200

atcacagggt ttttgctgat tcaggcttgg cctgaaaaca ggacggacct ccatgccttt   1260

gagaacctag aaatcatacg cggcaggacc aagcaacatg gtcagttttc tcttgcagtc   1320

gtcagcctga acataacatc cttgggatta cgctccctca aggagataag tgatggagat   1380

gtgataattt caggaaacaa aaatttgtgc tatgcaaata caataaactg gaaaaaactg   1440

tttgggacct ccggtcagaa aaccaaaatt ataagcaaca gaggtgaaaa cagctgcaag   1500

gccacaggcc aggtctgcca tgccttgtgc tcccccgagg gctgctgggg cccggagccc   1560

agggactgcg tctcttgccg gaatgtcagc cgaggcaggg aatgcgtgga caagtgcaac   1620

cttctggagg gtgagccaag ggagtttgtg gagaactctg agtgcataca gtgccaccca   1680

gagtgcctgc ctcaggccat gaacatcacc tgcacaggac ggggaccaga caactgtatc   1740

cagtgtgccc actacattga cggcccccac tgcgtcaaga cctgcccggc aggagtcatg   1800

ggagaaaaca acaccctggt ctggaagtac gcagacgccg gccatgtgtg ccacctgtgc   1860

catccaaact gcacctacgg atgcactggg ccaggtcttg aaggctgtcc aacgaatggg   1920

cctaagatcc cgtccatcgc cactgggatg gtgggggccc tcctcttgct gctggtggtg   1980

gccctgggga tcggcctctt catgcgaagg cgccacatcg ttcggaagcg ctga         2034
```

<210> SEQ ID NO 12
<211> LENGTH: 677
<212> TYPE: PRT
<213> ORGANISM: artificial sequences
<220> FEATURE:
<221> NAME/KEY: SOURCE
<222> LOCATION: 1..677
<223> OTHER INFORMATION: /mol_type="protein"

```
      /note="Recombinant human EGFR ectodomain + transmembrane domain"
      /organism="artificial sequences"

<400> SEQUENCE: 12

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400
```

```
Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg
        675
```

<210> SEQ ID NO 13
<211> LENGTH: 21
<212> TYPE: DNA
<213> ORGANISM: artificial sequences
<220> FEATURE:
<221> NAME/KEY: source
<222> LOCATION: 1..21
<223> OTHER INFORMATION: /mol_type="DNA"
/note="forward primer"
/organism="artificial sequences"

<400> SEQUENCE: 13
cagcatcgtt ctgtgttgtc t 21

<210> SEQ ID NO 14
<211> LENGTH: 24
<212> TYPE: DNA
<213> ORGANISM: artificial sequences
<220> FEATURE:
<221> NAME/KEY: source
<222> LOCATION: 1..24

```
<223> OTHER INFORMATION: /mol_type="DNA"
      /note="primer"
      /organism="artificial sequences"

<400> SEQUENCE: 14

catttaaatg tatacccaaa tcaa                                          24


<210> SEQ ID NO 15
<211> LENGTH: 214
<212> TYPE: PRT
<213> ORGANISM: artificial sequences
<220> FEATURE:
<221> NAME/KEY: SOURCE
<222> LOCATION: 1..214
<223> OTHER INFORMATION: /mol_type="protein"
      /note=""BsAb EpCAM-EGFRvIII, MR1.1□? light chain without leader
      sequence" /organism="artificial sequences"

<400> SEQUENCE: 15

Asp Ile Gln Met Thr Gln Ser Pro Ala Ser Leu Ser Ala Ser Leu Gly
1               5                   10                  15

Glu Thr Val Ser Ile Glu Cys Leu Ala Ser Glu Gly Ile Ser Asn Asp
            20                  25                  30

Leu Ala Trp Tyr Gln Gln Lys Ser Gly Lys Ser Pro Gln Leu Leu Ile
        35                  40                  45

Tyr Ala Thr Ser Arg Leu Gln Asp Gly Val Pro Ser Arg Phe Ser Gly
    50                  55                  60

Ser Gly Ser Gly Thr Arg Tyr Ser Leu Lys Ile Ser Gly Met Gln Pro
65                  70                  75                  80

Glu Asp Glu Ala Asp Tyr Phe Cys Gln Gln Ser Tyr Lys Tyr Pro Trp
                85                  90                  95

Thr Phe Gly Gly Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210


<210> SEQ ID NO 16
<211> LENGTH: 703
<212> TYPE: PRT
<213> ORGANISM: artificial sequences
<220> FEATURE:
<221> NAME/KEY: SOURCE
<222> LOCATION: 1..703
<223> OTHER INFORMATION: /mol_type="protein"
      /note=""BsAb EpCAM-EGFRvIII, MR1.1□? heavy chain without leader
      sequence" /organism="artificial sequences"

<400> SEQUENCE: 16

Glu Val Gln Leu Ala Glu Ser Gly Gly Gly Leu Val Gln Pro Gly Arg
```

-continued

```
1               5                   10                  15

Ser Met Lys Leu Ser Cys Ala Ala Ser Gly Phe Thr Phe Ser Asn Phe
            20                  25                  30

Pro Met Ala Trp Val Arg Gln Ala Pro Thr Lys Gly Leu Glu Trp Val
        35                  40                  45

Ala Thr Ile Ser Thr Ser Gly Gly Ser Thr Tyr Tyr Arg Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ser Glu Asp Thr Ala Thr Tyr Tyr Cys
                85                  90                  95

Thr Arg Thr Leu Tyr Ile Leu Arg Val Phe Tyr Phe Asp Tyr Trp Gly
            100                 105                 110

Gln Gly Val Met Val Thr Val Ser Ser Ala Lys Thr Thr Ala Pro Ser
        115                 120                 125

Val Tyr Pro Leu Ala Pro Val Cys Gly Asp Thr Thr Gly Ser Ser Val
    130                 135                 140

Thr Leu Gly Cys Leu Val Lys Gly Tyr Phe Pro Glu Pro Val Thr Leu
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Thr
            180                 185                 190

Ser Ser Thr Trp Pro Ser Gln Ser Ile Thr Cys Asn Val Ala His Pro
        195                 200                 205

Ala Ser Ser Thr Lys Val Asp Lys Lys Ile Glu Pro Arg Gly Pro Thr
    210                 215                 220

Ile Lys Pro Cys Pro Pro Cys Lys Cys Pro Ala Pro Asn Leu Leu Gly
225                 230                 235                 240

Gly Pro Ser Val Phe Ile Phe Pro Pro Lys Ile Lys Asp Val Leu Met
                245                 250                 255

Ile Ser Leu Ser Pro Ile Val Thr Cys Val Val Val Asp Val Ser Glu
            260                 265                 270

Asp Asp Pro Asp Val Gln Ile Ser Trp Phe Val Asn Asn Val Glu Val
        275                 280                 285

His Thr Ala Gln Thr Gln Thr His Arg Glu Asp Tyr Asn Ser Thr Leu
    290                 295                 300

Arg Val Val Ser Ala Leu Pro Ile Gln His Gln Asp Trp Met Ser Gly
305                 310                 315                 320

Lys Glu Phe Lys Cys Lys Val Asn Asn Lys Asp Leu Pro Ala Pro Ile
                325                 330                 335

Glu Arg Thr Ile Ser Lys Pro Lys Gly Ser Val Arg Ala Pro Gln Val
            340                 345                 350

Tyr Val Leu Pro Pro Pro Glu Glu Glu Met Thr Lys Lys Gln Val Thr
        355                 360                 365

Leu Thr Cys Met Val Thr Asp Phe Met Pro Glu Asp Ile Tyr Val Glu
    370                 375                 380

Trp Thr Asn Asn Gly Lys Thr Glu Leu Asn Tyr Lys Asn Thr Glu Pro
385                 390                 395                 400

Val Leu Asp Ser Asp Gly Ser Tyr Phe Met Tyr Ser Lys Leu Arg Val
                405                 410                 415

Glu Lys Lys Asn Trp Val Glu Arg Asn Ser Tyr Ser Cys Ser Val Val
            420                 425                 430
```

```
His Glu Gly Leu His Asn His His Thr Thr Lys Ser Phe Ser Arg Thr
        435                 440                 445

Pro Gly Lys Gly Gly Gly Gly Ser Gly Gly Gly Gly Ser Gln Val Lys
    450                 455                 460

Leu Gln Gln Ser Gly Gly Gly Leu Val Lys Pro Gly Ala Ser Leu Lys
465                 470                 475                 480

Leu Ser Cys Val Thr Ser Gly Phe Thr Phe Arg Lys Phe Gly Met Ser
                485                 490                 495

Trp Val Arg Gln Thr Ser Asp Lys Arg Leu Glu Trp Val Ala Ser Ile
            500                 505                 510

Ser Thr Gly Gly Tyr Asn Thr Tyr Tyr Ser Asp Asn Val Lys Gly Arg
        515                 520                 525

Phe Thr Ile Ser Arg Glu Asn Ala Lys Asn Thr Leu Tyr Leu Gln Met
    530                 535                 540

Ser Ser Leu Lys Ser Glu Asp Thr Ala Leu Tyr Tyr Cys Thr Arg Gly
545                 550                 555                 560

Tyr Ser Pro Tyr Ser Tyr Ala Met Asp Tyr Trp Gly Gln Gly Thr Thr
                565                 570                 575

Val Thr Val Ser Ser Gly Gly Gly Gly Ser Gly Gly Gly Gly Ser Gly
            580                 585                 590

Gly Gly Gly Ser Asp Ile Glu Leu Thr Gln Ser Pro Ala Ser Leu Ser
        595                 600                 605

Val Ala Thr Gly Glu Lys Val Thr Ile Arg Cys Met Thr Ser Thr Asp
    610                 615                 620

Ile Asp Asp Asp Met Asn Trp Tyr Gln Gln Lys Pro Gly Glu Pro Pro
625                 630                 635                 640

Lys Phe Leu Ile Ser Glu Gly Asn Thr Leu Arg Pro Gly Val Pro Ser
                645                 650                 655

Arg Phe Ser Ser Ser Gly Thr Gly Thr Asp Phe Val Phe Thr Ile Glu
            660                 665                 670

Asn Thr Leu Ser Glu Asp Val Gly Asp Tyr Tyr Cys Leu Gln Ser Trp
        675                 680                 685

Asn Val Pro Leu Thr Phe Gly Asp Gly Thr Lys Leu Glu Ile Lys
    690                 695                 700


<210> SEQ ID NO 17
<211> LENGTH: 1253
<212> TYPE: DNA
<213> ORGANISM: artificial sequences
<220> FEATURE:
<221> NAME/KEY: source
<222> LOCATION: 1..1253
<223> OTHER INFORMATION: /mol_type="DNA"
      /note="del-hEGFRvIII"
      /organism="artificial sequences"

<400> SEQUENCE: 17

gcggccgcgc caccatgcga ccctccggga cggccggggc agcgctcctg gcgctgctgg      60

ctgcgctctg cccggcgagt cgggctctgg aggaaaagaa aggtaattat gtggtgacag     120

atcacggctc gtgcgtccga gcctgtgggg ccgacagcta tgagatggag gaagacggcg     180

tccgcaagtg taagaagtgc gaagggcctt gccgcaaagt gtgtaacgga ataggtattg     240

gtgaatttaa agactcactc tccataaatg ctacgaatat taaacacttc aaaaactgca     300

cctccatcag tggcgatctc cacatcctgc cggtggcatt taggggtgac tccttcacac     360

atactcctcc tctggatcca caggaactgg atattctgaa aaccgtaaag gaaatcacag     420
```

```
ggtttttgct gattcaggct tggcctgaaa acaggacgga cctccatgcc tttgagaacc    480

tagaaatcat acgcggcagg accaagcaac atggtcagtt ttctcttgca gtcgtcagcc    540

tgaacataac atccttggga ttacgctccc tcaaggagat aagtgatgga gatgtgataa    600

tttcaggaaa caaaaatttg tgctatgcaa atacaataaa ctggaaaaaa ctgtttggga    660

cctccggtca gaaaaccaaa attataagca acagaggtga aaacagctgc aaggccacag    720

gccaggtctg ccatgccttg tgctcccccg agggctgctg gggcccggag cccagggact    780

gcgtctcttg ccggaatgtc agccgaggca gggaatgcgt ggacaagtgc aaccttctgg    840

agggtgagcc aagggagttt gtggagaact ctgagtgcat acagtgccac ccagagtgcc    900

tgcctcaggc catgaacatc acctgcacag gacggggacc agacaactgt atccagtgtg    960

cccactacat tgacggcccc cactgcgtca agacctgccc ggcaggagtc atgggagaaa   1020

acaacaccct ggtctggaag tacgcagacg ccggccatgt gtgccacctg tgccatccaa   1080

actgcaccta cggatgcact gggccaggtc ttgaaggctg tccaacgaat gggcctaaga   1140

tcccgtccat cgccactggg atggtggggg ccctcctctt gctgctggtg gtggccctgg   1200

ggatcggcct cttcatgcga aggcgccaca tcgttcggaa gcgctgagaa ttc          1253
```

```
<210> SEQ ID NO 18
<211> LENGTH: 410
<212> TYPE: PRT
<213> ORGANISM: artificial sequences
<220> FEATURE:
<221> NAME/KEY: SOURCE
<222> LOCATION: 1..410
<223> OTHER INFORMATION: /mol_type="protein"
      /note="del-hEGFRvIII"
      /organism="artificial sequences"

<400> SEQUENCE: 18

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Asn Tyr
            20                  25                  30

Val Val Thr Asp His Gly Ser Cys Val Arg Ala Cys Gly Ala Asp Ser
        35                  40                  45

Tyr Glu Met Glu Glu Asp Gly Val Arg Lys Cys Lys Lys Cys Glu Gly
    50                  55                  60

Pro Cys Arg Lys Val Cys Asn Gly Ile Gly Ile Gly Glu Phe Lys Asp
65                  70                  75                  80

Ser Leu Ser Ile Asn Ala Thr Asn Ile Lys His Phe Lys Asn Cys Thr
                85                  90                  95

Ser Ile Ser Gly Asp Leu His Ile Leu Pro Val Ala Phe Arg Gly Asp
            100                 105                 110

Ser Phe Thr His Thr Pro Pro Leu Asp Pro Gln Glu Leu Asp Ile Leu
        115                 120                 125

Lys Thr Val Lys Glu Ile Thr Gly Phe Leu Leu Ile Gln Ala Trp Pro
    130                 135                 140

Glu Asn Arg Thr Asp Leu His Ala Phe Glu Asn Leu Glu Ile Ile Arg
145                 150                 155                 160

Gly Arg Thr Lys Gln His Gly Gln Phe Ser Leu Ala Val Val Ser Leu
                165                 170                 175

Asn Ile Thr Ser Leu Gly Leu Arg Ser Leu Lys Glu Ile Ser Asp Gly
            180                 185                 190
```

-continued

```
Asp Val Ile Ile Ser Gly Asn Lys Asn Leu Cys Tyr Ala Asn Thr Ile
        195                 200                 205

Asn Trp Lys Lys Leu Phe Gly Thr Ser Gly Gln Lys Thr Lys Ile Ile
    210                 215                 220

Ser Asn Arg Gly Glu Asn Ser Cys Lys Ala Thr Gly Gln Val Cys His
225                 230                 235                     240

Ala Leu Cys Ser Pro Glu Gly Cys Trp Gly Pro Glu Pro Arg Asp Cys
                245                 250                 255

Val Ser Cys Arg Asn Val Ser Arg Gly Arg Glu Cys Val Asp Lys Cys
            260                 265                 270

Asn Leu Leu Glu Gly Glu Pro Arg Glu Phe Val Glu Asn Ser Glu Cys
        275                 280                 285

Ile Gln Cys His Pro Glu Cys Leu Pro Gln Ala Met Asn Ile Thr Cys
    290                 295                 300

Thr Gly Arg Gly Pro Asp Asn Cys Ile Gln Cys Ala His Tyr Ile Asp
305                 310                 315                     320

Gly Pro His Cys Val Lys Thr Cys Pro Ala Gly Val Met Gly Glu Asn
                325                 330                 335

Asn Thr Leu Val Trp Lys Tyr Ala Asp Ala Gly His Val Cys His Leu
            340                 345                 350

Cys His Pro Asn Cys Thr Tyr Gly Cys Thr Gly Pro Gly Leu Glu Gly
        355                 360                 365

Cys Pro Thr Asn Gly Pro Lys Ile Pro Ser Ile Ala Thr Gly Met Val
    370                 375                 380

Gly Ala Leu Leu Leu Leu Leu Val Val Ala Leu Gly Ile Gly Leu Phe
385                 390                 395                     400

Met Arg Arg Arg His Ile Val Arg Lys Arg
                405                 410
```